US011318088B2

(12) United States Patent
Popov

(10) Patent No.: US 11,318,088 B2
(45) Date of Patent: May 3, 2022

(54) COMPOSITIONS AND METHODS UTILIZING POLY(VINYL ALCOHOL) AND/OR OTHER POLYMERS THAT AID PARTICLE TRANSPORT IN MUCUS

(71) Applicant: Kala Pharmaceuticals, Inc., Watertown, MA (US)

(72) Inventor: Alexey Popov, Waltham, MA (US)

(73) Assignee: Kala Pharmaceuticals, Inc., Arlington, MA (US)

( * ) Notice: Subject to any disclaimer, the term of this patent is extended or adjusted under 35 U.S.C. 154(b) by 0 days.

(21) Appl. No.: 16/883,778

(22) Filed: May 26, 2020

(65) Prior Publication Data

US 2020/0289405 A1  Sep. 17, 2020

Related U.S. Application Data

(62) Division of application No. 13/886,514, filed on May 3, 2013, now Pat. No. 10,688,041.

(60) Provisional application No. 61/642,261, filed on May 3, 2012.

(51) Int. Cl.
| | | |
|---|---|---|
| *A61K 9/00* | (2006.01) | |
| *A61K 47/32* | (2006.01) | |
| *A61K 9/10* | (2006.01) | |
| *A61K 9/51* | (2006.01) | |
| *A61K 31/56* | (2006.01) | |
| *A61K 9/50* | (2006.01) | |
| *A61K 38/00* | (2006.01) | |

(52) U.S. Cl.
CPC .............. *A61K 9/0012* (2013.01); *A61K 9/10* (2013.01); *A61K 9/5026* (2013.01); *A61K 9/5138* (2013.01); *A61K 31/56* (2013.01); *A61K 47/32* (2013.01); *A61K 38/00* (2013.01)

(58) Field of Classification Search
CPC ........ A61K 9/0012; A61K 47/32; A61K 9/10; A61K 9/5138; A61K 31/56; A61K 9/5026; A61K 38/00
See application file for complete search history.

(56) References Cited

U.S. PATENT DOCUMENTS

| | | |
|---|---|---|
| 4,757,128 A | 7/1988 | Domb et al. |
| 4,789,724 A | 12/1988 | Domb et al. |
| 4,792,598 A | 12/1988 | Ziegast |
| 4,839,343 A | 6/1989 | Waeber et al. |
| 4,868,274 A | 6/1989 | Gupta et al. |
| 4,904,479 A | 2/1990 | Illum |
| 4,906,474 A | 3/1990 | Langer et al. |
| 4,910,225 A | 3/1990 | Ogawa et al. |
| 4,996,335 A | 2/1991 | Bodor |
| 4,999,417 A | 3/1991 | Domb et al. |
| 5,145,684 A | 9/1992 | Liversidge et al. |
| 5,298,262 A | 3/1994 | Na et al. |
| 5,364,884 A | 11/1994 | Varma et al. |
| 5,429,824 A | 7/1995 | June |
| 5,518,187 A | 5/1996 | Bruno et al. |
| 5,534,259 A | 7/1996 | Zalipsky et al. |
| 5,540,930 A | 7/1996 | Guy |
| 5,543,158 A | 8/1996 | Gref et al. |
| 5,552,160 A | 9/1996 | Liversidge et al. |
| 5,567,435 A | 10/1996 | Hubbell |
| 5,576,311 A | 11/1996 | Guy |
| 5,578,325 A | 11/1996 | Domb et al. |
| 5,612,053 A | 3/1997 | Baichwal et al. |
| 5,665,331 A | 9/1997 | Bagchi et al. |
| 5,696,298 A | 12/1997 | Emanuele |
| 5,718,388 A | 2/1998 | Czekai et al. |
| 5,718,921 A | 2/1998 | Mathiowitz et al. |
| 5,747,061 A | 5/1998 | Aselem et al. |
| 5,800,807 A | 9/1998 | Hu et al. |
| 5,862,999 A | 1/1999 | Czekai et al. |
| 5,869,130 A | 2/1999 | Ferrier |
| 5,916,596 A | 6/1999 | Desai et al. |
| 5,922,357 A | 7/1999 | Coombes et al. |
| 5,989,591 A | 11/1999 | Nagi et al. |
| 6,106,819 A | 8/2000 | Sucher |

(Continued)

FOREIGN PATENT DOCUMENTS

| | | |
|---|---|---|
| AU | 2006220411 A1 | 10/2006 |
| CA | 2 564 982 A1 | 11/2005 |

(Continued)

OTHER PUBLICATIONS

US 5,685,309 A, 11/1997, Edwards et al. (withdrawn)
Albertsson et al, "Synthesis, Characterization and Degradation of Aliphatic Polyanhydrides", British Polymer Journal, (1990), vol. 23, No. 3, pp. 205-212.
Apgar et al., "Multiple-Particle Tracking Measurements of the Heterogeneities in Solutions of Actin Filaments and Actin Bundles", Biophysical Journal, (Aug. 2000), vol. 79, No. 2, pp. 1095-1106.

(Continued)

*Primary Examiner* — Quanglong N Truong
(74) *Attorney, Agent, or Firm* — K&L Gates LLP; Louis C. Cullman; Michelle Glasky Bergman

(57) ABSTRACT

Particles, compositions, and methods that aid particle transport in mucus are provided. The compositions and methods may include, in some embodiments, modifying the surface coatings of particles including pharmaceutical agents that have a low water/aqueous solubility. In some embodiments, a surface coating includes a synthetic polymer having pendant hydroxyl groups on the backbone of the polymer, such as poly(vinyl alcohol) (PVA). Such compositions and methods can be used to achieve efficient transport of particles of pharmaceutical agents though mucus barriers in the body for a wide spectrum of applications, including drug delivery, imaging, and diagnostic applications. In certain embodiments, a pharmaceutical composition including such particles is well-suited for administration routes involving the particles passing through a mucosal barrier.

22 Claims, 14 Drawing Sheets

(56) References Cited

U.S. PATENT DOCUMENTS

| | | |
|---|---|---|
| 6,153,607 A | 11/2000 | Pflugfelder et al. |
| 6,165,509 A | 12/2000 | Hoffman et al. |
| 6,197,346 B1 | 3/2001 | Mathiowitz et al. |
| 6,217,908 B1 | 4/2001 | Mathiowitz et al. |
| 6,235,313 B1 | 5/2001 | Mathiowitz et al. |
| 6,264,981 B1 | 7/2001 | Zhang et al. |
| 6,270,806 B1 | 8/2001 | Liversidge |
| 6,287,588 B1 | 9/2001 | Shih |
| 6,365,187 B2 | 4/2002 | Mathiowitz et al. |
| 6,372,246 B1 | 4/2002 | Wei et al. |
| 6,413,539 B1 | 7/2002 | Shalaby |
| 6,432,381 B2 | 8/2002 | Liversidge |
| 6,495,164 B1 | 12/2002 | Ramstack |
| 6,589,549 B2 | 7/2003 | Shih |
| 6,610,318 B1 | 8/2003 | Bellmann et al. |
| 6,627,228 B1 | 9/2003 | Milstein et al. |
| 6,703,039 B2 | 3/2004 | Xia et al. |
| 6,706,289 B2 | 3/2004 | Lewis et al. |
| 7,060,299 B2 | 6/2006 | Alavattam et al. |
| 7,153,524 B2 | 12/2006 | Yoshihara et al. |
| 7,157,426 B2 | 1/2007 | Quay et al. |
| 7,163,697 B2 | 1/2007 | Hanes et al. |
| 7,495,052 B2 | 2/2009 | Raiche et al. |
| 7,534,449 B2 | 5/2009 | Saltzman et al. |
| 7,550,441 B2 | 6/2009 | Farokhzad et al. |
| 7,544,371 B2 | 9/2009 | Kunzler et al. |
| 7,659,259 B2 | 2/2010 | Xia et al. |
| 7,763,278 B2 | 7/2010 | Cooper et al. |
| 7,795,237 B2 | 9/2010 | Ahmed et al. |
| 7,842,232 B2 | 11/2010 | Bosch et al. |
| 7,906,136 B2 | 3/2011 | Wong et al. |
| 8,133,512 B2 | 3/2012 | Kunzler et al. |
| 8,354,476 B2 | 1/2013 | Hanes et al. |
| 8,409,607 B2 | 4/2013 | Hughes |
| 8,465,776 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,633,172 B2 | 1/2014 | Loftsson et al. |
| 8,663,674 B2 | 3/2014 | Wen |
| 8,758,816 B2 | 6/2014 | Fuge et al. |
| 8,859,525 B2 | 10/2014 | Marlow et al. |
| 8,889,193 B2 | 11/2014 | McDonnell |
| 8,911,768 B2 | 12/2014 | Whitcup |
| 8,957,034 B2 | 2/2015 | Hanes |
| 8,962,577 B2 | 2/2015 | Hanes |
| 9,056,057 B2 | 6/2015 | Popov |
| 2002/0035264 A1 | 3/2002 | Karali |
| 2002/0068090 A1 | 6/2002 | Bell et al. |
| 2003/0086895 A1 | 5/2003 | Hanes et al. |
| 2004/0071778 A1 | 4/2004 | Bellmann et al. |
| 2004/0076670 A1 | 4/2004 | Klinksick et al. |
| 2004/0175429 A1 | 9/2004 | Alavattam et al. |
| 2004/0209807 A1 | 10/2004 | Quay et al. |
| 2004/0234611 A1 | 11/2004 | Ahlheim |
| 2004/0258763 A1 | 12/2004 | Bell |
| 2005/0009910 A1 | 1/2005 | Hughes |
| 2005/0058603 A1 | 3/2005 | Gao et al. |
| 2005/0065091 A1 | 3/2005 | Peyman |
| 2005/0095205 A1 | 5/2005 | Krishnamoorthy |
| 2005/0101676 A1 | 5/2005 | Fahl et al. |
| 2005/0182039 A1 | 8/2005 | Meyering |
| 2005/0191359 A1 | 9/2005 | Goldshtein et al. |
| 2005/0266067 A1 | 12/2005 | Sengupta et al. |
| 2005/0266090 A1 | 12/2005 | Prokop et al. |
| 2006/0018949 A1 | 1/2006 | Ammon et al. |
| 2006/0083781 A1 | 4/2006 | Shastri et al. |
| 2006/0210622 A1 | 9/2006 | Pace et al. |
| 2006/0257487 A1 | 11/2006 | Owen et al. |
| 2007/0071756 A1 | 3/2007 | Peyman |
| 2007/0093461 A1 | 4/2007 | Shafiee |
| 2007/0110812 A1 | 5/2007 | Xia et al. |
| 2007/0141143 A1 | 6/2007 | Smithey |
| 2007/0149480 A1 | 6/2007 | Ghosh et al. |
| 2007/0149593 A1 | 6/2007 | Ghosh |
| 2007/0178051 A1 | 8/2007 | Pruitt et al. |
| 2007/0212420 A1 | 9/2007 | Xia et al. |
| 2007/0218103 A1 | 9/2007 | Kunzler et al. |
| 2007/0218104 A1 | 9/2007 | Kunzler et al. |
| 2007/0231360 A1 | 10/2007 | Peyman |
| 2007/0249536 A1 | 10/2007 | Ma |
| 2007/0292524 A1 | 12/2007 | Ringe et al. |
| 2007/0299044 A1 | 12/2007 | Farng et al. |
| 2008/0086199 A1 | 4/2008 | Dave |
| 2008/0102128 A1 | 5/2008 | Constancis et al. |
| 2008/0145432 A1 | 6/2008 | Kakizawa |
| 2008/0159984 A1 | 7/2008 | Ben-Sasson |
| 2008/0166411 A1 | 7/2008 | Shah |
| 2008/0166414 A1 | 7/2008 | Hanes et al. |
| 2008/0175887 A1 | 7/2008 | Wang |
| 2008/0194468 A1 | 8/2008 | Bodor |
| 2008/0248125 A1 | 10/2008 | Irache Garreta et al. |
| 2008/0267876 A1 | 10/2008 | Benita et al. |
| 2008/0305172 A1 | 12/2008 | Ahlheim |
| 2008/0306039 A1 | 12/2008 | Matsuhisa |
| 2009/0074786 A1 | 3/2009 | Dor et al. |
| 2009/0087493 A1 | 4/2009 | Dai et al. |
| 2009/0087494 A1 | 4/2009 | Kompella et al. |
| 2009/0155182 A1 | 6/2009 | Mauro et al. |
| 2009/0203709 A1 | 8/2009 | Steinberg |
| 2009/0226531 A1 | 9/2009 | Lyons et al. |
| 2009/0247604 A1 | 10/2009 | Tang |
| 2010/0074957 A1 | 3/2010 | Robinson et al. |
| 2010/0076045 A1 | 3/2010 | Castillo et al. |
| 2010/0215580 A1 | 8/2010 | Hanes |
| 2010/0222308 A1 | 9/2010 | Zhang et al. |
| 2010/0227905 A1 | 9/2010 | Kabra |
| 2010/0247668 A1 | 9/2010 | Eliasof et al. |
| 2010/0290983 A1 | 11/2010 | Rabinow et al. |
| 2010/0311808 A1 | 12/2010 | Lyons et al. |
| 2012/0028910 A1 | 2/2012 | Combal |
| 2012/0052041 A1 | 3/2012 | Basu |
| 2012/0053161 A1 | 3/2012 | Castillo et al. |
| 2012/0121653 A1 | 5/2012 | Jenkins et al. |
| 2012/0121718 A1 | 5/2012 | Lai et al. |
| 2012/0157499 A1 | 6/2012 | Hughes |
| 2012/0252756 A1 | 10/2012 | Coffey et al. |
| 2012/0269894 A1 | 10/2012 | Ahlheim |
| 2012/0289486 A1 | 11/2012 | Bodor |
| 2012/0321719 A1 | 12/2012 | McDonnell et al. |
| 2013/0071349 A1 | 3/2013 | Robinson |
| 2013/0236556 A1 | 3/2013 | Lai |
| 2013/0122064 A1 | 5/2013 | Ahlheim |
| 2013/0164343 A1 | 6/2013 | Hanes |
| 2013/0177609 A1 | 7/2013 | Proksch et al. |
| 2013/0183244 A1 | 7/2013 | Hanes |
| 2013/0210912 A1 | 8/2013 | Davio et al. |
| 2013/0217657 A1 | 8/2013 | Lindstrom |
| 2013/0272994 A1 | 10/2013 | Hanes |
| 2013/0274217 A1 | 10/2013 | Hanes |
| 2013/0316001 A1 | 11/2013 | Popov |
| 2013/0316006 A1 | 11/2013 | Popov et al. |
| 2013/0316009 A1 | 11/2013 | Popov |
| 2013/0323313 A1 | 12/2013 | Suk |
| 2014/0031408 A1 | 1/2014 | Edelman |
| 2014/0107025 A1 | 4/2014 | Wirostko |
| 2014/0178475 A1 | 6/2014 | Figueiredo |
| 2014/0248358 A1 | 9/2014 | Figueiredo |
| 2014/0249158 A1 | 9/2014 | Figueiredo |
| 2014/0276482 A1 | 9/2014 | Astafieva |
| 2014/0294986 A1 | 10/2014 | Liu |
| 2014/0296191 A1 | 10/2014 | Patel et al. |
| 2014/0329913 A1 | 11/2014 | Hanes |
| 2014/0378401 A1 | 12/2014 | Horn |
| 2015/0038473 A1 | 2/2015 | Stein et al. |
| 2015/0044270 A1 | 2/2015 | McDonnell |
| 2015/0086484 A1 | 3/2015 | Hanes |
| 2015/0125539 A1 | 5/2015 | Popov |
| 2015/0265542 A1 | 9/2015 | Popov |

(56) References Cited

U.S. PATENT DOCUMENTS

| | | | |
|---|---|---|---|
| 2015/0265543 A1 | 9/2015 | Popov | |
| 2015/0297531 A1 | 10/2015 | Ensign | |

FOREIGN PATENT DOCUMENTS

| | | |
|---|---|---|
| CN | 101129385 | 2/2008 |
| CN | 101317847 | 10/2008 |
| EP | 0 692 510 B1 | 12/2004 |
| EP | 1 744 759 B1 | 9/2009 |
| EP | 2 127 655 A1 | 12/2009 |
| EP | 2335686 | 6/2011 |
| JP | 2011-140470 | 7/2011 |
| WO | 95/03356 A1 | 2/1995 |
| WO | 95/11669 A1 | 5/1995 |
| WO | 95/22318 A1 | 8/1995 |
| WO | 97/20578 A1 | 6/1997 |
| WO | 97/44013 A1 | 11/1997 |
| WO | 98/29097 A1 | 7/1998 |
| WO | 98/31346 A1 | 7/1998 |
| WO | 99/01498 A1 | 1/1999 |
| WO | 00/46147 A2 | 8/2000 |
| WO | 02/38127 A2 | 5/2002 |
| WO | 02/053189 A2 | 7/2002 |
| WO | 03/000237 A2 | 1/2003 |
| WO | 2004060977 | 7/2004 |
| WO | 2004/069225 | 8/2004 |
| WO | 2005/046671 A1 | 5/2005 |
| WO | 2005055985 A1 | 6/2005 |
| WO | 2005/072710 A2 | 8/2005 |
| WO | 2005/094836 A2 | 10/2005 |
| WO | 2006/044660 A2 | 4/2006 |
| WO | 2006/062875 | 6/2006 |
| WO | 2006/063249 A2 | 6/2006 |
| WO | 2006063249 | 6/2006 |
| WO | 2006091780 A2 | 8/2006 |
| WO | 2006094808 | 9/2006 |
| WO | 2007084418 | 7/2007 |
| WO | 2007/133808 A2 | 11/2007 |
| WO | 2008/030557 A2 | 3/2008 |
| WO | 2008/033924 A2 | 3/2008 |
| WO | 2010040188 | 4/2008 |
| WO | 2008/103673 | 8/2008 |
| WO | 2008/124632 A1 | 10/2008 |
| WO | 2009061607 | 5/2009 |
| WO | 2010132664 | 11/2010 |
| WO | 2011080148 A2 | 7/2011 |
| WO | 2011097347 | 8/2011 |
| WO | 2011/106168 A1 | 9/2011 |
| WO | 2011106702 | 9/2011 |
| WO | 2011/157428 A2 | 12/2011 |
| WO | 2011/159328 A1 | 12/2011 |
| WO | 2012/013884 A1 | 2/2012 |
| WO | 2012/014114 A1 | 2/2012 |
| WO | 2012/038942 A1 | 3/2012 |
| WO | 2012/038943 A1 | 3/2012 |
| WO | 2012/038944 A1 | 3/2012 |
| WO | 2012/039979 A2 | 3/2012 |
| WO | 2012054923 | 4/2012 |
| WO | 2012/059158 A1 | 5/2012 |
| WO | 2012/061703 A1 | 5/2012 |
| WO | 2012/071042 A1 | 5/2012 |
| WO | 2012/074980 A2 | 6/2012 |
| WO | 2012/088431 A1 | 6/2012 |
| WO | 2012/088469 A1 | 6/2012 |
| WO | 2012/093117 A1 | 7/2012 |
| WO | 2012/109363 A2 | 8/2012 |
| WO | 2012/127506 A1 | 9/2012 |
| WO | 2012/149228 A1 | 11/2012 |
| WO | 2012/155062 A1 | 11/2012 |
| WO | 2012/162698 A1 | 11/2012 |
| WO | 2013/040347 A1 | 3/2013 |
| WO | 2013/061269 A1 | 5/2013 |
| WO | 2013/065028 A1 | 5/2013 |
| WO | 2013/090804 A2 | 6/2013 |
| WO | 2013110028 | 7/2013 |
| WO | 2013138343 | 9/2013 |
| WO | 2013138346 | 9/2013 |
| WO | 2013166385 | 11/2013 |
| WO | 2013166408 | 11/2013 |
| WO | 2013166436 | 11/2013 |
| WO | 2013166498 | 11/2013 |
| WO | 2014047439 | 3/2014 |

OTHER PUBLICATIONS

Batrakove et al., "Pluronic Block Copolymers: Evolution of Drug Delivery Concept from Inert Nanocarriers to Biological Response Modifiers", J. Control Release, (Sep. 10, 2008), vol. 130, No. 2, 25 pages.

Bhalla, "Microtubule-targeted anticancer agents and apoptosis", Oncogene, (2003), vol. 22, pp. 9075-9086.

Boskey et al., "A Self-Sampling Method to Obtain Large Volumes of Undiluted Cervicovaginal Secretions", Sexually Transmitted Diseases, (Feb. 2003), vol. 30, No. 2, pp. 107-109.

Boylan et al., "Enhancement of airway gene transfer by DNA nanoparticles using a pH-responsive block copolymer glycol and poly-L-lysine", Biomaterials, (2012) vol. 33, pp. 2361-2371.

Boylan et al., "Highly compacted DNA nanoparticles with low MW PEG coatings: In vitro, ex vivo and in vivo evaluation", Journal of Controlled Release, (2012), vol. 157, pp. 72-79.

Brorson et al., "Mutational Analysis of Avidity and Fine Specificity of Anti-Levan Antibodies", The Journal of Immunology, (1999), pp. 6694-6701.

Brummell et al., "Probing the Combining Site of an Anti-Carbohydrate Antibody by Saturation-Mutagenesis: Role of the Heavy-Chain CDR3 Residues", Biochemistry, (1993), vol. 32, No. 4, pp. 1180-1187.

Bures et al., "Surface modifications and molecular imprinting of polymers in medical and pharmaceutical applications", Journal of Controlled Release, (2001), vol. 72, pp. 25-33.

Burks et al., "In vitro scanning saturation mutagenesis of an antibody binding pocket", Proc. Natl. Acad. Sci. USA, (Jan. 1997), vol. 94, pp. 412-417.

Chan et al., "Phase behavior and miscibility in blends of poly(sebacic anhydride)/poly(ethylene glycol)", Biomaterials, (2002), vol. 23, pp. 2353-2358.

Bin Choy et al., "Mucoadhesive Microparticles Engineered for Ophthalmic Drug Delivery", J. Phys. Chem Solids, (May 2008), vol. 69, No. 5-6, 8 pages.

Colman, "Effects of amino acid sequence changes on antibody-antigen interactions", Research in Immunology, (1994), vol. 145, pp. 33-36.

Cone, "Barrier properties of mucus", Advanced Drug Delivery Reviews, (2009), vol. 61, pp. 75-85.

Cone, "Mucus", Mucosal Immunology, (1999), Section Edition, Chapter 4, pp. 43-64.

Cu et al., "Controlled surface modification with poly(ethylene)glycol enhances diffusion of PLGA nanoparticles in human cervical mucus", Mol Pharm., (2009), vol. 6, No. 1, 18 pages.

Dawson et al., "Transport of Polymeric Nanoparticle Gene Carriers in Gastric Mucus", Biotechnol. Prog., (2004), vol. 20, No. 3, pp. 851-857.

Dawson et al., "Enhanced Viscoelasticity of Human Cystic Fibrotic Sputum Correlates with Increasing Microheterogeneity in Particle Transport", The Journal of Biological Chemistry, (2003), vol. 278, No. 50, pp. 50393-50401.

Dawson et al., "Primary parenteral transmission of bovine spongiform encephalopathy to the pig", The Veterinary Record, (Sep. 29, 1990), 1 page.

De Campos et al., "The effect of a PEG versus a chitosan coating on the interaction of drug colloidal carriers with the ocular mucosa", European Journal of Pharmaceutical Sciences, (2003), vol. 20, pp. 73-81.

Delgado et al., "Radiolabelled biodegradable microspheres for lung imaging", European Journal of Pharmaceutics and Biopharmaceutics, (2000), vol. 50, pp. 227-236.

Denis-Mize et al., "Plasmid DNA adsorbed onto cationic microparticles mediates target gene expression and antigen presentation by dendritic cells", Gene Therapy, (2000), vol. 7, pp. 2105-2112.

(56) References Cited

OTHER PUBLICATIONS

Donaldson et al., "A placebo-controlled multi-centred evaluation of an anaesthetic gel (Oraqix®) for periodontal therapy", Journal of Clinical Peridontology, (2003), vol. 30, pp. 171-175.
Dufner et al., "Harnessing phage and ribosome display for antibody optimisation", TRENDS in Biotechnology, (2006), vol. 24, No. 11, pp. 523-529.
Dumortier et al., "A Review of Poloxamer 407 Pharmaceutical and Pharmacological Characteristics", Pharmaceutical Research, (Dec. 2006), vol. 23, No. 12, pp. 2709-2728.
Ehrhardt et al., "Drug Absorption by the Respiratory Mucosa: Cell Culture Models and Particulate Drug Carriers", Journal of Aerosol Medicine, (2002), vol. 15, No. 2, pp. 131-139.
Emanuele, "FLOCOR™: a new anti-adhesive, rheologic agent", Expert Opinion on Investigational Drugs, (1998), vol. 7, No. 7, pp. 1193-1200.
Ensign et al., "Oral drug delivery with polymeric nanoparticles: The gastrointestinal mucus barriers", Advanced Drug Delivery Reviews, (2012), vol. 64, pp. 557-570.
Ensign et al., "Mucus Penetrating Nanoparticles: Biophysical Tool and Method of Drug and Gene Delivery", Advanced Materials, (2012), vol. 24, pp. 3887-3894.
Ensign et al., "Enhanced vaginal drug delivery through the use of hypotonic formulations that induce fluid uptake", Biomaterials, (2013), vol. 34, pp. 6922-6929.
Ensign et al., "Ex Vivo Characterization of Particle Transport in Mucus Secretions Coating Freshly Excised Mucosal Tissues", Molecular Pharmaceutics, (2013), vol. 10, pp. 2176-2182.
Ensign et al., "Mucus-Penetrating Nanoparticles for Vaginal Drug Deliver Protect Against Herpes Simplex Virus", Science Translational Medicine, (2012), vol. 4, Issue 138, pp. 1-10.
Escobar-Chávez et al., "Application of Thermo-Reversible Pluronic F-127 Gels in Pharmaceutical Formulations", J. Pharm. Pharmaceut. Sci., (2006), vol. 9, No. 3, pp. 339-358.
Farokhzad et al., "Targeted nanoparticle-aptamer bioconjugates for cancer chemotherapy in vivo", PNAS, (Apr. 18, 2006), vol. 103, No. 16, pp. 6315-6320.
Fresta et al., "Ocular Tolerability and In Vivo Bioavailability of Poly(ethylene glycol) (PEG)-Coated Polyethyl-2-Cyanoacrylate Nanosphere-Encapsulated Acyclovir", Journal of Pharmaceutical Science, (Mar. 2001), vol. 90, No. 3, pp. 288-297.
Fu et al., "New polymeric carriers for controlled drug delivery following inhalation or injection", Biomaterials, (2002), vol. 23, pp. 4425-4433.
Giannavola et al., "Influence of Preparation Conditions on Acyclovir-Loaded Poly-d,I-Lactic Acid Nanospheres and Effect of PEG Coating on Ocular Drug Bioavailability", Pharmaceutical Research, (Apr. 2003), vol. 20, No. 4, pp. 584-590.
Giunchedi et al., "Emulsion Spray-Drying for the Preparation of Albumin-Loaded PLGA Microspheres", Drug Development and Industrial Pharmacy, (2001), vol. 27, No. 7, pp. 745-750.
Hida et al., "Common Gene Therapy Viral Vectors Do Not Efficiently Penetrate Sputum from Cystic Fibrosis Patients", PLoS ONE, (May 2011), vol. 6, Issue 5, pp. 1-6.
Huang et al., "Molecular aspects of muco- and bioadhesion: Tethered structures and site-specific surfaces", Journal of Controlled Release, (2000), vol. 65, pp. 63-71.
Jachak et al., "Transport of metal oxide nanoparticles and single walled carbon nanotubes in human mucus", Nanotoxicology, (Sep. 2012), vol. 6, No. 6, pp. 614-622.
Jang et al., "The structural basis for DNA binding by an anti-DNA autoantibody", Molecular Immunology, (1998), vol. 35, pp. 1207-1217.
Jiang et al., "Pulsatile protein release from a laminated device comprising of polyanhydrides and pH-sensitive complexes", International Journal of Pharmaceutics, (2000), vol. 194, pp. 51-60.
Jiang et al., Preparation, characterization and degradation characteristics of polyanhydrides contained poly(ethylene glycol), Polymer International, (1999), vol. 48, pp. 47-52.

Kim et al., "Use of Single-Site-Functionalized PEG Dendrons To Prepare Gene Vectors that Penetrate Human Mucus Barriers", Angewandte Chemie International Edition, (2013), vol. 52, pp. 3985-3988.
Kim et al., "Comparison of the pharmacokinetic profiles of two locally administered doxycycline gels in crevicular fluid and saliva", Journal of Clinical Periodontology, (2004), vol. 31, pp. 286-292.
Knowles et al., "Mucus clearance as primary innate defense mechanism for mammalian airways", The Journal of Clinical Investigation, (Mar. 2002), vol. 109, No. 5, pp. 571-577.
Kobayashi et al., "Tryptophan H33 plays an important role in pyrimidine (6-4) pyrimidone photoproduct binding by a high-affinity antibody", Protein Engineering, (1999), vol. 12, No. 10, pp. 879-884.
Lai et al., "Micro- and macrorheology of mucus", Advanced Drug Delivery Reviews, (2009), vol. 61, pp. 86-100.
Wang et al. "Preparation, characterization of paclitaxel-loaded Pluronic P105 polymeric micelles and in vitro reversal of multidrug resistant tumor." Acta Pharmaceutica Sincia 43:640-646, 2008.
Lai et al., "Mucus-penetrating nanoparticles for drug and gene delivery to mucosal tissues", Adv. Drug Deliv. Rev., (Feb. 27, 2009), vol. 61, No. 2, 36 pages.
Lai et al., "Drug carrier nanoparticles that penetrate human chronic rhinosinusitis mucus", Biomaterials, (2011), vol. 32, pp. 6285-6290.
Lai et al., "Altering Mucus Rheology to "Solidify" Human Mucus at the Nanoscale", PLoS ONE, (Jan. 2009), vol. 4, Issue 1, pp. 1-6.
Lai et al., "Rapid transport of large polymeric nanoparticles in fresh undiluted human mucus", PNAS, (Jan. 30, 2007), vol. 104, No. 5, pp. 1482-1487.
Lai et al., "Nanoparticles reveal that human cervicovaginal mucus is riddled with pores larger than viruses", PNAS, (Jan. 12, 2010), vol. 107, No. 2, pp. 598-603.
Lipman et al., "Monoclonal Versus Polyclonal Antibodies: Distinguishing Characteristics, Applications, and Information Resources", ILAR Journal, (2005), vol. 46, No. 3, pp. 258-268.
Lo et al., "Formulation design and pharmaceutical development of a novel controlled release form of azithromycin for single-dose therapy", Drug Development and Industrial Pharmacy, (2009), vol. 35, No. 12, pp. 1522-1529.
Qiu et al., "Compatibility and degradation of new polyphosphazene/polyanhydride blend", CAPLUS, (2001), No. 5, Abstract Only.
Abelson et al., "Loteprednol Etabonate in the Management of Dry Eye Inflammation", Refractive eyecare for ophthalmologists, (Nov. 2000), vol. 4, No. 11, pp. 4-7.
Mert et al., "A poly(ethylene glycol)-based surfactant for formulation of drug-loaded mucus penetrating particles", Journal of Controlled Release, (2012), vol. 157, pp. 455-460.
Mu et al., "Vitamin E TPGS used as emulsifier in the solvent evaporation/extraction technique for fabrication of polymeric nanospheres for controlled release of paclitaxel (Taxol®)", Journal of Controlled Release, (2002), vol. 80, pp. 129-144.
Nance et al., "A Dense Poly(Ethylene Glycol) Coating Improves Penetration of Large Polymeric Nanoparticles Within Brain Tissue", Science Translational Medicine, (Aug. 29, 2012), vol. 4, Issue 149, pp. 1-8.
Newman et al., "Uptake of poly(D,L-lactic-co-glycolic acid) microspheres by antigen-presenting cells in vivo", Journal of Biomedical Materials Research, (Jun. 5, 2002), vol. 60, Issue 3, pp. 480-486.
Norris et al., "Effect of Size, Surface Charge, and Hydrophobicity on the Translocation of Polystyrene microspheres Through Gastrointestinal Mucin", Journal of Applied Polymer Science, (Mar. 14, 1997), vol. 63, Issue 11, pp. 1481-1492.
Norris et al., "The Uptake and Translocation of Microparticles through GI Mucin", Pharma. Res., (1995), vol. 12, pp. S233 abstract only.
Peppas et al., "Ultrapure poly(vinyl alcohol) hydrogels with mucoadhesive drug delivery characteristics", European Journal of Pharmaceutics and Biopharmaceutics, (1997), vol. 43, pp. 51-58.
Peppas et al., "Poly(ethylene glycol)-containing hydrogels in drug delivery", Journal of Controlled Release, (1999), vol. 62, pp. 81-87.

(56) References Cited

OTHER PUBLICATIONS

Peracchia et al., "PEG-coated nanospheres from amphiphilic diblock and multiblock copolymers: Investigation of their drug encapsulation and release characteristics", Journal of Controlled Release, (1997), vol. 46, pp. 223-231.
Perry, "Sorbent Materials and Sorption-Process Analysis", Perry's Chemical Engineers' Handbook, (1984), vol. 6, pp. 16-5-16-6.
Pillai et al., "Polymers in drug delivery", Current Opinion in Chemical Biology, (2001), vol. 5, pp. 447-451.
Prasad et al., "Confocal microscopy of colloids", Journal of Physics Condensed Matter, (2007), vol. 19, pp. 1-25.
Prego et al., "The potential of chitosan for the oral administration of peptides", Expert Opinion Drug Deliver, (2005), vol. 2, No. 5, pp. 843-854.
Pui, "Rasburicase: a potent uricolytic agent", Expert Opin. Pharmacother., (2002), vol. 3, No. 4, pp. 433-452.
Qiu et al., "Design of a core-shelled polymer cylinder for potential programmable drug delivery", International Journal of Pharmaceutics, (2001), vol. 219, pp. 151-160.
Rodeheaver et al., "Pluronic F-68: A Promising New Skin Wound Cleanser", Ann Emerg Med, (Nov. 1980), vol. 9, No. 11, pp. 572-576.
Rolland et al., "Direct Fabrication and Harvesting of Monodisperse, Shape-Specific Nanobiomaterials", J. Am. Chem. Soc., (2005), vol. 127, No. 28, pp. 10096-10100.
Schuster et al., "Nanoparticle diffusion in respiratory mucus from humans without lung disease", Biomaterials, (2013), vol. 34, pp. 3439-3446.
Serra et al., "Engineering Design and Molecular Dynamics of Mucoadhesive Drug Delivery Systems as Targeting Agents", Eur. J. Pharm. Biopharm., (Mar. 2009), vol. 71, No. 3, 24 pages.
Serra et al., "Design of poly(ethylene glycol)-tethered copolymers as novel mucoadhesive drug delivery systems", European Journal of Pharmaceutics and Biopharmaceutics, (2006), vol. 63, pp. 11-18.
Shakesheff et al., "The Adsorption of Poly(vinyl alcohol) to Biodegradable Microparticles Studied by X-Ray Photoelectron Spectroscopy (XPS)", Journal of Colloid and Interface Science, (1997), vol. 185, pp. 538-547.
Singh et al., "Cationic microparticles: A potent delivery system for DNA vaccines", PNAS, (Jan. 18, 2000), vol. 97, No. 2, pp. 811-816.
Singla et al., "Paclitaxel and its formulations", International Journal of Pharmaceutics, (2002), vol. 235, pp. 179-192.
Suh et al., "Real-time multiple-particle tracking: applications to drug and gene delivery", Advanced Drug Delivery Reviews, (2005), vol. 57, pp. 63-78.
Suh et al., "PEGylation of nanoparticles improves their cytoplasmic transport", International Journal of Nanomedicine, (2007), vol. 2, No. 4, pp. 735-741.
Suk et al., "The penetration of fresh undiluted sputum expectorated by cystic fibrosis patients by non-adhesive polymer nanoparticles", Biomaterials, (2009), vol. 30, pp. 2591-2597.
Suk et al., "N-acetylcysteine Enhances Cystic Fibrosis Sputum Penetration and Airway Gene Transfer by Highly Compacted DNA Nanoparticles", Molecular Therapy, (Nov. 2011), vol. 19, No. 11, pp. 1981-1989.
Suk et al., "Rabid transport of muco-inert nanoparticles in cystic fibrosis sputum treated with N-acetyl cysteine", Nanomedicine, (2011), vol. 6, No. 2, pp. 365-375.
Tang et al., "Biodegradable polymer nanoparticles that rapidly penetrate the human mucus barrier", PNAS, (Nov. 17, 2009), vol. 106, No. 46, pp. 19268-19273.
Vila et al., "Transport of PLA-PEG particles across the nasal mucosa: effect of particle size and PEG coating density", Journal of Controlled Release, (2004), vol. 98, pp. 231-244.
Whaley et al., "Novel Approaches to Vaginal Delivery and Safety of Microbicides: Biopharmaceuticals, Nanoparticles, and Vaccines", Antiviral Research, (2010), vol. 885, pp. S55-S66.
Wang et al., "Mucoadhesive Nanoparticles May Disrupt the Protective Human Mucus Barrier by Altering its Microstructure", PLoS ONE, (Jun. 2011), vol. 6, Issue 6, pp. 1-7.
Wang et al., "Addressing the PEG Mucoadhesivity Paradox to Engineer Nanoparticles that "Slip" through the Human Mucus Barrier", Angew. Chem. Int. Ed., (2008), vol. 47, pp. 1-5.
Wu et al., "Novel Nanoparticles Formed via Self-Assembly of Poly(ethylene glycol-b-sebacic anhydride) and Their Degradation in Water", Macromolecules, (2000), vol. 33, pp. 9040-9043.
Xu et al., "Nanoparticle diffusion in, and microrheology of, the bovine vitreous ex vivo", Journal of Controlled Release, (2013), vol. 167, pp. 76-84.
Xu et al., "Scalable method to produce biodegradable nanoparticles that rapidly penetrate human mucus", Journal of Controlled Release, (2013), vol. 170, pp. 279-286.
Yang et al., "Biodegradable Nanoparticles Composed Entirely of Safe Materials that Rapible Penetrate Human Mucus", Angew. Chem. Int. Ed., (2011), vol. 50, pp. 2597-2600.
Yoncheva et al., "Bioadhesive properties of pegylated nanoparticles", Expert Opin. Drug Deliv., (2005), vol. 2, No. 2, pp. 205-218.
Yoncheva et al., "Evaluation of bioadhesive potential and intestinal transport of pegylated poly(anhydride) nanoparticles", International Journal of Pharmaceutics, (2007), vol. 334, pp. 156-165.
Yoo et al., "Biodegradable Nanoparticles Containing Doxorubicin-PLGA Conjugate for Sustained Release", Pharmaceutical Research, (1999), vol. 16, No. 7, pp. 1114-1118.
Yu et al., "Biodegradable mucus-penetrating nanoparticles composed of diblock copolymers of polyethylene glycol and poly(lactic-co-glycolic acid)", Drug Deliv. and Transl. Res., (2012), vol. 2, pp. 124-128.
Declaration of Dr. Alexey Popov executed Feb. 21, 2013 with Curriculum vitae.
Shuai et al., "Synthesis and characterization of several degradable aliphatic polyanhydrides", Journal of Beijing Institute of Technology (English Edition), (1996), vol. 5, No. 2, pp. 130-136 abstract only.
Webster's Ninth New Collegiate Dictionary, (1988), pp. 58.
International Search Report (Form PCT/ISA/210) dated Mar. 12, 2008, by the International Bureau of WIPO in corresponding International Patent Application No. PCT/US2007/019522. (5 pages).
Hancock et al., "What is the True Solubility Advantage for Amorphous Pharmaceuticals?", Pharmaceutical Research, (Nov. 4, 2000), vol. 17, No. 4, pp. 397-404.
"Lutrol® L and Lutrol F-Grades", Pharma Ingredients & Services, (Apr. 2010), 8 pages.
Kapin et al., "Inflammation-Mediated Retinal Edema in the Rabbit Is Inhibited by Topical Nepafenac", Inflammation, (Oct. 2003), vol. 27, No. 5, pp. 281-291.
Lin et al., "Carbopol.pluronic phase change solutions for ophthalmic drug delivery", Journal of Controlled Release, (2000), vol. 69, pp. 379-388.
Alexandridis, "Poly(ethylene oxide)/poly(propylene oxide) block copolymer surfactants", Current Opinion in Colloid & Interface Science, (Oct. 1997), vol. 2, Issue 5, pp. 478-489.
Yamagata et al., Improvement of the Oral Drug Absorption of Topotecan through the Inhibition of Intestinal Xenobiotic Efflux Transporter, Breast Cancer Resistance Protein, by Excipients, 35(7) Drug Metabolism and Disposition 1142-1148 (2007).
International Search Report dated Oct. 17, 2013, in PCT/US2013/039540.
International Search Report dated Aug. 26, 2013, in PCT/US2013/039499.
Cholkar K et al. "Novel strategies for anterior segment ocular drug delivery" J Ocul Pharmacol Ther, 29:106-123, 2013.
Gaudana R et al. "Ocular drug delivery" AAPS J, 12:348-360, 2010.
Molokhia SA et al. "Anterior eye segment drug delivery systems: current treatments and future challenges" J Ocul Pharmacol Ther, 29:92-104, 2013.
Patel PB et al. "Ophthalmic drug delivery systems: challenges and approaches" Syst Rev Pharm, 1:113-120, 2010.
Singh V et al. "The challenges of ophthalmic drug delivery: a review" Int J Drug Discovery, 3:56-62, 2011.
Mura S et al. "Biodegradable Nanoparticles Meet the Bronchial Airway Barrier: How Surface Properties Affect Their Interaction with Mucus and Epithelial Cells" Biomacromolecues 12:4136-4143, 2011.

(56) References Cited

OTHER PUBLICATIONS

Garg et al. "Mucoadhesive microspheres: a short review" Asian J Pharma Clin Res 5:24-27, 2012.
Danhier et al. "PLGA-based nanoparticles: An overview of biomedical applications" J Controlled Rel 161:505-522, 2012.
Corrigan et al. "Quantifying drug release from PLGA nanoparticles" Eur J Pharma Sci 37:477-485, 2009.
Xie et al. "PLGA Nanoparticles Improve the Oral Bioavailability of Curcumin in Rats: Characterizations and Mechanisms" J Agric Food Chem 59:9280-9289, 2011.
Sigurdsson HH et al. "Mucus as a barrier to lipophilic drugs" Int J Pharmaceutics 453:56-64, 2013.
U.S. Appl. No. 13/886,514, filed May 3, 2013, Compositions and methods utilizing poly(vinyl alcohol) and/or other polymers that aid particle transport in mucus.
U.S. Appl. No. 13/886,493, filed May 3, 2013, Nanocrystals, Compositions, and Methods That Aid Particle Transport in Mucus.
U.S. Appl. No. 14/731,921, filed Jun. 5, 2015, Nanocrystals, Compositions, and Methods That Aid Particle Transport in Mucus.
U.S. Appl. No. 14/731,972, filed Jun. 5, 2016, Nanocrystals, Compositions, and Methods That Aid Particle Transport in Mucus.
U.S. Appl. No. 13/886,602, filed May 3, 2013, Particles, Compositions, and Methods for Ophthalmic and/or Other Applications.
U.S. Appl. No. 13/886,658, filed May 3, 2013, Particles, Compositions, and Methods for Ophthalmic and/or Other Applications.
U.S. Appl. No. 15/187,552, filed Jun. 20, 2016, Nanocrystals, Compositions, and Methods That Aid Particle Transport in Mucus.
U.S. Appl. No. 15/354,704, filed Nov. 17, 2016, Nanocrystals, Compositions, and Methods That Aid Particle Transport in Mucus.
U.S. Appl. No. 15/616,799, filed Jun. 7, 2017, Nanocrystals, Compositions, and Methods That Aid Particle Transport in Mucus.
U.S. Appl. No. 15/976,736, filed May 10, 2018, Nanocrystals, Compositions, and Methods That Aid Particle Transport in Mucus.
U.S. Appl. No. 15/992,494, filed May 30, 2018, Particles, Compositions, and Methods for Ophthalmic and/or Other Applications.
Yang M. et al. "Production of virus-mimetic mucus-penetrating particles for drug and gene delivery in mucosal tissues." 2008 Annual Meeting of AIChE Nanoscale Science and Engineering Forum, Nov. 16-21, 2008, Abstract 705b.
Ludwig A "The use of mucoadhesive polymers in ocular drug delivery." Adv Drug Deliv Rev 57:1595-1639, 2005.
Memon A. et al. "Optimization of formulation parameters on ocular loteprednol etabonate nanosuspension by media milling method." Int J Pharmaceut Biol Arch 4:46-51, 2012.
Sahib MN et al. "Solubilization of beclomethasone dipropionate in sterically stabilized phospholipid nanomicelles (SSMs): physicochemical and in vitro evaluations." Drug Des Devel Ther 6:29-42, 2012.
Popov A et al. "Mucus-penetrating nanoparticles made with "mucoadhesive" poly(vinyl alcohol)." Nanomedicine: Nanotech Bio Med. 12:1863-1871, 2016.
Bouazza, N.; et al. "Population Pharmacokinetics of Tenofovir in HIV-1-infected Pediatric Patients" J. Acquire Immune Defic Syndr. 2011, 58 (3), 283-288.
Bourganis et al . . . European Journal of Pharmaceutics and Biopharmaceutics, 97: 239-249 (Year: 2015).
Jones et al., Journal of Pharmaceutical Sciences, 95: 1060-1074 (Year: 2006).
Lai et al., Journal of Virology, 83: 11196-11200 (Year: 2009).
Lieleg et al., Biophysical Journal, 98: 1782-1789 (Year: 2010).
Popov A et al. "Mucosal-penetrating particles enable topical delivery to posterior segment of the eye" Controlled Release Soc Ann Mtg Jul. 21-24, 2013.
Popov A et al. "Mucus-penetrating Particles for Enhanced Ophthalmic Delivery" American Association of Pharmaceutical Scientists Annual Meeting, Nov. 11-13, 2013.
Saito et al. "Pluronic Surfactants" J Japan Oil Chemists Society 49:1071-1080, 2000.
Schopf et al. "Enhanced topical delivery of a small molecule receptor tyrosine kinase inhibitor (RTKi) via mucosal-penetrating particle technology." Assoc Res in Vision Ophthamol May 5-9, 2013.
Schopf et al. "Long-acting mucus-penetrating particles exhibit improved duration of action in a lung inflammation model" 17th Int Conf of the Inflammation Res Assoc Aug. 29, 2012, Suppl 2, vol. 57, 2012.
Schopf et al. "Long-acting mucus-penetrating particles exhibit improved duration of action in a lung inflammation model" Inflammation Research, 61 (Suppl 1) Published online Aug. 14, 2012.
Vandervoort et al., European Journal of Pharmaceutics and Biopharmaceutic, 57: 251-261 (Year: 2004).
Witvrouw, M.; et al. "Susceptibility of HIV-2, SIV and SHIV to various anti-HIV-1 compounds: implications for treatment and postexposure prophylaxis" Antiviral Therapy 2004, 9, 57-65.
Zou et al., "New approach for local delivery of rapamycin by bioadhesive PLGA-carbopol nanoparticles" Drug Delivery, 16: 15-23, 2009.
International Preliminary Report on Patentability of PCT/US2005/002556 (WO2005/072710).
International Preliminary Report on Patentability of PCT/US2008/019522 (WO2008/030557).
International Preliminary Report on Patentability of PCT/US2011/059321 (WO2012/061703).
International Preliminary Report on Patentability of PCT/US2011/051195 (WO2012/039979).
International Preliminary Report on Patentability of PCT/US2012/024344 (WO2012/0109363).
International Preliminary Report on Patentability of PCT/US2012/069882 (WO2013/090804).
International Preliminary Report on Patentability of PCT/US2013/022387 (WO2013/110028).
International Preliminary Report on Patentability of PCT/US2013/039731 (WO2013/166498).
International Preliminary Report on Patentability of PCT/US2011/026321 (WO2011/106702).
International Preliminary Report on Patentability of PCT/US2013/039499 (WO2013/166408).
International Preliminary Report on Patentability of PCT/US2013/039467 (WO2013/166385).
International Preliminary Report on Patentability of PCT/US2013/039540 (WO2013/166436).
International Preliminary Report on Patentability of PCT/US2014/063373 (WO2015/066444).

COMPOSITIONS AND METHODS UTILIZING POLY(VINYL ALCOHOL) AND/OR OTHER POLYMERS THAT AID PARTICLE TRANSPORT IN MUCUS

RELATED APPLICATIONS

The present application is a division of U.S. patent application Ser. No. 13/886,514 filed May 3, 2013, now U.S. Pat. No. 10,668,041, which claims priority under 35 U.S.C. § 119(e) to U.S. Provisional Patent Application No. 61/642,261, filed May 3, 2012, and entitled "Compositions and Methods Utilizing Poly(Vinyl Alcohol) and/or Other Polymers that Aid Particle Transport in Mucus", both of which are incorporated herein by reference in their entirety.

FIELD OF THE INVENTION

The present invention generally relates to particles, compositions, and methods that aid particle transport in mucus.

BACKGROUND OF THE INVENTION

A mucus layer present at various points of entry into the body, including the eyes, nose, lungs, gastrointestinal tract, and female reproductive tract, is naturally adhesive and serves to protect the body against pathogens, allergens, and debris by effectively trapping and quickly removing them via mucus turnover. For effective delivery of therapeutic, diagnostic, or imaging particles via mucus membranes, the particles must be able to readily penetrate the mucus layer to avoid mucus adhesion and rapid mucus clearance. Several lines of evidence suggest that conventional nanoparticles are not capable of crossing mucosal barriers. However, it has been recently demonstrated that polymeric nanoparticles (degradable or not) modified with a special surface coating (covalently or non-covalently) can diffuse in physiologically think mucus samples nearly as rapidly as they would in water. Such polymer-based mucus-penetrating particles (MPP) can encapsulate various therapeutic, imaging, or diagnostic agents to enable drug delivery, diagnostic, or imaging applications.

Despite these improvements, only a handful of surface coatings have been shown to facilitate mucus penetration of particles. Accordingly, improvements in compositions and methods involving mucus-penetrating particles for delivery of pharmaceutical agents would be beneficial.

SUMMARY OF THE INVENTION

The present description generally relates to particles, compositions, and methods that aid particle transport in mucus. In some embodiments, the compositions and methods include a synthetic polymer having pendant hydroxyl groups on the backbone of the polymer (e.g., poly(vinyl alcohol), PVA), which facilitates mucus penetration. The subject matter of this application involves, in some cases, interrelated products, alternative solutions to a particular problem, and/or a plurality of different uses of structures and compositions.

In one set of embodiments, a method of forming coated particles is provided. The method comprises coating a plurality of core particles with a surface-altering agent to form coated particles, wherein the surface-altering agent comprises a synthetic polymer having pendant hydroxyl groups on the backbone of the polymer, the polymer having a molecular weight of at least about 1 kDa and less than or equal to about 1000 kDa, and wherein the polymer is at least about 30% hydrolyzed and less than about 95% hydrolyzed. Each of the core particles comprises a pharmaceutical agent or a salt thereof. The coated particles have a relative velocity of greater than 0.5 in mucus.

In another set of embodiments, a composition comprising a plurality of coated particles is provided. Each of the coated particles comprises a core particle comprising a pharmaceutical agent or a salt thereof and a coating comprising a surface-altering agent surrounding the core particle. The surface-altering agent comprises a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed. The coated particles have a relative velocity of greater than 0.5 in mucus.

In another set of embodiments, a method of treatment is provided. The method comprises administering to a patient or a subject in need thereof, a composition comprising a plurality of coated particles. Each of the coated particles comprises a core particle comprising a pharmaceutical agent or a salt thereof and a coating comprising a surface-altering agent surrounding the core particle. The surface-altering agent comprises a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed. The coated particles have a relative velocity of greater than 0.5 in mucus.

In another set of embodiments, a method is provided. The method comprises delivering to a mucus membrane a composition comprising a plurality of coated particles. The coated particle comprises a core particle comprising a pharmaceutical agent or a salt thereof, and a coating comprising a surface-altering agent surrounding the core particle. The surface-altering agent comprises a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, and wherein the coated particles have a relative velocity of greater than 0.5 in mucus.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

Figure 4A:
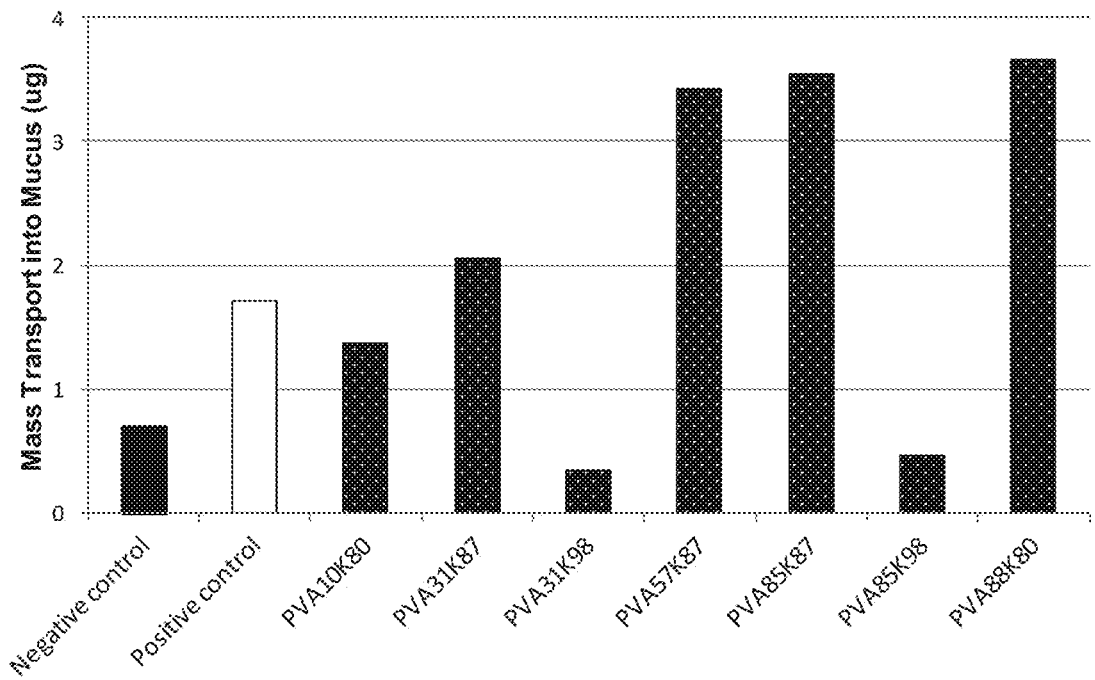
Figure 4B:
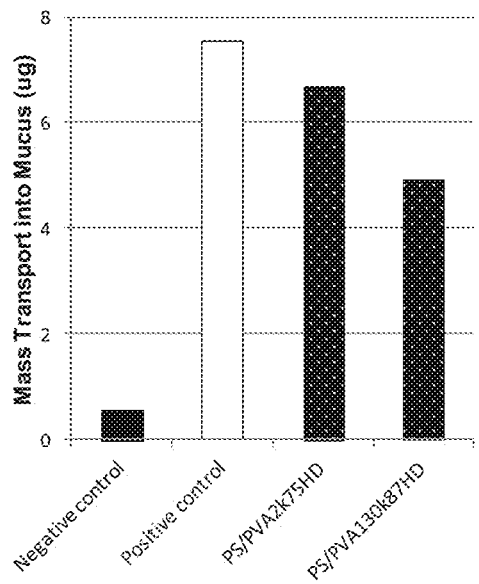
Figure 5A:
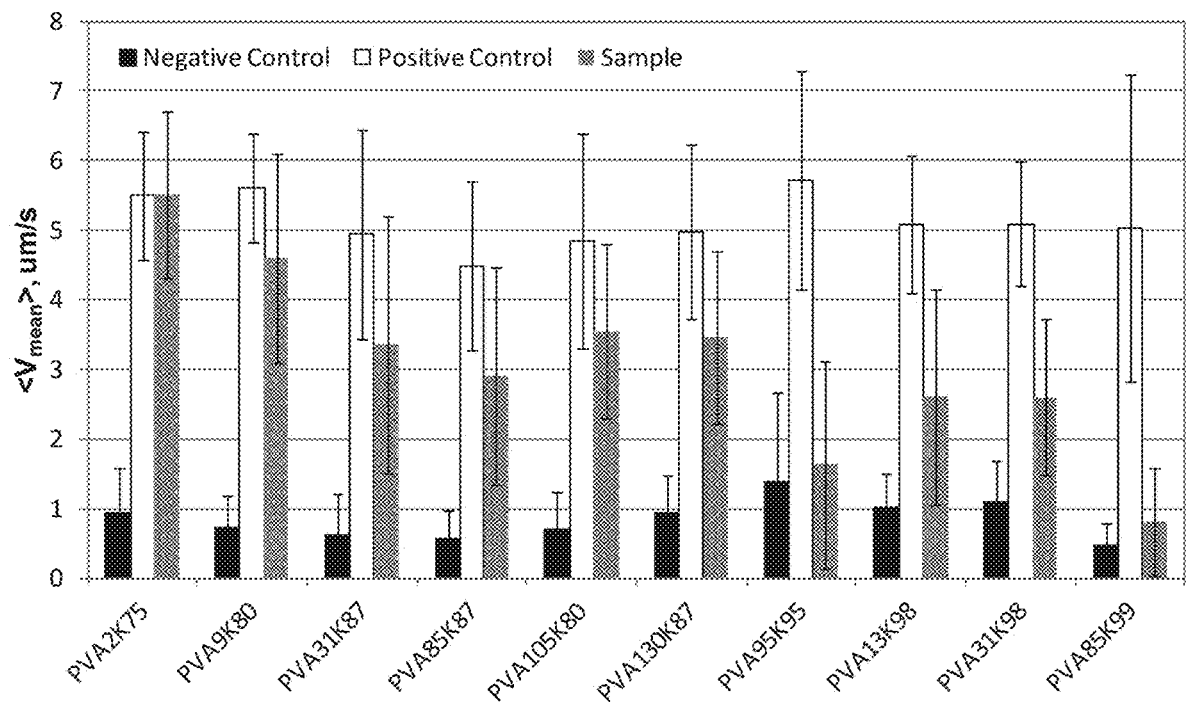
Figure 5B:
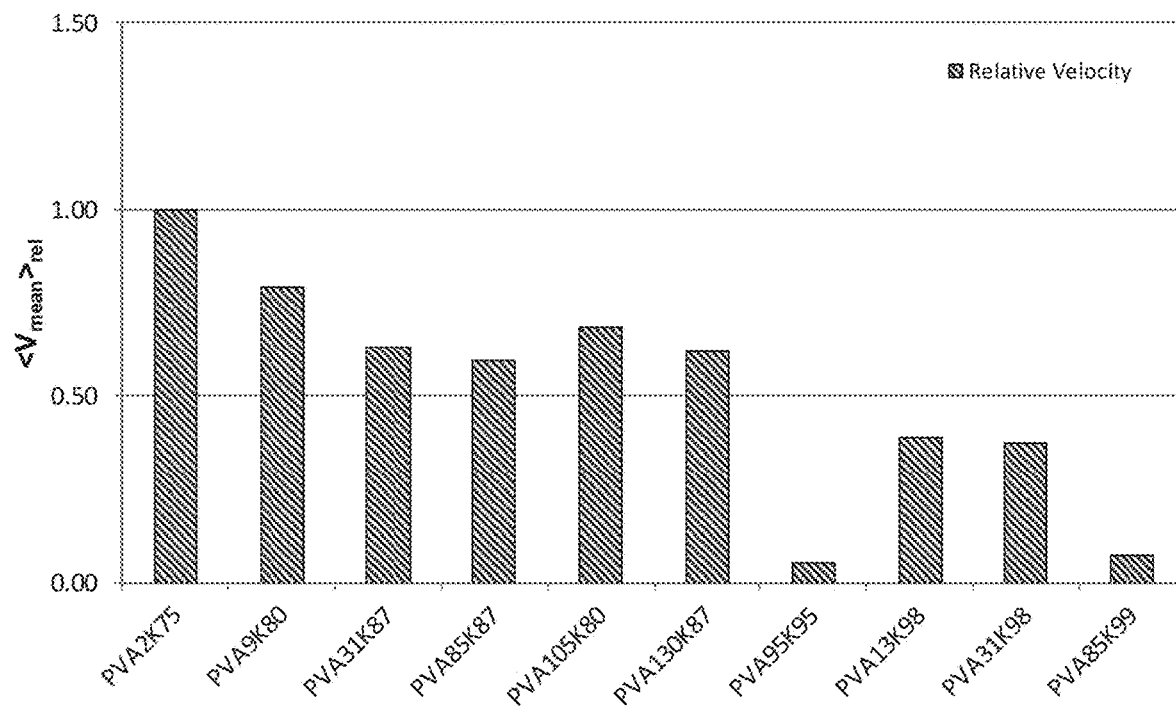
Figure 6:
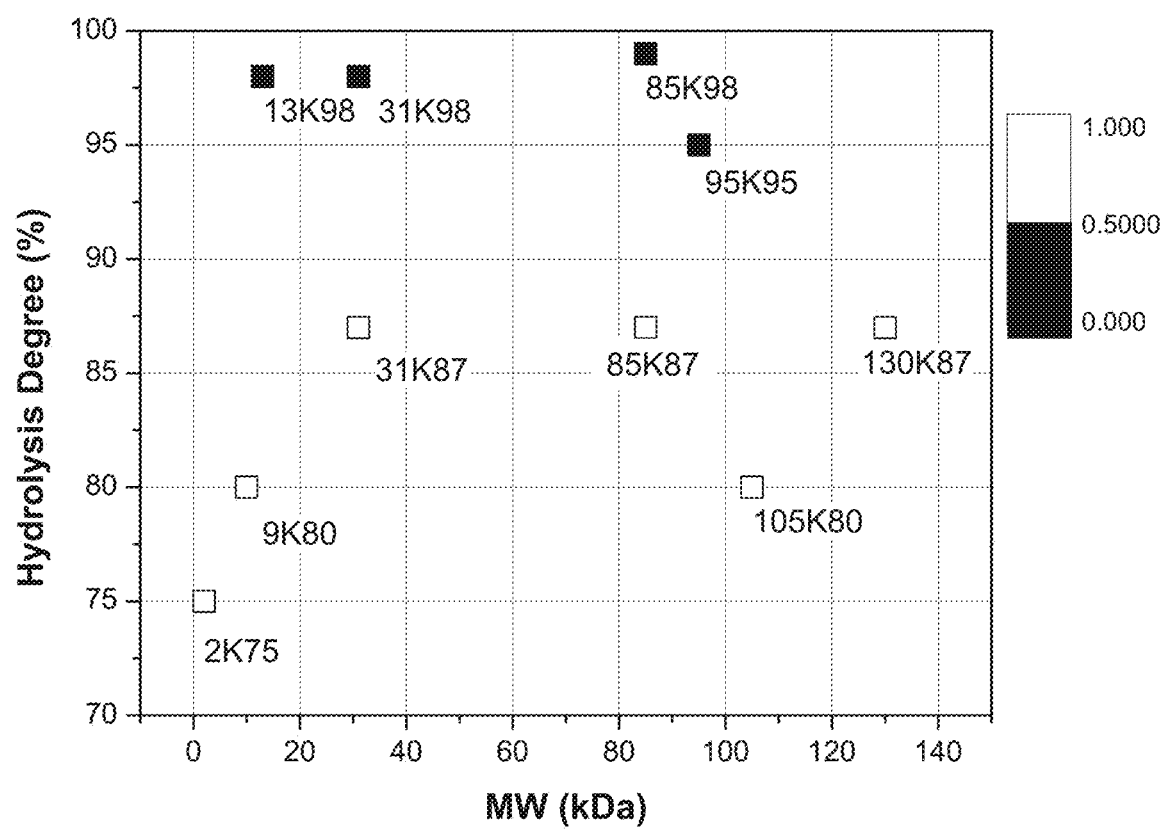
Figure 7A:
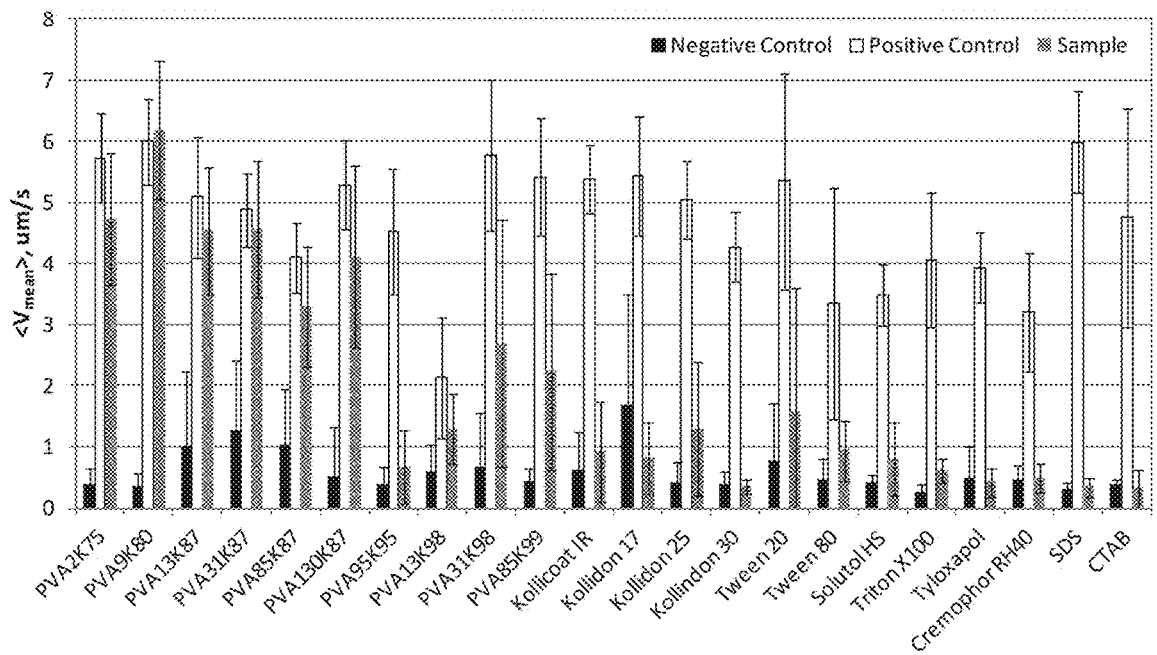
Figure 7B:
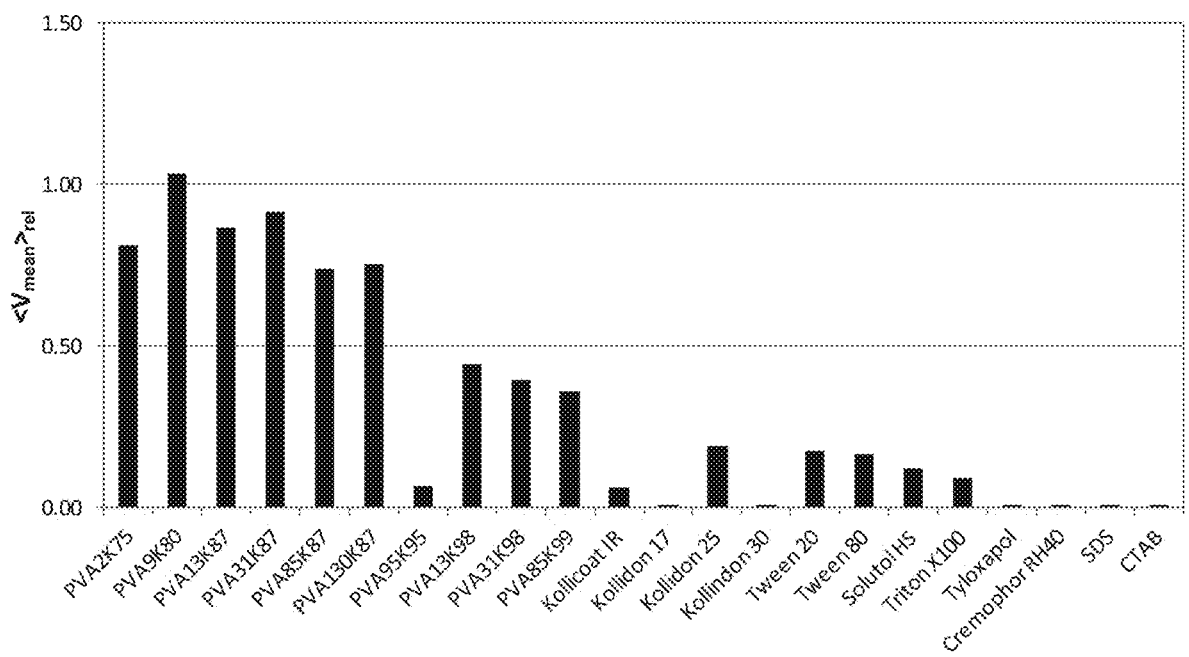
Figure 8A:
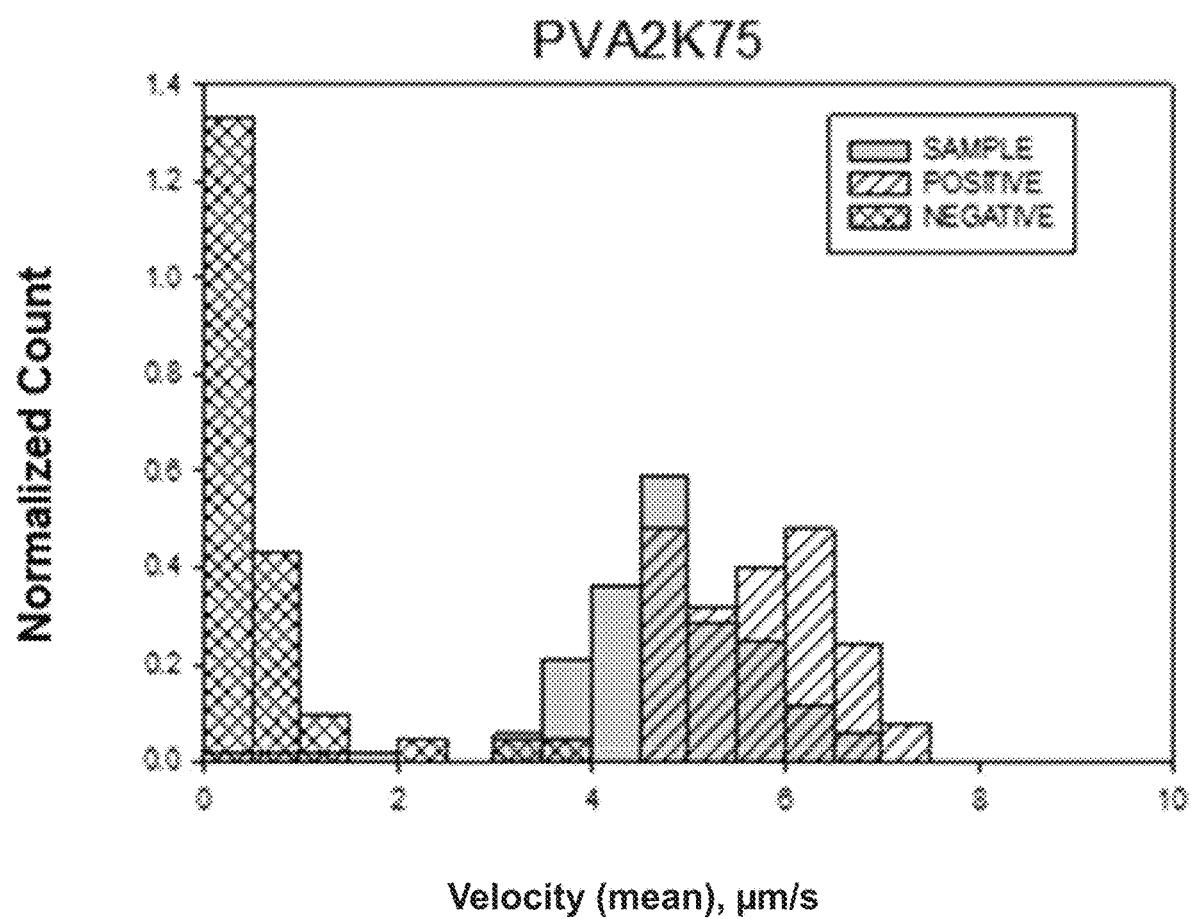
Figure 8B:
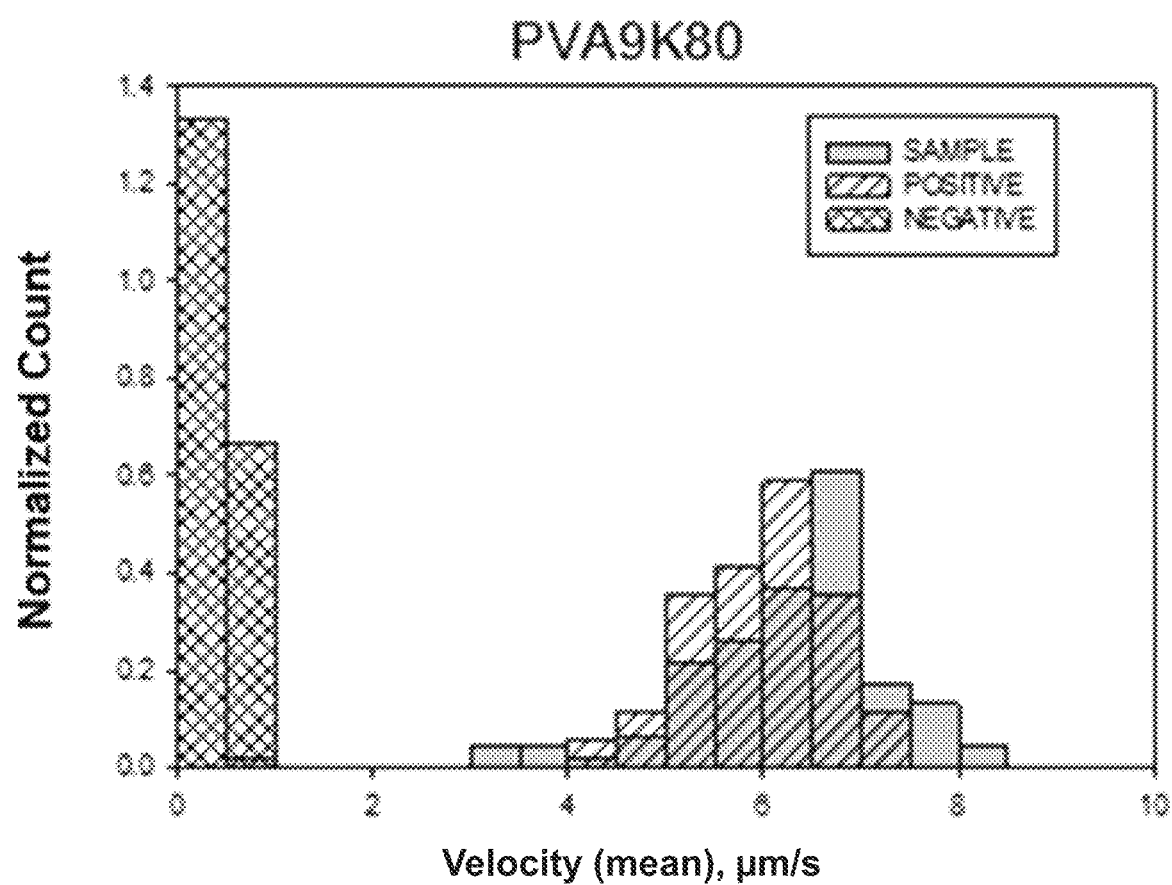
Figure 8C:
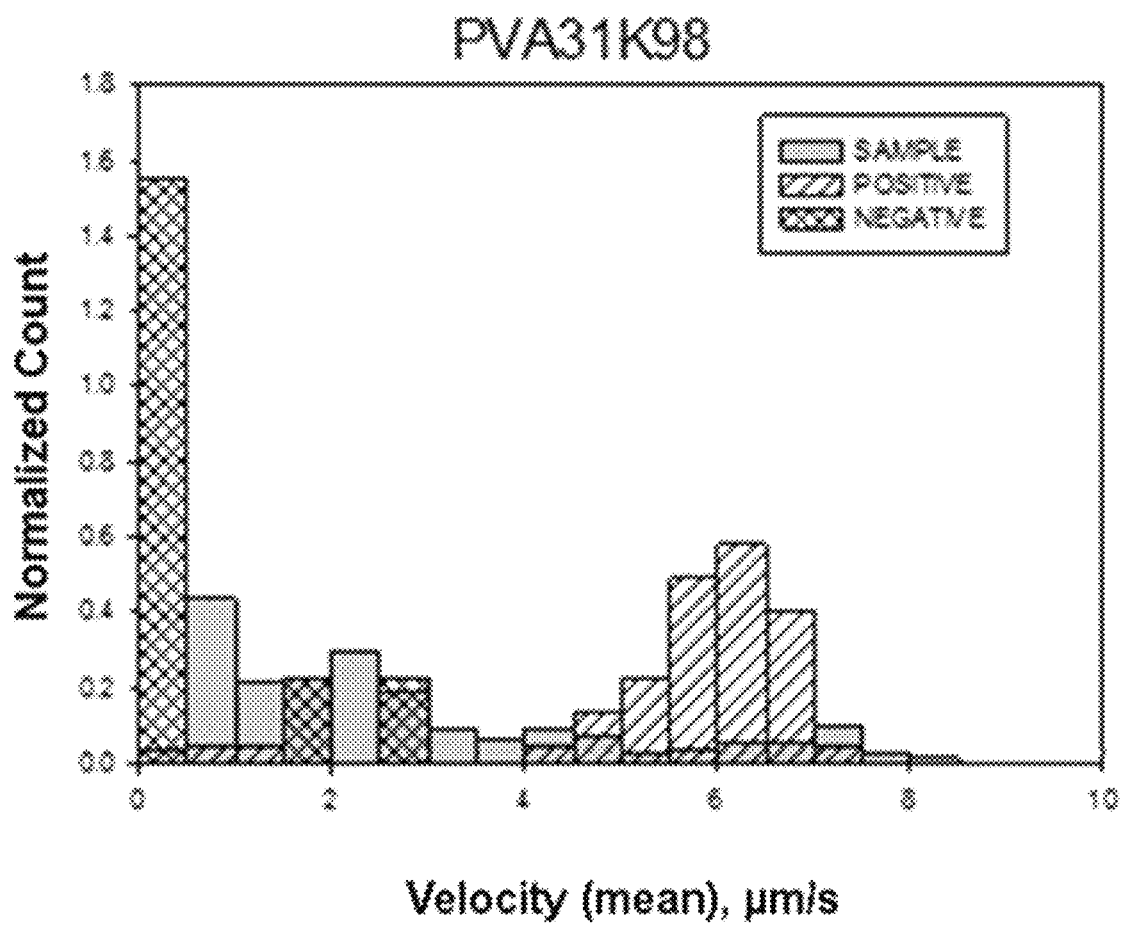
Figure 8D:
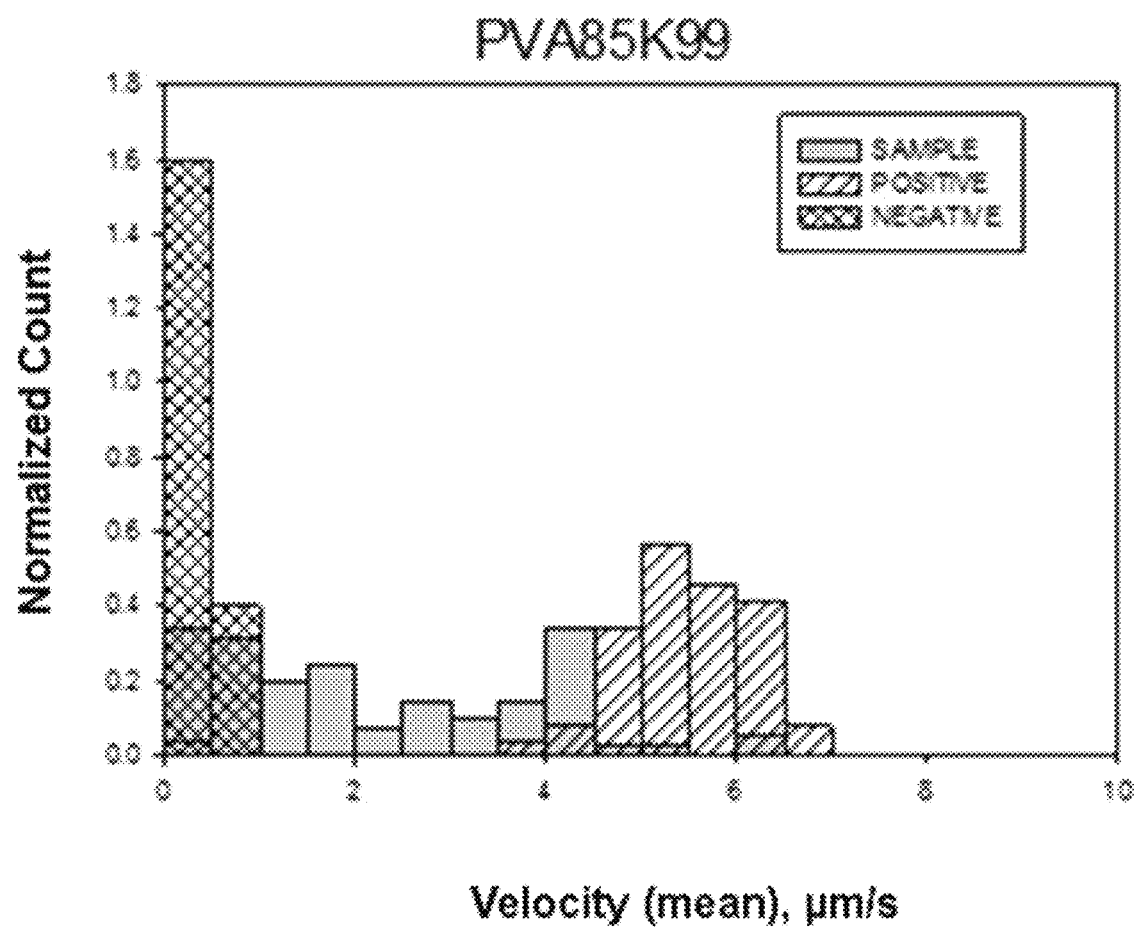
Figure 8E:
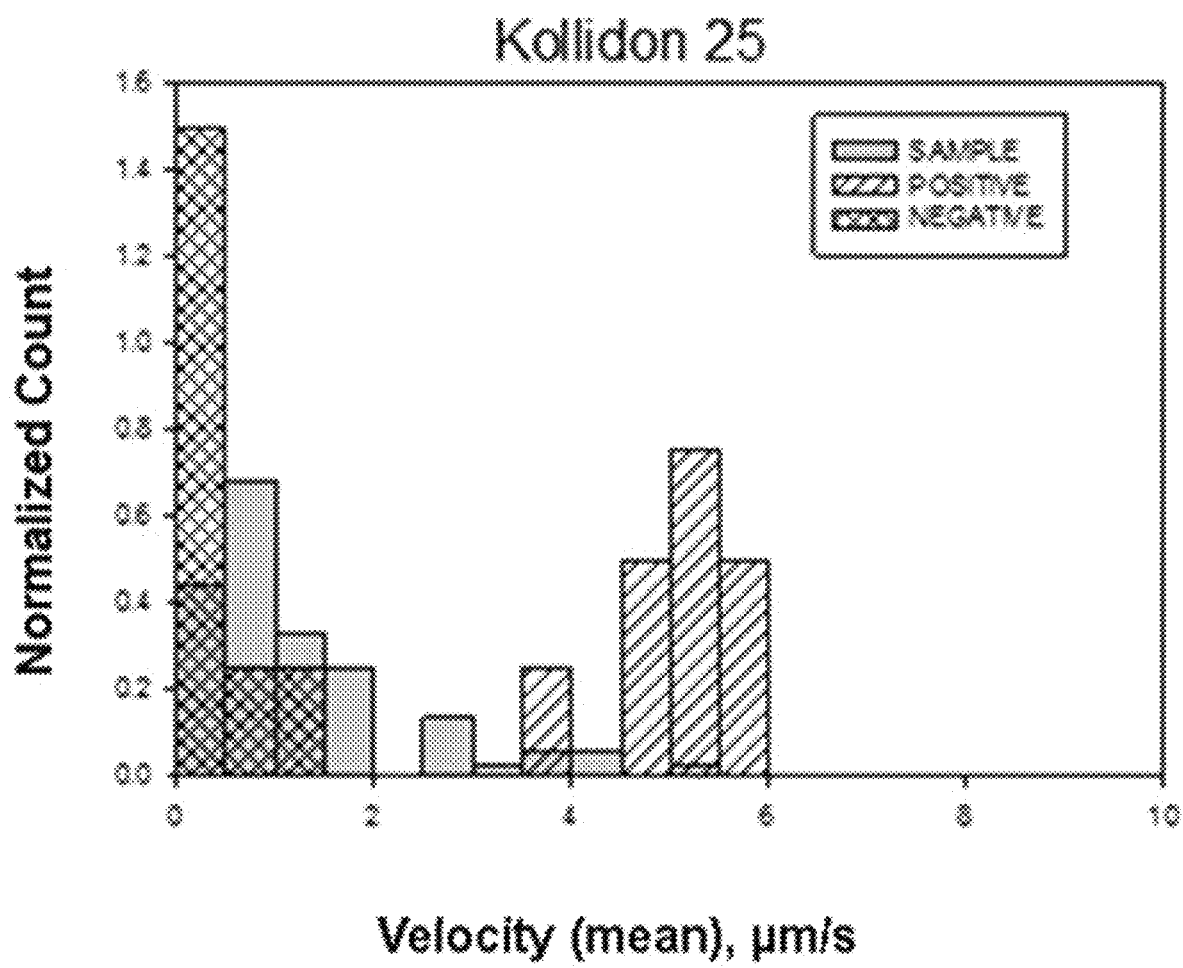
Figure 8F:
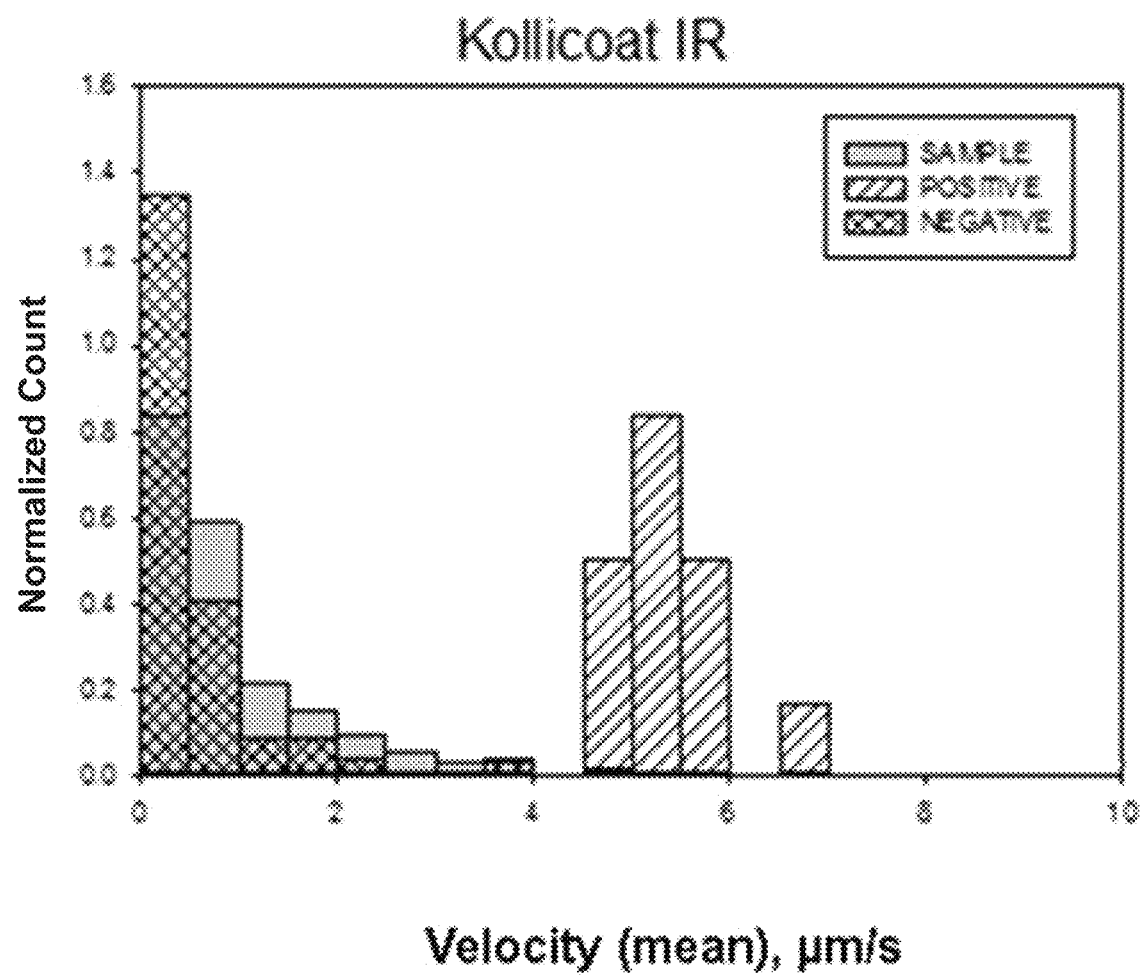
Figure 9:
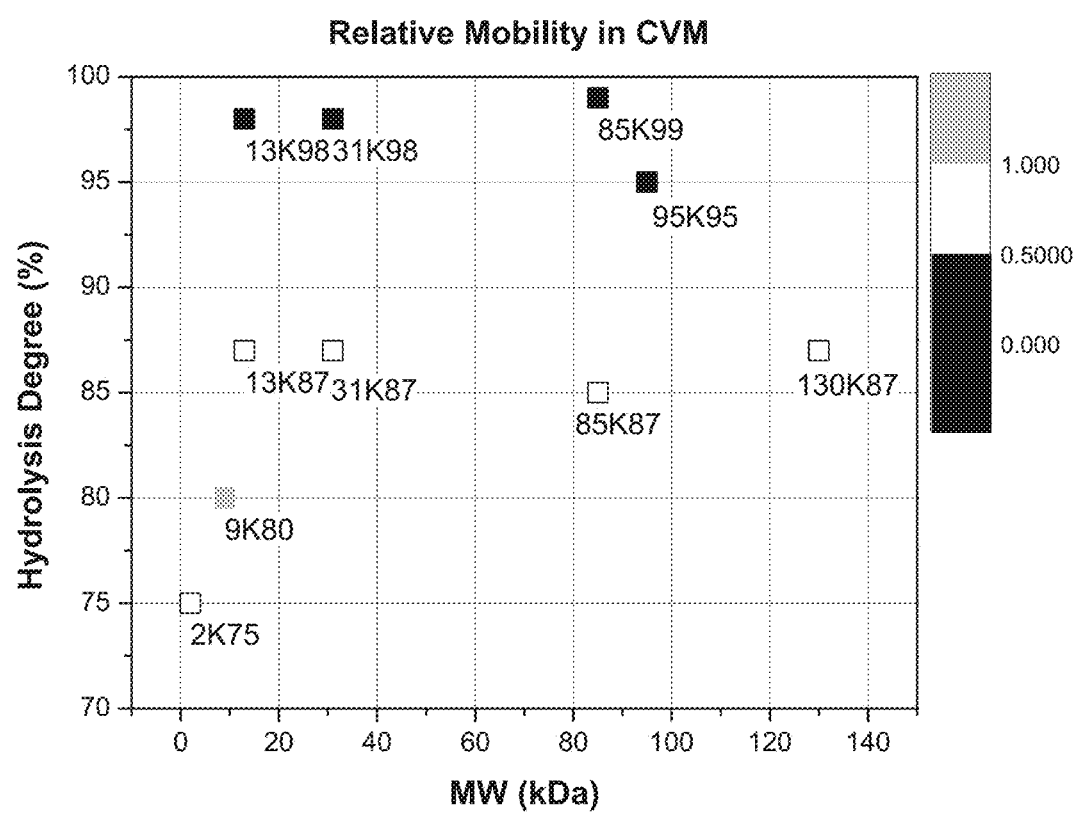

FIGS. 4A-4B are plots showing bulk transport in CVM in vitro of PSCOO nanoparticles coated with various PVAs, according to one set of embodiments. Negative controls are uncoated 200 nm PSCOO particles; Positive controls are 200 nm PSCOO particles coated with Pluronic® F127. FIGS. 4A-4B represent data obtained with two different CVM samples;

FIGS. 5A-5B are plots showing ensemble-average velocity $<V_{mean}>$ (FIG. 5A) and relative sample velocity $<V_{mean}>_{rel}$ (FIG. 5B) for poly(lactic acid) (PLA) nanoparticles (sample) prepared by emulsification with various PVAs as measured by multiple-particle tracking in CVM, according to one set of embodiments;

FIG. 6 is a plot showing relative velocity $<V_{mean}>_{rel}$ in CVM for PLA nanoparticles prepared by emulsification with various PVAs mapped according to the PVA's molecular weight and degree of hydrolysis, according to one set of embodiments. Each data point represents $<V_{mean}>_{rel}$ of the particles stabilized with a specific PVA. The "+" signs represent measurements in multiple CVM samples;

FIGS. 7A-7B are plots showing ensemble-average velocity $<V_{mean}>$ (FIG. 7A) and relative sample velocity $<V_{mean}>_{rel}$ (FIG. 7B) for pyrene nanoparticles (sample) and controls as measured by multiple-particle tracking in CVM, according to one set of embodiments;

FIGS. 8A-8F are representative CVM velocity ($V_{mean}$) distribution histograms for pyrene/nanocrystals obtained with various surface-altering agents (SAMPLE=Pyrene nanoparticles, POSITIVE=200 nm PS-PEG5K, NEGATIVE=200 nm PS-COO); according to one set of embodiments; and FIG. 9 is a plot of relative velocity $<V_{mean}>_{rel}$ for pyrene nanocrystals coated with PVA in CVM mapped according to the PVA's molecular weight and degree of hydrolysis according to one set of embodiments.

DETAILED DESCRIPTION

Particles, compositions, and methods that aid particle transport in mucus are provided. The compositions and methods may include, in some embodiments, modifying the surface coatings of particles including pharmaceutical agents that have a low water/aqueous solubility. In some embodiments, a surface coating includes a synthetic polymer having pendant hydroxyl groups on the backbone of the polymer, such as poly(vinyl alcohol) (PVA). Such compositions and methods can be used to achieve efficient transport of particles of pharmaceutical agents though mucus barriers in the body for a wide spectrum of applications, including drug delivery, imaging, and diagnostic applications. In certain embodiments, a pharmaceutical composition including such particles is well-suited for administration routes involving the particles passing through a mucosal barrier.

In some embodiments, the compositions and methods involve the use of PVAs that aids particle transport in mucus. The compositions and methods may involve making mucus-penetrating particles (MPP) by, for example, an emulsification process in the presence of specific PVAs. In certain embodiments, the compositions and methods involve making MPP from pre-fabricated particles by non-covalent coating with specific PVAs. In other embodiments, the compositions and methods involve making MPP in the presence of specific PVAs without any polymeric carriers, or with minimal use of polymeric carriers. It should be appreciated, however, that in other embodiments, polymeric carriers can be used.

PVA is a water-soluble non-ionic synthetic polymer. Due to its surface active properties, PVA is widely used in the food and drug industries as a stabilizing agent for emulsions and, in particular, to enable encapsulation of a wide variety of compounds by emulsification techniques. PVA has the "generally recognized as safe" or "GRAS" status with the Food and Drug Administration (FDA), and has been used in auricular, intramuscular, intraocular, intravitreal, iontophoretic, ophthalmic, oral, topical, and transdermal drug products and/or drug delivery systems.

In certain previous studies, many have described PVA as a mucoadhesive polymer, suggesting or reporting that incorporating PVA in the particle formulation process leads to particles that are strongly mucoadhesive. Surprisingly, and contrary to the established opinion that PVA is a mucoadhesive polymer, the inventors have discovered within the context of the invention that compositions and methods utilizing specific PVA grades aid particle transport in mucus and are not mucoadhesive in certain applications described herein. Specifically, mucus-penetrating particles can be prepared by tailoring the degree of hydrolysis and/or molecular weight of the PVA, which was previously unknown. This discovery significantly broadens the arsenal of techniques and ingredients applicable for manufacturing MPP and advantageously addresses certain limitations of certain existing materials that have been shown to facilitate mucus penetration, such as poly(ethylene glycol) (PEG) and (poly (ethylene oxide)-poly(propylene oxide)-poly(ethylene oxide) block copolymers (Pluronics®).

In particular, in light of drug delivery applications, there may be certain limitations involving PEGylated or Pluronic®-coated MPP: A) PEGylation of prefabricated particles or the use of PEG-containing block copolymers to produce PEGylated MPP may generate new inactive ingredients as defined by the FDA. These new ingredients may require expensive and time-consuming preclinical and clinical safety studies and represents significant regulatory hurdles with the FDA, which may limit the practical potential of PEGylated MPP. B) It is difficult to prepare Pluronic®-coated MPP directly via emulsification techniques, the industry's most popular and most universal approach to nano- and microencapsulation. This limitation significantly reduces the scope of compounds that can be efficiently encapsulated into Pluronic®-coated MPP. In particular, it may preclude efficient encapsulation of water soluble to slightly water soluble ingredients (e.g., drugs, proteins, oligonucleotides, etc. with an aqueous solubility of greater than about 1 mg/mL) that are most commonly encapsulated by double emulsion techniques. Accordingly, improvements in compositions and methods that would allow direct preparation of MPP by emulsification techniques would be beneficial. C) Pluronics® are currently not approved by the FDA for dosage via auricular, intramuscular, intraocular, intravitreal routes, which are approved dosage routes for PVA. Additionally, the maximum Pluronic® concentration currently approved by the FDA for ophthalmic dosage is 0.2%, while for PVA it is 1.4%. Accordingly, improvements in compositions and methods that would allow preparation of MPP by utilizing PVA (e.g., instead of Pluronics®) are likely to greatly facilitate clinical development of the mucus-penetrating particle technology overall and, in particular, for the aforementioned dosage routes.

In some embodiments described herein, the compositions and methods of making particles, including certain compositions and methods for making particles that have increased transport through mucosal barriers, address one or more, or all, of the concerns described above. Specifically, in some embodiments, the compositions and methods involve making mucus-penetrating particles by an emulsification process in the presence of specific PVAs. Advantageously, by utilizing PVA for MPP preparation, certain limitations of PEGylated or Pluronic®-coated MPP with respect to drug loading, scope of encapsulatable materials, and/or complexity of clinical development, may be addressed.

It should be appreciated that while in some embodiments it may be advantageous to form mucus-penetrating particles without the use of PEG or Pluronics®, in other embodiments PEG and/or Pluronics® may be included in the compositions and methods described herein.

In some embodiments, the particles described herein have a core-shell type arrangement. The core may comprise any suitable material such as a solid pharmaceutical agent or a salt thereof having a relatively low aqueous solubility a polymeric carrier, a lipid, and/or a protein. The core may be coated with a coating or shell comprising a surface-altering agent that facilitates mobility of the particle in mucus. As described in more detail below, in some embodiments the surface-altering agent may comprise a synthetic polymer having pendant hydroxyl groups on the backbone of the polymer. The molecular weight and/or degree of hydrolysis of the polymer may be chosen to impart certain transport characteristics to the particles, such as increased transport through mucus.

Non-limiting examples of particles are now provided. As shown in the illustrative embodiment of FIG. 1, a particle 10 includes a core 16 (which may be in the form of a particle, referred to herein as a core particle) and a coating 20 surrounding the core. In one set of embodiments, a substantial portion of the core is formed of one or more solid pharmaceutical agents (e.g., a drug, therapeutic agent, diagnostic agent, imaging agent) that can lead to certain beneficial and/or therapeutic effects. The core may be, for example, a nanocrystal (i.e., a nanocrystal particle) of a pharmaceutical agent. In other embodiments, the core may include a polymeric carrier, optionally with one or more pharmaceutical agents encapsulated or otherwise associated with the core. In yet other cases, the core may include a lipid, a protein, and/or another suitable material to be delivered to a subject. The core includes a surface 24 to which one or more surface-altering agents can be attached. For instance, in some cases, core 16 is surrounded by coating 20, which includes an inner surface 28 and an outer surface 32. The coating may be formed, at least in part, of one or more surface-altering agents 34, such as a polymer (e.g., a synthetic polymer or a polymer having pendant hydroxyl groups), which may associate with surface 24 of the core. Surface-altering agent 34 may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof. In one set of embodiments, the surface-altering agents, or portions thereof, are chosen to facilitate transport of the particle through a mucosal barrier (e.g., mucus or a mucosal membrane).

Particle 10 may optionally include one or more components 40 such as targeting moieties, proteins, nucleic acids, and bioactive agents which may optionally impart specificity to the particle. For example, a targeting agent or molecule (e.g., a protein, nucleic acid, nucleic acid analog, carbohydrate, or small molecule), if present, may aid in directing the particle to a specific location in the subject's body. The location may be, for example, a tissue, a particular cell type, or a subcellular compartment. One or more components 40, if present, may be associated with the core, the coating, or both; e.g., they may be associated with surface 24 of the core, inner surface 28 of the coating, outer surface 32 of the coating, and/or embedded in the coating. The one or more components 40 may be associated through covalent bonds, absorption, or attached through ionic interactions, hydrophobic and/or hydrophilic interactions, electrostatic interactions, van der Waals interactions, or combinations thereof. In some embodiments, a component may be attached (e.g., covalently) to one or more of the surface-altering agents of the coated particle using methods known to those of ordinary skill in the art.

Figure 1:
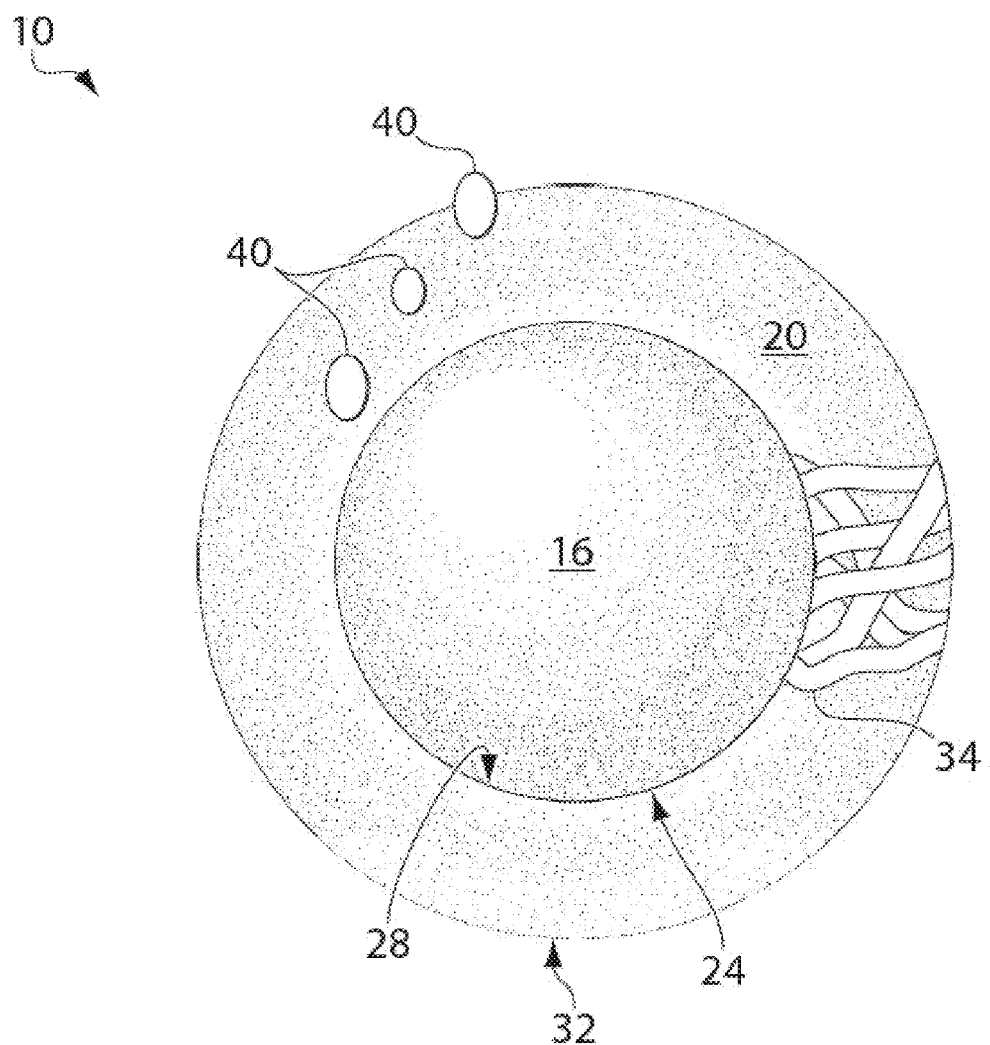
FIG. 1 is a schematic drawing of a mucus-penetrating particle having a coating and a core of a solid pharmaceutical agent according to one set of embodiments.

It should be understood that components and configurations other than those shown in FIG. 1 or described herein may be suitable for certain particles and compositions, and that not all of the components shown in FIG. 1 are necessarily present in some embodiments.

In one set of embodiments, particle 10, when introduced into a subject, may interact with one or more components in the subject such as mucus, cells, tissues, organs, particles, fluids (e.g., blood), portions thereof, and combinations thereof. In some such embodiments, the coating of particle 10 can be designed to include surface-altering agents or other components with properties that allow favorable interactions (e.g., transport, binding, adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One specific example includes choosing a certain hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported across a mucosal barrier (e.g., mucus or a mucosal membrane) in a subject, further interactions between the particle in the subject may take place. Interactions may take place, in some instances, through the coating and/or the core, and may involve, for example, the exchange of materials (e.g., pharmaceutical agents, therapeutic agents, proteins, peptides, polypeptides, nucleic acids, nutrients, e.g.) from the one or more components of the subject to particle 10, and/or from particle 10 to the one or more components of the subject. For example, in some embodiments in which the core is formed of or comprises a pharmaceutical agent, the breakdown, release and/or transport of the pharmaceutical agent from the particle can lead to certain beneficial and/or therapeutic effects in the subject. As such, the particles described herein can be used for the diagnosis, prevention, treatment or management of certain diseases or bodily conditions.

Specific examples for the use of the particles described herein are provided below in the context of being suitable for administration to a mucosal barrier (e.g., mucus or a mucosal membrane) in a subject. It should be appreciated that while many of the embodiments herein are described in this context, and in the context of providing a benefit for diseases and conditions that involve transport of materials across a mucosal barrier, the invention is not limited as such and the particles, compositions, kits, and methods described herein may be used to prevent, treat, or manage other diseases or bodily conditions.

Mucus is a sticky viscoelastic gel that protects against pathogens, toxins, and debris at various points of entry into the body, including the eyes, nose, lungs, gastrointestinal tract, and female reproductive tract. Many synthetic nanoparticles are strongly mucoadhesive and become effectively trapped in the rapidly-cleared peripheral mucus layer, vastly limiting their distribution throughout the mucosal membrane as well as penetration toward the underlying tissue. The residence time of these trapped particles is limited by the turnover rate of the peripheral mucus layer, which, depending on the organ, ranges from seconds to several hours. To ensure effective delivery of particles including pharmaceutical agents (e.g., therapeutic, diagnostic, and/or imaging agents) via mucus membranes, such particles must be able to readily diffuse through the mucus barrier, avoiding mucus adhesion.

It has been recently demonstrated that modifying surfaces of polymeric nanoparticles with a mucus-penetrating coating can minimize adhesion to mucus and thus allow rapid particle penetration across mucus barriers. Specifically, it has been shown that polymeric nanoparticles as large as 500 nm, when coated covalently with dense coatings of low molecular weight PEG (2 kDa-5 kDa) or non-covalently with specific Pluronic® molecules (e.g., P103, P105, F127) can penetrate human mucus nearly as fast as they move in pure water, and at rates almost 100-fold faster than similarly-sized uncoated polymeric particles. Despite these improvements, only a handful of surface coatings have been shown to facilitate mucus penetration of particles. Accordingly, improvements in compositions and methods involving mucus-penetrating particles for delivery of pharmaceutical agents would be beneficial.

Core Particles

As described above in reference to FIG. 1, particle 10 may include a core 16. The core may be formed of any suitable material, such as an organic material, an inorganic material, a polymer, a lipid, a protein or combinations thereof. In one set of embodiments, the core comprises a solid. The solid may be, for example, a crystalline or an amorphous solid, such as a crystalline or amorphous solid pharmaceutical agent (e.g., a therapeutic agent, diagnostic agent, and/or imaging agent), or a salt thereof. In other embodiments, the core may comprise a gel or a liquid (e.g., an oil-in-water or water-in-oil emulsion). In some embodiments, more than one pharmaceutical agents may be present in the core. Specific examples of pharmaceutical agents are provided in more detail below.

The pharmaceutical agent may be present in the core in any suitable amount, e.g., at least about 0.01 wt %, at least about 0.1 wt %, at least about 1 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, or at least about 99 wt % of the core. In one embodiment, the core is formed of 100 wt % of the pharmaceutical agent. In some cases, the pharmaceutical agent may be present in the core at less than about 100 wt %, less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %. Combinations of the above-referenced ranges are also possible (e.g., present in an amount of at least about 80 wt % and less than about 100 wt %). Other ranges are also possible.

In embodiments in which the core particles comprise relatively high amounts of a pharmaceutical agent (e.g., at least about 50 wt % of the core particle), the core particles generally have an increased loading of the pharmaceutical agent compared to particles that are formed by encapsulating agents into polymeric carriers. This is an advantage for drug delivery applications, since higher drug loadings mean that fewer numbers of particles may be needed to achieve a desired effect compared to the use of particles containing polymeric carriers.

As described herein, in other embodiments in which a relatively high amounts of a polymer or other material forms the core, less amounts of pharmaceutical agent may be present in the core.

The core may be formed of solid materials having various aqueous solubilities (i.e., a solubility in water, optionally with one or more buffers), and/or various solubilities in the solution in which the solid material is being coated with a surface-altering agent. For example, the solid material may have an aqueous solubility (or a solubility in a coating solution) of less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the solid material may have an aqueous solubility (or a solubility in a coating solution) of at least about 1 pg/mL, at least about 10 pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility or a solubility in a coating solution of at least about 10 pg/mL and less than or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

Although a core may be hydrophobic or hydrophilic, in many embodiments described herein, the core is substantially hydrophobic. "Hydrophobic" and "hydrophilic" are given their ordinary meaning in the art and, as will be understood by those skilled in the art, in many instances herein, are relative terms. Relative hydrophobicities and hydrophilicities of materials can be determined by measuring the contact angle of a water droplet on a planar surface of the substance to be measured, e.g., using an instrument such as a contact angle goniometer and a packed powder of the core material.

In some embodiments, a material (e.g., a material forming a particle core) has a contact angle of at least about 20 degrees, at least about 30 degrees, at least about 40 degrees, at least about 50 degrees, at least about 60 degrees, at least about 70 degrees, at least about 80 degrees, at least about 90 degrees, at least about 100 degrees, at least about 110 degrees, at least about 120 degrees, or at least about 130 degrees. In some embodiments, a material has a contact angle of less than or equal to about 160 degrees, less than or equal to about 150 degrees, less than or equal to about 140 degrees, less than or equal to about 130 degrees, less than or equal to about 120 degrees, less than or equal to about 110 degrees, less than or equal to about 100 degrees, less than or equal to about 90 degrees, less than or equal to about 80 degrees, or less than or equal to about 70 degrees. Combinations of the above-referenced ranges are also possible (e.g., a contact angle of at least about 30 degrees and less than or equal to about 120 degrees). Other ranges are also possible.

Contact angle measurements can be made using a variety of techniques; here a static contact angle measurement between a pellet of the starting material which will be used to form the core and a bead of water is referenced. The material used to form the core was received as a fine powder or otherwise was ground into a fine powder using a mortar and pestle. In order to form a surface on which to make measurements, the powder was packed using a 7 mm pellet die set from International Crystal Labs. The material was added to the die and pressure was applied by hand to pack the powder into a pellet, no pellet press or high pressure was used. The pellet was then suspended for testing so that the top and bottom of the pellet (defined as the surface water is added to and the opposite parallel surface respectively) were not in contact with any surface. This was done by not fully removing the pellet from the collar of the die set. The pellet therefore touches the collar on the sides and makes no contact on the top or bottom. For contact angle measurements, water was added to the surface of the pellet until a bead of water with a steady contact angle over 30 seconds was obtained. The water was added into the bead of water by submerging or contacting the tip of the pipette or syringe used for addition to the bead of water. Once a stable bead of water was obtained, an image was taken and the contact angle was measured using standard practices.

In embodiments in which the core comprises an inorganic material (e.g., for use as imaging agents), the inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt %. In one embodiment, the core is formed of 100 wt % inorganic material. In some cases, the inorganic material may be present in the core at less than about 100 wt %, less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %. Combinations of the above-referenced ranges are also possible (e.g., present in an amount of at least about 1 wt % and less than about 20 wt %). Other ranges are also possible.

The core may, in some cases, be in the form of a quantum dot, a carbon nanotube, a carbon nanowire, or a carbon nanorod. In some cases, the core comprises, or is formed of, a material that is not of biological origin.

In some embodiments, the core includes one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. Other examples of polymers that may be suitable for portions of the core include those herein suitable for forming coatings on particles, as described below. In some cases, the one or more polymers present in the core may be used to encapsulate or adsorb one or more pharmaceutical agents.

In certain embodiments, a core may include a pharmaceutical agent comprising a lipid and/or a protein. Other materials are also possible.

If a polymer is present in the core, the polymer may be present in the core in any suitable amount, e.g., less than about 100 wt %, less than about 90 wt %, less than about 80 wt %, less than about 70 wt %, less than about 60 wt %, less than about 50 wt %, less than about 40 wt %, less than about 30 wt %, less than about 20 wt %, less than about 10 wt %, less than about 5 wt %, less than about 2 wt %, or less than about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than about 20 wt %). Other ranges are also possible. In one set of embodiments, the core is formed is substantially free of a polymeric component.

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than or equal to about 10 µm, less than or equal to about 5 µm, less than or equal to about 1 µm, less than or equal to about 800 nm, less than or equal to about 700 nm, less than or equal to about 500 nm, less than or equal to 400 nm, less than or equal to 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core may have a largest or smallest cross-sectional dimension of, for example, at least about 5 nm, at least about 20 nm, at least about 50 nm, at least about 100 nm, at least about 200 nm, at least about 300 nm, at least about 400 nm, at least about 500 nm, at least about 1 µm, or at least about 5 µm. Combinations of the above-referenced ranges are also possible (e.g., a largest or smallest cross-sectional dimension of at least about 50 nm and less than about 500 nm). Other ranges are also possible. In some embodiments, the sizes of the cores formed by a process described herein have a Gaussian-type distribution. Unless indicated otherwise, the measurements of particle/core sizes herein refer to the smallest cross-sectional dimension.

Those of ordinary skill in the art are familiar with techniques to determine sizes (e.g., smallest or largest cross-sectional dimensions) of particles. Examples of suitable techniques include (DLS), transmission electron microscopy, scanning electron microscopy, electroresistance counting and laser diffraction. Other suitable techniques are known to those or ordinary skill in the art. Although many methods for determining sizes of particles are known, the sizes described herein (e.g., average particle sizes, thicknesses) refer to ones measured by dynamic light scattering.

Methods of Forming Core Particles and Coated Particles

The core particles described herein may be formed by any suitable method. Suitable methods may include, for example, so called top-down techniques, i.e. techniques based on size reduction of relatively large particles into smaller particles (e.g., milling or homogenization) or so called bottom-up techniques, i.e. techniques based on the growth of particles from smaller particles or individual molecules (e.g., precipitation or spray-freezing into liquid).

In some embodiments, core particles may be coated with a coating. For example, core particles may be provided or formed in a first step, and then the particles may be coated in a second step to form coated particles. In other embodiments, core particles may be formed and coated substantially simultaneously (e.g., in a single step). Examples of these and other methods are provided below.

In some embodiments involving a core comprising a solid material, a milling process may be used to reduce the size of the solid material to form particles in the micrometer to nanometer size range. Dry and wet milling processes such as jet milling, cryo-milling, ball milling, media milling, and homogenization are known and can be used in methods described herein. Generally, in a wet milling process, a suspension of the material to be used as the core is agitated with or without excipients to reduce particle size. Dry milling is a process wherein the material to be used as the core is mixed with milling media with or without excipients to reduce particle size. In a cryo-milling process, a suspension of the material to be used as the core is mixed with milling media with or without excipients under cooled temperatures.

In some embodiments, the core particles described herein may be produced by milling of a solid material (e.g., a pharmaceutical agent) in the presence of one or more stabilizers/surface-altering agents. Small particles of a solid material may require the presence of one or more stabilizers/surface-altering agents, particularly on the surface of the particles, in order to stabilize a suspension of particles without agglomeration or aggregation in a liquid solution. In some such embodiments, the stabilizer may act as a surface-altering agent, forming a coating on the particle.

As described herein, in some embodiments, a method of forming a core particle involves choosing a stabilizer/surface-altering agent that is suitable for both milling and for forming a coating on the particle and rendering the particle mucus penetrating. For example, as described in more detail below, it has been demonstrated that 200-500 nm nanoparticles of a model compound pyrene produced by milling of pyrene in the presence of certain PVA polymers resulted in particles that can penetrate physiological mucus samples at the same rate as well-established polymer-based MPP. Interestingly, it was observed that only a subset of PVA polymers tested fit the criteria of being suitable for both milling and for forming a coating on the particle that renders the particle mucus penetrating, as described in more detail below.

In a wet milling process, milling can be performed in a dispersion (e.g., an aqueous dispersion) containing one or more stabilizers (e.g., a surface-altering agent), a grinding medium, a solid to be milled (e.g., a solid pharmaceutical agent), and a solvent. Any suitable amount of a stabilizer/surface-altering agent can be included in the solvent. In some embodiments, a stabilizer/surface-altering agent may be present in the solvent in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the stabilizer/surface-altering agent may be present in the solvent in an amount of about 100% (e.g., in an instance where the stabilizer/surface-altering agent is the solvent). In other embodiments, the stabilizer/surface-altering agent may be present in the solvent in an amount of less than or equal to about 100%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 5% and at least about 1% of the solvent). Other ranges are also possible. The particular range chosen may influence factors that may affect the ability of the particles to penetrate mucus such as the stability of the coating of the stabilizer/surface-altering agent on the particle surface, the average thickness of the coating of the stabilizer/surface-altering agent on the particles, the orientation of the stabilizer/surface-altering agent on the particles, the density of the stabilizer/surface altering agent on the particles, stabilizer:drug ratio, drug concentration, the size and polydispersity of the particles formed, and the morphology of the particles formed.

The pharmaceutical agent (or salt thereof) may be present in the solvent in any suitable amount. In some embodiments, the pharmaceutical agent (or salt thereof) is present in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the pharmaceutical agent (or salt thereof) may be present in the solvent in an amount of less than or equal to about 100%, less than or equal to about 90%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 20% and at least about 1% of the solvent). In some embodiments, the pharmaceutical agent is present in the above ranges but in w:v The ratio of stabilizer/surface-altering agent to pharmaceutical agent (or salt thereof) in a solvent may also vary. In some embodiments, the ratio of stabilizer/surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of stabilizer/surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

Stabilizers/surface-altering agents may be, for example, polymers or surfactants. Examples of polymers are those suitable for use in coatings, as described in more detail below. Non-limiting examples of surfactants that are suitable for use in coatings as surface-altering agents include L-α-phosphatidylcholine (PC), 1,2-dipalmitoylphosphatidylcholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

It should be appreciated that while in some embodiments the stabilizer/surface-altering agent used for milling forms a coating on a particle surface, which coating renders particle mucus penetrating, in other embodiments, the stabilizer/surface-altering agent may be exchanged with one or more other stabilizers/surface-altering agents after the particle has been formed. For example, in one set of methods, a first stabilizer/surface-altering agent may be used during a milling process and may coat a surface of a core particle, and then all or portions of the first stabilizer/surface-altering agent may be exchanged with a second stabilizer/surface-altering agent to coat all or portions of the core particle surface. In some cases, the second stabilizer/surface-altering agent may render the particle mucus penetrating more than the first stabilizer/surface-altering agent. In some embodiments, a core particle having a coating including multiple surface-altering agents may be formed.

Any suitable grinding medium can be used for milling. In some embodiments, a ceramic and/or polymeric material and/or a metal can be used. Examples of suitable materials may include zirconium oxide, silicon carbide, silicon oxide, silicon nitride, zirconium silicate, yttrium oxide, glass, alumina, alpha-alumina, aluminum oxide, polystyrene, poly(methyl methacrylate), titanium, steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than or equal to about 5 mm, less than or equal to about 2 mm, less than or equal to about 1 mm, less than or equal to about 0.8, less than or equal to about 0.5 mm, or less than or equal to about 0.2 mm. Combinations of the above-referenced ranges are also possible (e.g., an average diameter of at least about 0.5 millimeters and less than or equal to about 1 mm). Other ranges are also possible.

Any suitable solvent may be used for milling. The choice of solvent may depend on factors such as the solid material (e.g., pharmaceutical agent) being milled, the particular type of stabilizer/surface-altering agent being used (e.g., one that may render the particle mucus penetrating), the grinding material be used, among other factors. Suitable solvents may be ones that do not substantially dissolve the solid material or the grinding material, but dissolve the stabilizer/surface-altering agent to a suitable degree. Non-limiting examples of solvents may include water, buffered solutions, other aqueous solutions, alcohols (e.g., ethanol, methanol, butanol), and mixtures thereof that may optionally include other components such as pharmaceutical excipients, polymers, pharmaceutical agents, salts, preservative agents, viscosity modifiers, tonicity modifier, taste masking agents, antioxidants, pH modifier, and other pharmaceutical excipients. In other embodiments, an organic solvent can be used. A pharmaceutical agent may have any suitable solubility in these or other solvents, such as a solubility in one or more of the ranges described above for aqueous solubility or for solubility in a coating solution.

In other embodiments, core particles may be formed by an emulsification technique (emulsification). Generally, emulsification techniques may involve dissolving or dispersing a material to be used as the core in a solvent; this solution or dispersion is then emulsified in a second immiscible solvent, thereby forming a plurality of particles comprising the material. Suitable emulsification techniques may include formation of oil-in-water emulsions, water-in-oil emulsions, water-oil-water emulsions, oil-water-oil emulsions, solid-in-oil-in-water emulsions, and solid-in-water-in-oil emulsions, etc., with or without subsequent solvent removal, for example, by evaporation or extraction. Emulsification techniques are versatile and may be useful for preparing core particles comprising pharmaceutical agents having a relatively low aqueous solubility as well as pharmaceutical agents having a relatively high aqueous solubility.

In some embodiments, the core particles described herein may be produced by emulsification in the presence of one or more stabilizers. In some such embodiments, the stabilizer may act as a surface-altering agent, forming a coating on the particle (i.e., the emulsification and coating steps may be performed substantially simultaneously).

In some embodiments, a method of forming a core particle by emulsification involves choosing a stabilizer that is suitable for both emulsification and for forming a coating on the particle and rendering the particle mucus penetrating. For example, as described in more detail below, it has been demonstrated that 200-500 nm nanoparticles of a model polymer PLA produced by emulsification in the presence of certain PVA polymers resulted in particles that can penetrate physiological mucus samples at the same rate as well-established polymer-based MPP. Interestingly, it was observed that only a subset of PVA polymers tested fit the criteria of being suitable for both emulsification and for forming a coating on the particle that renders the particle mucus penetrating, as described in more detail below.

In other embodiments, the particles are first formed using an emulsification technique, following by coating of the particles with a surface-altering agent.

Any suitable solvent and solvent combinations can be used for emulsification. Some examples of solvents which can serve as oil phase are organic solvents such chloroform, dichloromethane, ethyl acetate, ethyl ether, petroleum ether (hexane, heptane), and oils such as peanut oil, cottonseed oil; safflower oil; sesame oil; olive oil; corn oil soybean oil, and silicone oil. Some examples of solvents which can serve as water phase are water and aqueous buffers. Other solvents are also possible.

In other embodiments, core particles may be formed by a precipitation technique. Precipitation techniques (e.g., microprecipitation techniques, nanoprecipitation techniques) may involve forming a first solution comprising the material to be used as the core (e.g., a pharmaceutical agent) and a solvent, wherein the material is substantially soluble in the solvent. The solution may be added to a second solution comprising another solvent in which the material is substantially insoluble (i.e., an anti-solvent), thereby forming a plurality of particles comprising the material. In some cases, one or more surface-altering agents, surfactants, materials, and/or bioactive agents may be present in the first and/or second solutions. A coating may be formed during the process of precipitating the core (e.g., the precipitating and coating steps may be performed substantially simultaneously). In other embodiments, the particles are first formed using a precipitation technique, following by coating of the particles with a surface-altering agent.

In some embodiments, a precipitation technique may be used to form polymeric core particles with or without a pharmaceutical agent. Generally, a precipitation technique involves dissolving the polymer to be used as the core in a solvent (with or without a pharmaceutical agent present), and the solution is then added to a miscible anti-solvent (with or without excipients present) to form the core particle. In some embodiments, this technique may be useful for preparing, for example, polymeric core particles comprising pharmaceutical agents that are slightly soluble (1-10 mg/L), very slightly soluble (0.1-1 mg/mL) or practically insoluble (<0.1 mg/mL) in aqueous solutions (e.g., agents having a relatively low aqueous solubility).

Any suitable solvent can be used for precipitation. In some embodiments, a suitable solvent for precipitation may include, for example, acetone, acetonitrile, dimethylformamide, dimethysulfoxide, N-methyl-2-pyrrolidone, 2-pyrrolidone, tetrahydrofuran. Other organic solvents and non-organic solvents can also be used.

Any suitable anti-solvent can be used for precipitation, including the solvents described herein that may be used for milling. In one set of embodiments, an aqueous solution is used (e.g., water, buffered solutions, other aqueous solutions, and alcohols such as ethanol, methanol, butanol), and mixtures thereof that may optionally include other components such as pharmaceutical excipients, polymers, and pharmaceutical agents.

Stabilizers/surface-altering agents for emulsification and precipitation may be polymers or surfactants, including the stabilizers/surface-altering agents described herein that may be used for milling.

Non-limiting examples of suitable polymers suitable for forming all or portions of a core by emulsification or precipitation may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, polyarylates, polypeptides, polynucleotides, and polysaccharides. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly (ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone, bovine serum albumin, human serum albumin, collagen, DNA, RNA, carboxymethyl cellulose, chitosan, dextran.

In some embodiments, a precipitation technique may be used to form particles comprised predominantly of a pharmaceutical agent (e.g., nanocrystals). Generally, such a precipitation technique involves dissolving the pharmaceutical agent to be used as the core in a solvent, which is then added to a miscible anti-solvent with or without excipients to form the core particle. In some embodiments, this technique may be useful for preparing, for example, particles of pharmaceutical agents that are slightly soluble (1-10 mg/L), very slightly soluble (0.1-1 mg/mL) or practically insoluble (<0.1 mg/mL) in aqueous solutions (e.g., agents having a relatively low aqueous solubility).

In some embodiments, precipitation by salt (or complex) formation may be used to form particles (e.g., nanocrystals) of a salt of a pharmaceutical agent. Generally, precipitation by salt formation involves dissolving the material to be used as the core in a solvent with or without excipients followed by addition of a counter-ion or a complexing agent, which forms an insoluble salt or a complex with the pharmaceutical agent to form the core particle. This technique may be useful for preparing particles of pharmaceutical agents that are soluble in aqueous solutions (e.g., agents having a relatively high aqueous solubility). In some embodiments, pharmaceutical agents having one or more charged or ionizable groups can interact with a counter-ion (e.g., a cation or an anion) to form a salt complex.

A variety of counter-ions can be used to form salt complexes, including metals (e.g., alkali metals, alkali earth metals and transition metals). Non-limiting examples of cationic counter-ions include zinc, calcium, aluminum, zinc, barium, and magnesium. Non-limiting examples of anionic counter-ions include phosphate, carbonate, and fatty acids. Counter-ions may be, for example, monovalent, divalent, or trivalent. Other counter-ions are known in the art and can be used in the embodiments described herein. Other ionic and non-ionic complexing agents are also possible.

A variety of different acids may be used in a precipitation process. In some embodiments, a suitable acid may include deconoic acid, hexanoic acid, mucic acid, octanoic acid. In other embodiments, a suitable acid may include acetic acid, adipic acid, L-ascorbic acid, L-aspartic acid, capric acid (decanoic acid), carbonic acid, citric acid, fumaric acid, galactaric acid, D-glucoheptonic acid, D-gluconic acid, D-glucuronic acid, glutamic acid, glutaric acid, glycerophosphoric acid, glycolic acid, hippuric acid, hydrochloric acid, DL-lactic acid, lauric acid, maleic acid, (−)-L-malic acid, palmitic acid, phosphoric acid, sebacic acid, stearic acid, succinic acid, sulfuric acid, (+)-L-tartaric acid, or thiocyanic acid. In other embodiments, a suitable acid may include alginic acid, benzenesulfonic acid, benzoic acid, (+)-camphoric acid, caprylic acid (octanoic acid), cyclamic acid, dodecylsulfuric acid, ethane-1,2-disulfonic acid, ethanesulfonic acid, ethanesulfonic acid, 2-hydroxy-, gentisic acid, glutaric acid, 2-oxo-, isobutyric acid, lactobionic acid, malonic acid, methanesulfonic acid, naphthalene-1,5-disulfonic acid, naphthalene-2-sulfonic acid, 2-naphthoic acid, 1-hydroxy-, nicotinic acid, oleic acid, orotic acid, oxalic acid, pamoic acid, (embonic acid), propionic acid, (−)-L-pyroglutamic acid, or p-toluenesulfonic acid. In yet other embodiments, a suitable acid may include acetic acid, 2,2-dichloro-, benzoic acid, 4-acetamido-, (+)-camphor-10-sulfonic acid, caproic acid (hexanoic acid), cinnamic acid, formic acid, hydrobromic acid, DL-mandelic acid, nitric acid, salicylic acid, salicylic acid, 4-amino-, or undecylenic acid (undec-10-enoic acid). Mixtures of one or more such acids can also be used.

A variety of different bases may be used in a precipitation process. In some embodiments, a suitable base includes ammonia, L-arginine, calcium hydroxide, choline, glucamine, N-methyl-, lysine, magnesium hydroxide, potassium hydroxide, or sodium hydroxide. In other embodiments, a suitable base may include benethamine, benzathine, betaine, deanol, diethylamine, ethanol, 2-(diethylamino)-, hydrabamine, morpholine, 4-(2-hydroxyethyl)-morpholine, pyrrolidine, 1-(2-hyroxyethyl)-, or tromethamine. In other embodiments, a suitable base may include diethanolamine (2,2'-iminobis(ethanol)), ethanolamine (2-aminoethanol), ethylenediamine, 1H-imidazole, piperazine, triethanolamine (2,2',2"-nitrilotris(ethanol)), or zinc hydroxide. Mixtures of one or more such bases can also be used.

Any suitable solvent can be used for precipitation by salt formation, including the solvents described herein that may be used for milling. In one set of embodiments, an aqueous solution is used (e.g., water, buffered solutions, other aqueous solutions, alcohols (e.g., ethanol, methanol, butanol), and mixtures thereof that may optionally include other components such as pharmaceutical excipients, polymers, and pharmaceutical agents.

In the precipitation process, the salt may have a lower aqueous solubility (or solubility in the solvent containing the salt) than the pharmaceutical agent in the non-salt form. The aqueous solubility (or solubility in the solvent) of the salt may be, for example, less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, or less than or equal to about 0.01 mg/mL, less than or equal to about 1 μg/mL, less than or equal to about 0.1 μg/mL, less than or equal to about 0.01 μg/mL, less than or equal to about 1 ng/mL, less than or equal to about 0.1 ng/mL, or less than or equal to about 0.01 ng/mL at 25° C. In some embodiments, the salt may have an aqueous solubility (or solubility in the solvent) of at least about 1 pg/mL, at least about 10 pg/mL, at least about 0.1 ng/mL, at least about 1 ng/mL, at least about 10 ng/mL, at least about 0.1 μg/mL, at least about 1 μg/mL, at least about 5 μg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility (or solubility in the solvent) of at least about 0.001 mg/mL and less than or equal to about 1 mg/mL). Other ranges are also possible. The salt may have these or other ranges of aqueous solubilities at any point throughout the pH range (e.g., from pH 1 to pH 14).

In some embodiments, the solvent used for precipitation includes one or more surface-altering agents as described herein, and a coating of the one or more surface-altering agents may be formed around the particle as it precipitates out of solution. The surface-altering agent may be present in the solvent at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01 (w/v) and less than or equal to about 1% (w/v). Other ranges are also possible.

Another exemplary method of forming a core particle includes a freeze-drying technique. In this technique, a pharmaceutical agent or salt thereof may be dissolved in an aqueous solution, optionally containing a surface-altering agent. A counter-ion may be added to the solution, and the solution may be immediately flash frozen and freeze dried. Dry powder can be reconstituted in a suitable solvent (e.g., an aqueous solution such as water) at a desired concentration.

A counter-ion may be added to a solvent for freeze-drying in any suitable range. In some cases, the ratio of counter-ion to pharmaceutical agent (e.g., salt) may be at least 0.1:1 (weight ratio or molar ratio), at least 1:1, at least 2:1, at least 3:1, at least 5:1, at least 10:1, at least 25:1, at least 50:1, or at least 100:1. In some cases, the ratio of counter-ion to pharmaceutical agent (e.g., salt) may be less than or equal to 100:1 (weight ratio or molar ratio), less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

If the surface-altering agent is present in the solvent prior to freeze drying, it may be present at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01% (w/v) and less than or equal to about 1% (w/v). Other ranges are also possible.

The concentration of surface-altering agent present in the solvent may be above or below the critical micelle concentration (CMC) of the surface-altering agent, depending on the particular surface-altering agent used. In other embodiments, stable particles can be formed by adding excess counter-ion to a solution containing a pharmaceutical agent. The precipitate can then be washed by various methods such as centrifugation. The resultant slurry may be sonicated. One or more surface-altering agents may be added to stabilize the resultant particles.

Other methods of forming core particles are also possible. Techniques for forming core particles may include, for example, coacervation-phase separation; melt dispersion; interfacial deposition; in situ polymerization; self-assembly of macromolecules (e.g., formation of polyelectrolyte complexes or polyelectrolyte-surfactant complexes); spray-drying and spray-congealing; electro-spray; air suspension coating; pan and spray coating; freeze-drying, air drying, vacuum drying, fluidized-bed drying; precipitation (e.g., nanoprecipitation, microprecipitation); critical fluid extraction; and lithographic approaches (e.g., soft lithography, step and flash imprint lithography, interference lithography, photolithography).

Combinations of the methods described herein and other methods are also possible. For example, in some embodiments, a core of a pharmaceutical agent is first formed by precipitation, and then the size of the core is further reduced by a milling process.

Following formation of particles of a pharmaceutical agent, the particles may be optionally exposed to a solution comprising a (second) surface-altering agent that may associate with and/or coat the particles. In embodiments in which the pharmaceutical agent already includes a coating of a first surface-altering agent, all or portions of a second surface-altering agent may be exchanged with a second stabilizer/surface-altering agent to coat all or portions of the particle surface. In some cases, the second surface-altering agent may render the particle mucus penetrating more than the first surface-altering agent. In other embodiments, a particle having a coating including multiple surface-altering agents may be formed (e.g., in a single layer or in multiple layers). In other embodiments, a particle having multiple coatings (e.g., each coating optionally comprising different surface-altering agents) may be formed. In some cases, the coating is in the form of a monolayer of a surface-altering agent. Other configurations are also possible.

In any of the methods described herein, a particle may be coated with a surface-altering agent by incubating the particle in a solution with the surface-altering agent for a period of at least about 1 minutes, at least about 2 minutes, at least about 5 min., at least about 10 min., at least about 15 min., at least about 20 min., at least about 30 min., at least about 60 min., or more. In some cases, incubation may take place for a period of less than or equal to about 10 hours, less than or equal to about 5 hours, or less than or equal to about 60 min. Combinations of the above referenced ranges are also possible (e.g., an incubation period of less than or equal to 60 min. and at least about 2 min.).

Particle Coatings

As shown in the embodiment illustrated in FIG. 1, core 16 may be surrounded by coating 20 comprising one or more surface-altering agents. The particular chemical makeup and/or components of the coating and surface-altering agent(s) can be chosen so as to impart certain functionality to the particles, such as enhanced transport through mucosal barriers.

It should be understood that a coating which surrounds a core need not completely surround the core, although such embodiments may be possible. For example, the coating may surround at least about 10%, at least about 30%, at least about 50%, at least about 60%, at least about 70%, at least about 80%, at least about 90%, or at least about 99% of the surface area of a core. In some cases, the coating substantially surrounds a core. In other cases, the coating completely surrounds a core. In other embodiments, a coating surrounds less than or equal to about 100%, less than or equal to about 90%, less than or equal to about 80%, less than or equal to about 70%, less than or equal to about 60%, or less than or equal to about 50% of the surface area of a core. Combinations of the above-referenced ranges are also possible (e.g., surrounding greater than 80% and less than 100% of the surface area of a core).

The components of the coating may be distributed evenly across a surface of the core in some cases, and unevenly in other cases. For example, the coating may include portions (e.g., holes) that do not include any material in some cases. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material, or multilayers of materials in some embodiments. A single type of surface-altering agent may be present, or multiple types of surface-altering agent.

A coating of a particle can have any suitable thickness. For example, a coating may have an average thickness of at least about 1 nm, at least about 5 nm, at least about 10 nm, at least about 30 nm, at least about 50 nm, at least about 100 nm, at least about 200 nm, at least about 500 nm, at least about 1 µm, or at least about 5 µm. In some cases, the average thickness of a coating is less than or equal to about 5 µm, less than or equal to about 1 µm, less than or equal to about 500 nm, less than or equal to about 200 nm, less than or equal to about 100 nm, less than a to about 50 nm, less than or equal to about 30 nm, less than or equal to about 10 nm, or less than or equal to about 5 nm. Combinations of the above-referenced ranges are also possible (e.g., an average thickness of at least about 1 nm and less than or equal to about 100 nm). Other ranges are also possible. For particles having multiple coatings, each coating layer may have one of the thicknesses described above.

In some embodiments, the compositions and methods described herein may allow for the coating of a core particle with hydrophilic surface-altering moieties without requiring covalent linking of the surface-altering moieties to the core surface. In some such embodiments, a core having a hydrophobic surface may be coated with a polymer described herein, thereby causing a plurality of surface-altering moieties to be on the core surface without substantially altering the characteristics of the core itself. In other embodiments, however, a surface-altering agent is covalently linked to a core particle. The coating and/or surface-altering agent of a particle described herein may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, rubber). In certain embodiments, the polymer is a surface active polymer. In certain embodiments, the polymer is a non-ionic polymer. In certain embodiments, the polymer is a linear, synthetic non-ionic polymer. In certain embodiments, the polymer is a non-ionic block copolymer. In some embodiments, the polymer may be a copolymer, e.g., where one repeat unit is relatively hydrophobic and another repeat unit is relatively hydrophilic. The copolymer may be, for example, a diblock, triblock, alternating, or random copolymer. The polymer may be charged or uncharged.

In some embodiments, a coating comprises a synthetic polymer having pendant hydroxyl groups on the backbone of the polymer. For example, in certain embodiments, the polymer may include poly(vinyl alcohol), a partially hydrolyzed poly(vinyl acetate) or a copolymer of vinyl alcohol and vinyl acetate. In certain embodiments, a synthetic polymer having pendant hydroxyl groups on the backbone of the polymer may include poly(ethylene glycol)-poly(vinyl acetate)-poly(vinyl alcohol) copolymers, poly(ethylene glycol)-poly(vinyl alcohol) copolymers, poly(propylene oxide)-poly(vinyl alcohol) copolymers, and poly(vinyl alcohol)-poly(acryl amide) copolymers. Without wishing to be bound by theory, a particle including a coating comprising a synthetic polymer having pendant hydroxyl groups on the backbone of the polymer may have reduced mucoadhesion as compared to a control particle due to, at least in part, the display of a plurality of hydroxyl groups on the particle surface. One possible mechanism for the reduced mucoadhesion is that the hydroxyl groups alter the microenvironment of the particle, for example, by ordering water and other molecules in the particle/mucus environment. An additional or alternative possible mechanism is that the hydroxyl groups shield the adhesive domains of the mucin fibers, thereby reducing particle adhesion and speeding up particle transport.

Moreover, the ability of a particle coated with a synthetic polymer having pendant hydroxyl groups on the backbone of the polymer to be mucus penetrating may also depend, at least in part, on the degree of hydrolysis of the polymer. In some embodiments, the hydrophobic portions of the polymer (e.g., portions of the polymer that are not hydrolyzed) may allow the polymer to be adhered to the core surface (e.g., in the case of the core surface being hydrophobic), thus allowing for a strong association between the core and the polymer. Surprisingly, it has been found that in some embodiments involving the surface-altering agent PVA, too high of a degree of hydrolysis does not allow for sufficient adhesion between the PVA and the core (e.g., in the case of the core being hydrophobic), and thus, the particles coated with such a polymer generally do not exhibit sufficient reduced mucoadhesion. In some embodiments, too low of a degree of hydrolysis does not enhance particle transport in mucus, perhaps due to the lower amounts of hydroxyl groups available for altering the microenvironment of the particle and/or shielding the adhesive domains of the mucin fibers.

A synthetic polymer having pendant hydroxyl groups on the backbone of the polymer may have any suitable degree of hydrolysis (and, therefore, varying amounts of hydroxyl groups). The appropriate level of hydrolysis may depend on additional factors such as the molecular weight of the polymer, the composition of the core, the hydrophobicity of the core, etc. In some embodiments, a synthetic polymer (e.g., PVA or partially hydrolyzed poly(vinyl acetate) or a copolymer of vinyl alcohol and vinyl acetate) may be at least about 30% hydrolyzed, at least about 35% hydrolyzed, at least about 40% hydrolyzed, at least about 45% hydrolyzed, at least about 50% hydrolyzed, at least about 55% hydrolyzed, at least about 60% hydrolyzed, at least about 65% hydrolyzed, at least about 70% hydrolyzed, at least about 75% hydrolyzed, at least about 80% hydrolyzed, at least about 85% hydrolyzed, at least about 87% hydrolyzed, at least about 90% hydrolyzed, at least about 95% hydrolyzed, or at least about 98% hydrolyzed. In some embodiments, the synthetic polymer may be less than about 100% hydrolyzed, less than about 98% hydrolyzed, less than about 97% hydrolyzed, less than about 96% hydrolyzed, less than about 95% hydrolyzed, less than about 94% hydrolyzed, less than about 93% hydrolyzed, less than about 92% hydrolyzed, less than about 91% hydrolyzed, less than about 90% hydrolyzed, less than about 87% hydrolyzed, less than about 85% hydrolyzed, less than about 80% hydrolyzed, less than about 75% hydrolyzed, less than about 70% hydrolyzed, or less than about 60% hydrolyzed. Combinations of the above-mentioned ranges are also possible (e.g., a polymer that is at least about 80% hydrolyzed and less than about 95% hydrolyzed). Other ranges are also possible.

The molecular weight of a synthetic polymer described herein (e.g., one having pendant hydroxyl groups on the backbone of the polymer) may be selected so as to reduce the mucoadhesion of a core and to ensure sufficient association of the polymer with the core. In certain embodiments, the molecular weight of the synthetic polymer is at least about 1 kDa, at least about 2 kDa, at least about 5 kDa, at least about 8 kDa, at least about 9 kDa, at least about 10 kDa, at least about 12 kDa, at least about 15 kDa at least about 20 kDa, at least about 25 kDa, at least about 30 kDa, at least about 40 kDa, at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of the synthetic polymer is less than or equal to about 1000 kDa, less than or equal to about 500 kDa, less than or equal to about 200 kDa, less than or equal to about 180 kDa, less than or equal to about 150 kDa, less than or equal to about 130 kDa, less than or equal to about 120 kDa, less than or equal to about 100 kDa, less than or equal to about 85 kDa, less than or equal to about 70 kDa, less than or equal to about 65 kDa, less than or equal to about 60 kDa, less than or equal to about 50 kDa, or less than or equal to about 40 kDa, less than or equal to about 30 kDa, less than or equal to about 20 kDa, less than or equal to about 15 kDa, or less than or equal to about 10 kDa. Combinations of the above-mentioned ranges are also possible (e.g., a molecular weight of at least about 10 kDa and less than or equal to about 30 kDa). The above-mentioned molecular weight ranges can also be combined with the above-mentioned hydrolysis ranges to form suitable polymers.

In some embodiments, a synthetic polymer described herein is or comprises PVA. PVA is a non-ionic polymer with surface active properties. It is a synthetic polymer typically produced through hydrolysis of poly(vinyl acetate). Partially hydrolyzed PVA is comprised of two types of repeating units: vinyl alcohol units and residual vinyl acetate units. The vinyl alcohol units are relatively hydrophilic; the vinyl acetate units are relatively hydrophobic. In some instances, the sequence distribution of vinyl alcohol units and vinyl acetate units is blocky. For example, a series of vinyl alcohol units may be followed by a series of vinyl acetate units, and followed by more vinyl alcohol units to form a polymer having a mixed block-copolymer type arrangement, with units distributed in a blocky manner. In certain embodiments, the repeat units form a copolymer, e.g., a diblock, triblock, alternating, or random copolymer. Polymers other than PVA may also have these configurations of hydrophilic units and hydrophobic units.

In some embodiments, the hydrophilic units of a synthetic polymer described herein may be substantially present at the outer surface of the particle. For example, the hydrophilic units may form a majority of the outer surface of the coating and may help stabilize the particle in an aqueous solution containing the particle. The hydrophobic units may be substantially present in the interior of the coating and/or at the surface of the core particle, e.g., to facilitate attachment of the coating to the core.

The molar fraction of the relatively hydrophilic units and the relatively hydrophobic units of a synthetic polymer may be selected so as to reduce the mucoadhesion of a core and to ensure sufficient association of the polymer with the core, respectively. As described herein, the molar fraction of the hydrophobic units of the polymer may be chosen such that adequate association of the polymer with the core occurs, thereby increasing the likelihood that the polymer remains adhered to the core. The molar fraction of the relatively hydrophilic units to the relatively hydrophobic units of a synthetic polymer may be, for example, at least 0.5:1, at least 1:1, at least 2:1, at least 3:1, at least 5:1, at least 7:1, at least 10:1, at least 15:1, at least 20:1, at least 25:1, at least 30:1, at least 40:1, at least 50:1, at least 75:1, or at least 100:1. In some embodiments, the molar fraction of the relatively hydrophilic units to the relatively hydrophobic units of a synthetic polymer may be, for example, less than or equal to 100:1, less than or equal to 75:1, less than or equal to 50:1, less than or equal to 40:1, less than or equal to 30:1, less than or equal to 25:1, less than or equal to 20:1, less than or equal to 15:1, less than or equal to 10:1, less than or equal to 7:1, less than or equal to 5:1, less than or equal to 3:1, less than or equal to 2:1, or less than or equal to 1:1. Combinations of the above-referenced ranges are also possible (e.g., a ratio of at least 1:1 and less than or equal to 50:1). Other ranges are also possible.

The molecular weight of the PVA polymer may also be tailored to increase the effectiveness of the polymer to render particles mucus penetrating. Examples of PVA polymers having various molecular weights and degree of hydrolysis are shown in Table 1.

TABLE 1

Grades of PVA. The molecular weight (MW) and hydrolysis degree values were provided by the manufacturers.

| PVA acronym* | MW, kDa | Hydrolysis degree, % |
|---|---|---|
| 2K75 | 2 | 75-79 |
| 9K80 | 9-10 | 80 |
| 13K87 | 13-23 | 87-89 |
| 13K98 | 13-23 | 98 |
| 31K87 | 31-50 | 87-89 |
| 31K98 | 31-50 | 98-99 |
| 57K86 | 57-60 | 86-89 |
| 85K87 | 85-124 | 87-89 |
| 85K99 | 85-124 | 99+ |
| 95K95 | 95 | 95 |
| 105K80 | 104 | 80 |
| 130K87 | 130 | 87-89 |

*PVA acronym explanation: XXKYY, where XX stands for the PVA's lower-end molecular weight in kDa and YY stands for the PVA's lower-end hydrolysis in %.

In certain embodiments, the synthetic polymer is represented by the formula:

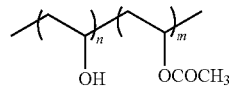

wherein n is an integer between 0 and 22730, inclusive; and m is an integer between 0 and 11630, inclusive. In certain embodiments, n is an integer between 25 and 20600, inclusive. In some embodiments, m is an integer between 5 and 1100, inclusive. In certain embodiments, m is an integer between 0 and 400 inclusive or between 1 and 400 inclusive. It is noted that n and m represent the total content of the vinyl alcohol and vinyl acetate repeat units in the polymer, respectively, rather than the block lengths.

The value of n may vary. In certain embodiments, n is at least 5, at least 10, at least 20, at least 30, at least 50, at least 100, at least 200, at least 300, at least 500, at least 800, at least 1000, at least 1200, at least 1500, at least 1800, at least 2000, at least 2200, at least 2400, at least 2600, at least 3000, at least 5000, at least 10000, at least 15000, at least 20000, or at least 25000. In some cases, n is less than or equal to 30000, less than or equal to 25000, less than or equal to 20000, less than or equal to 25000, less than or equal to 20000, less than or equal to 15000, less than or equal to 10000, less than or equal to 5000, less than or equal to 3000, less than or equal to 2800, less than or equal to 2400, less than or equal to 2000, less than or equal to 1800, less than or equal to 1500, less than or equal to 1200, less than or equal to 1000, less than or equal to 800, less than or equal to 500, less than or equal to 300, less than or equal to 200, less than or equal to 100, or less than or equal to 50. Combinations of the above-referenced ranges are also possible (e.g., n being at least 50 and less than or equal to 2000). Other ranges are also possible.

Similarly, the value of m may vary. For instance, in certain embodiments, m is at least 5, at least 10, at least 20, at least 30, at least 50, at least 70, at least 100, at least 150, at least 200, at least 250, at least 300, at least 350, at least 400, at least 500, at least 800, at least 1000, at least 1200, at least 1500, at least 1800, at least 2000, at least 2200, at least 2400, at least 2600, at least 3000, at least 5000, at least 10000, or at least 15000. In some cases, m is less than or equal to 15000, less than or equal to 10000, less than or equal to 5000, less than or equal to 3000, less than or equal to 2800, less than or equal to 2400, less than or equal to 2000, less than or equal to 1800, less than or equal to 1500, less than or equal to 1200, less than or equal to 1000, less than or equal to 800, less than or equal to 500, less than or equal to 400, less than or equal to 350, less than or equal to 300, less than or equal to 250, less than or equal to 200, less than or equal to 150, less than or equal to 100, less than or equal to 70, less than or equal to 50, less than or equal to 30, less than or equal to 20, or less than or equal to 10. Combinations of the above-referenced ranges are also possible (e.g., m being at least 5 and less than or equal to 200). Other ranges are also possible.

In some embodiments, the particles described herein include a coating comprising a block copolymer having a relatively hydrophilic block and a relatively hydrophobic block. In some cases, the hydrophilic blocks may be substantially present at the outer surface of the particle. For example, the hydrophilic blocks may form a majority of the outer surface of the coating and may help stabilize the particle in an aqueous solution containing the particle. The hydrophobic block may be substantially present in the interior of the coating and/or at the surface of the core particle, e.g., to facilitate attachment of the coating to the core. In some instances, the coating comprises a surface-altering agent including a triblock copolymer, wherein the triblock copolymer comprises a hydrophilic block—hydrophobic block—hydrophilic block configuration. Diblock copolymers having a hydrophilic block—hydrophobic block configuration are also possible. Combinations of block copolymers with other polymers suitable for use as coatings are also possible. Non-linear block configurations are also possible such as in comb, brush, or star copolymers. In some embodiments, the relatively hydrophilic block includes a synthetic polymer having pendant hydroxyl groups on the backbone of the polymer (e.g., PVA).

The molecular weight of the hydrophilic blocks and the hydrophobic blocks of the block copolymers may be selected so as to reduce the mucoadhesion of a core and to ensure sufficient association of the block copolymer with the core, respectively. The molecular weight of the hydrophobic block of the block copolymer may be chosen such that adequate association of the block copolymer with the core occurs, thereby increasing the likelihood that the block copolymer remains adhered to the core.

In certain embodiments, the combined molecular weight of the (one or more) relatively hydrophobic blocks or repeat units of a block copolymer is at least about 0.5 kDa, at least about 1 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the combined molecular weight of the (one or more) relatively hydrophobic blocks or repeat units is less than or equal to about 1000 kDa, less than or equal to about 500 kDa, less than or equal to about 200 kDa, less than or equal to about 150 kDa, less than or equal to about 140 kDa, less than or equal to about 130 kDa, less than or equal to about 120 kDa, less than or equal to about 110 kDa, less than or equal to about 100 kDa, less than or equal to about 90 kDa, less than or equal to about 80 kDa, less than or equal to about 50 kDa, less than or equal to about 20 kDa, less than or equal to about 15 kDa, less than or equal to about 13 kDa, less than or equal to about 12 kDa, less than or equal to about 10 kDa, less than or equal to about 8 kDa, or less than or equal to about 6 kDa. Combinations of the above-mentioned ranges are also possible (e.g., at least about 3 kDa and less than or equal to about 15 kDa). Other ranges are also possible.

In some embodiments, the combined (one or more) relatively hydrophilic blocks or repeat units of a block copolymer constitute at least about 15 wt %, at least about 20 wt %, at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, or at least about 70 wt % of the block copolymer. In some embodiments, the combined (one or more) relatively hydrophilic blocks or repeat units of a block copolymer constitute less than or equal to about 90 wt %, less than or equal to about 80 wt %, less than or equal to about 60 wt %, less than or equal to about 50 wt %, or less than or equal to about 40 wt % of the block copolymer. Combinations of the above-referenced ranges are also possible (e.g., at least about 30 wt % and less than or equal to about 80 wt %). Other ranges are also possible.

In some embodiments, the combined molecular weight of the (one or more) relatively hydrophilic blocks or repeat units of the block copolymer may be at least about 0.5 kDa, at least about 1 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In certain embodiments, the combined molecular weight of the (one or more) relatively hydrophilic blocks or repeat units is less than or equal to about 1000 kDa, less than or equal to about 500 kDa, less than or equal to about 200 kDa, less than or equal to about 150 kDa, less than or equal to about 140 kDa, less than or equal to about 130 kDa, less than or equal to about 120 kDa, less than or equal to about 110 kDa, less than or equal to about 100 kDa, less than or equal to about 90 kDa, less than or equal to about 80 kDa, less than or equal to about 50 kDa, less than or equal to about 20 kDa, less than or equal to about 15 kDa, less than or equal to about 13 kDa, less than or equal to about 12 kDa, less than or equal to about 10 kDa, less than or equal to about 8 kDa, less than or equal to about 6 kDa, less than or equal to about 5 kDa, less than or equal to about 3 kDa, less than or equal to about 2 kDa, or less than or equal to about 1 kDa. Combinations of the above-mentioned ranges are also possible (e.g., at least about 0.5 kDa and less than or equal to about 3 kDa). Other ranges are also possible. In embodiments in which two hydrophilic blocks flank a hydrophobic block, the molecular weights of the two hydrophilic blocks may be substantially the same or different.

In certain embodiments, the polymer of a surface-altering agent includes a polyether portion. In certain embodiments, the polymer includes a polyalkylether portion. In certain embodiments, the polymer includes polyethylene glycol tails. In certain embodiments, the polymer includes a polypropylene glycol central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a triblock copolymer of one of the polymers described herein. As disclosed herein, any recitation of PEG may be replaced with polyethylene oxide (PEO), and any recitation of PEO may be replaced with PEG. In some embodiments, a diblock or triblock copolymer comprises a synthetic polymer having pendant hydroxyl groups on the backbone of the polymer (e.g., PVA) as one or more of the blocks (with varying degrees of hydrolysis and varying molecular weights as described herein). The synthetic polymer blocks may form the central portion or the end portions of the block copolymer.

In certain embodiments, the polymer is a triblock copolymer of a polyalkyl ether (e.g., polyethylene glycol, polypropylene glycol) and another polymer (e.g., a synthetic polymer having pendant hydroxyl groups on the backbone of the polymer (e.g., PVA). In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ethers. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In some embodiments, the hydrophilic units include a synthetic polymer having pendant hydroxyl groups on the backbone of the polymer (e.g., PVA). In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. The molecular weights of the two blocks flanking the central block may be substantially the same or different.

In certain embodiments, the polymer is of the formula:

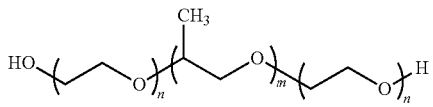

wherein n is an integer between 2 and 1140, inclusive; and m is an integer between 2 and 1730, inclusive. In certain embodiments, n is an integer between 10 and 170, inclusive. In certain embodiments, m is an integer between 5 and 70 inclusive. In certain embodiments, n is at least 2 times m, 3 times m, or 4 times m.

In certain embodiments, the coating includes a surface-altering agent comprising a (poly(ethylene glycol))-(poly(propylene oxide))-(poly(ethylene glycol)) triblock copolymer (hereinafter "PEG-PPO-PEG triblock copolymer"), present in the coating alone or in combination with another polymer such as a synthetic polymer having pendant hydroxyl groups on the backbone of the polymer (e.g., PVA). As described herein, the PEG blocks may be interchanged with PEO blocks in some embodiments. The molecular weights of the PEG (or PEO) and PPO segments of the PEG-PPO-PEG triblock copolymer may be selected so as to reduce the mucoadhesion of the particle, as described herein. Without wishing to be bound by theory, a particle having a coating comprising a PEG-PPO-PEG triblock copolymer may have reduced mucoadhesion as compared to a control particle due to, at least in part, the display of a plurality of PEG (or PEO) segments on the particle surface. The PPO segment may be adhered to the core surface (e.g., in the case of the core surface being hydrophobic), thus allowing for a strong association between the core and the triblock copolymer. In some cases, the PEG-PPO-PEG triblock copolymer is associated with the core through non-covalent interactions. For purposes of comparison, the control particle may be, for example, a carboxylate-modified polystyrene particle of similar size as the coated particle in question.

In certain embodiments, a surface-altering agent includes a polymer comprising a poloxamer, having the trade name Pluronic®. Pluronic® polymers that may be useful in the embodiments described herein include, but are not limited to, F127, F38, F108, F68, F77, F87, F88, F98, L101, L121, L31, L35, L43, L44, L61, L62, L64, L81, L92, N3, P103, P104, P105, P123, P65, P84, and P85.

Examples of molecular weights of certain Pluronic® molecules are shown in Table 2.

TABLE 2

| Molecular Weights of Pluronic ® molecules | | | | |
|---|---|---|---|---|
| Pluronic ® | Average MW | MW PPO | PEO wt % | MW PEO |
| L31 | 1000 | 900 | 10 | 100 |
| L44 | 2000 | 1200 | 40 | 800 |
| L81 | 2667 | 2400 | 10 | 267 |
| L101 | 3333 | 3000 | 10 | 333 |
| P65 | 3600 | 1800 | 50 | 1800 |
| L121 | 4000 | 3600 | 10 | 400 |
| P103 | 4286 | 3000 | 30 | 1286 |
| F38 | 4500 | 900 | 80 | 3600 |
| P123 | 5143 | 3600 | 30 | 1543 |
| P105 | 6000 | 3000 | 50 | 3000 |
| F87 | 8000 | 2400 | 70 | 5600 |
| F68 | 9000 | 1800 | 80 | 7200 |
| F127 | 12000 | 3600 | 70 | 8400 |
| P123 | 5750 | 4030 | 30 | 1730 |

Although other ranges may be possible and useful in certain embodiments described herein, in some embodiments, the hydrophobic block of the PEG-PPO-PEG triblock copolymer has one of the molecular weights described above (e.g., at least about 3 kDa and less than or equal to about 15 kDa), and the combined hydrophilic blocks have a weight percentage with respect to the polymer in one of the ranges described above (e.g., at least about 15 wt %, at least about 20 wt %, at least about 25 wt %, or at least about 30 wt %, and less than or equal to about 80 wt %). Certain Pluronic® polymers that fall within these criteria include, for example, F127, F108, P105 and P103.

Although many of the embodiments described herein involve a single coating, in other embodiments, a particle may include more than one coating (e.g., at least two, three, four, five, or more coatings), and each coating need not be formed of or comprise a mucus penetrating material. In some cases, an intermediate coating (i.e., a coating between the core surface and an outer coating) may include a polymer that facilitates attachment of an outer coating to the core surface. In many embodiments, an outer coating of a particle includes a polymer comprising a material that facilitates the transport of the particle through mucus.

As such, a coating (e.g., an inner coating, an intermediate coating, and/or an outer coating) may include any suitable polymer. In some cases, the polymer may be biocompatible and/or biodegradable. In some cases, the polymeric material may comprise more than one type of polymer (e.g., at least two, three, four, five, or more, polymers). In some cases, a polymer may be a random copolymer or a block copolymer (e.g., a diblock copolymer, a triblock copolymer) as described herein.

Non-limiting examples of suitable polymers may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone.

The molecular weight of a polymer may vary. In some embodiments, the molecular weight may be at least about 0.5 kDa, at least about 1 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight may be less than or equal to about 50 kDa, less than or equal to about 40 kDa, less than or equal to about 30 kDa, less than or equal to about 20 kDa, less than or equal to about 12 kDa, less than or equal to about 10 kDa, less than or equal to about 8 kDa, less than or equal to about 6 kDa, less than or equal to about 5 kDa, or less than or equal to about 4 kDa. Combinations of the above-referenced ranges are possible (e.g., a molecular weight of at least about 2 kDa and less than or equal to about 15 kDa). Other ranges are also possible. The molecular weight may be determined using any known technique such as light-scattering and gel permeation chromatography. Other methods are known in the art.

In certain embodiments, the polymer is biocompatible, i.e., the polymer does not typically induce an adverse response when inserted or injected into a living subject; for example, it does not include significant inflammation and/or acute rejection of the polymer by the immune system, for instance, via a T-cell-mediated response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically does not result in significant cell death at moderate concentrations, e.g., at concentrations of about 50 micrograms/$10^6$ cells. For instance, a biocompatible polymer may cause less than about 20% cell death when exposed to cells such as fibroblasts or epithelial cells, even if phagocytosed or otherwise uptaken by such cells. In some embodiments, a substance is "biocompatible" if its addition to cells in vitro results in less than or equal to 20% cell death, and their administration in vivo does not induce unwanted inflammation or other such adverse effects.

In certain embodiments, a biocompatible polymer may be biodegradable, i.e., the polymer is able to degrade, chemically and/or biologically (e.g., by the cellular machinery or by hydrolysis), within a physiological environment, such as within the body or when introduced to cells. For instance, the polymer may be one that hydrolyzes spontaneously upon exposure to water (e.g., within a subject), and/or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymer may be biologically degraded, e.g., by enzymatic activity or cellular machinery, in some cases, for example, through exposure to a lysozyme (e.g., having relatively low pH). In some cases, the polymer may be broken down into monomers and/or other nonpolymeric moieties that cells can either reuse or dispose of without significant toxic effect on the cells (i.e., fewer than about 20% of the cells are killed when the components are added to cells in vitro). For example, polylactide may be hydrolyzed to form lactic acid, polyglycolide may be hydrolyzed to form glycolic acid, etc.).

Examples of biodegradable polymers include, but are not limited to, poly(ethylene glycol)-poly(propylene oxide)-poly(ethylene glycol) triblock copolymers, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In certain embodiments, a polymer may biodegrade within a period that is acceptable in the desired application. In certain embodiments, such as in vivo therapy, such degradation occurs in a period usually less than about five years, one year, six months, three months, one month, fifteen days, five days, three days, or even one day or less (e.g., 1-4 hours, 4-8 hours, 4-24 hours, 1-24 hours) on exposure to a physiological solution with a pH between 6 and 8 having a temperature of between 25 and 37° C. In other embodiments, the polymer degrades in a period of between about one hour and several weeks, depending on the desired application.

Although coatings and particles described herein may include polymers, in some embodiments, the particles described herein comprise a hydrophobic material that is not a polymer (e.g., a non-polymer) and is not a pharmaceutical agent. For example, all or portions of a particle may be coated with a passivating layer in some embodiments. Non-limiting examples of non-polymeric materials may include certain metals, waxes, and organic materials (e.g., organic silanes, perfluorinated or fluorinated organic materials).

Particles with Reduced Mucoadhesion

As described herein, in some embodiments, a method involves identifying a material such as a particle to which it is desired that its mucoadhesiveness be reduced. Materials in need of increased diffusivity through mucus may be, for example, hydrophobic, have many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles herein described as having reduced mucoadhesion may alternatively be characterized as having increased transport through mucus, being mobile in mucus, or mucus-penetrating (i.e., mucus-penetrating particles), meaning that the particles are transported through mucus faster than a (negative) control particle. The (negative) control particle may be a particle that is known to be mucoadhesive, e.g., an unmodified particle or core that is not coated with a coating described herein, such as a 200 nm carboxylated polystyrene particle.

In certain embodiments, methods herein include preparing a pharmaceutical composition or formulation of the modified substance, e.g., in a formulation adapted for delivery (e.g., topical delivery) to mucus or a mucosal surface of a subject. The pharmaceutical composition with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion. As will be known by those of ordinary skill in the art, mucus is a viscoelastic and adhesive substance that traps most foreign particles. Trapped particles are not able to reach the underlying epithelium and/or are quickly eliminated by mucus clearance mechanisms. For a particle to reach the underlying epithelium and/or for a particle to have prolonged retention in the mucosal tissue, the particle must quickly penetrate mucus secretions and/or avoid the mucus clearance mechanisms. If a particle does not adhere substantially to the mucus, the particle may be able to diffuse in the interstitial fluids between mucin fibers and reach the underlying epithelium and/or not be eliminated by the mucus clearance mechanisms. Accordingly, modifying mucoadhesive materials, (e.g., pharmaceutical agents that are hydrophobic) with a material to reduce the mucoadhesion of the particle may allow for efficient delivery of the particles to the underlying epithelium and/or prolonged retention at mucosal surfaces.

Furthermore, in some embodiments, the particles described herein having reduced mucoadhesion facilitate better distribution of the particles at a tissue surface, and/or have a prolonged presence at the tissue surface, compared to particles that are more mucoadhesive. For example, in some cases a luminal space such as the gastrointestinal tract is surrounded by a mucus-coated surface. Mucoadhesive particles delivered to such a space are typically removed from the luminal space and from the mucus-coated surface by the body's natural clearance mechanisms. The particles described herein with reduced mucoadhesion may remain in the luminal space for relatively longer periods compared to the mucoadhesive particles. This prolonged presence may prevent or reduce clearance of the particles, and/or may allow for better distribution of the particles on the tissue surface. The prolonged presence may also affect the particle transport through the luminal space, e.g., the particles may distribute into the mucus layer and may reach the underlying epithelium.

In certain embodiments, a material (e.g., a core) coated with a polymer described herein may pass through mucus or a mucosal barrier in a subject, and/or exhibit prolonged retention and/or increase uniform distribution of the particles at mucosal surfaces, e.g., such substances are cleared more slowly (e.g., at least 2 times, 5 times, 10 times, or even at least 20 times more slowly) from a subject's body as compared to a (negative) control particle. The (negative) control particle may be a particle that is known to be mucoadhesive, e.g., an unmodified particle or core that is not coated with a coating described herein, such as a 200 nm carboxylated polystyrene particle.

In certain embodiments, a particle described herein has certain a relative velocity, $<V_{mean}>_{rel}$, which is defined as follows:

$$<V_{mean}>_{rel} = \frac{<V_{mean}>_{Sample} - <V_{mean}>_{Negative\ control}}{<V_{mean}>_{Positive\ control} - <V_{mean}>_{Negative\ control}} \quad \text{(Equation 1)}$$

where $<V_{mean}>$ is the ensemble average trajectory-mean velocity, $V_{mean}$ is the velocity of an individual particle averaged over its trajectory, the sample is the particle of interest, the negative control is a 200 nm carboxylated polystyrene particle, and the positive control is a 200 nm polystyrene particle densely PEGylated with 2 kDa-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative and positive controls may be fluorescent particles to observe tracking. Alternatively non-fluorescent particles may be coated with a fluorescent molecule, a fluorescently tagged surface agent or a fluorescently tagged polymer. An advanced image processing software (e.g., Image Pro or MetaMorph) can be used to measure individual trajectories of multiple particles over a time-scale of at least 3.335 s (50 frames).

In some embodiments, a particle described herein has a relative velocity of greater than about 0.3, greater than about 0.4, greater than about 0.5, greater than about 0.6, greater than about 0.7, greater than about 0.8, greater than about 0.9, greater than about 1.0, greater than about 1.1, greater than about 1.2, greater than about 1.3, greater than about 1.4, greater than about 1.5, greater than about 1.6, greater than about 1.7, greater than about 1.8, greater than about 1.9 or greater than about 2.0 in mucus. In some embodiments, a particle described herein has a relative velocity of less than or equal to about 10.0, less than or equal to about 8.0, less than or equal to about 6.0, less than or equal to about 4.0, less than or equal to about 3.0, less than or equal to about 2.0, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.1, less than or equal to about 1.0, less than or equal to about 0.9, less than or equal to about 0.8, or less than or equal to about 1.7 in mucus. Combinations of the above-noted ranges are possible (e.g., a relative velocity of greater than about 0.5 and less than or equal to about 6.0). Other ranges are also possible. The mucus may be, for example, human cervicovaginal mucus.

In certain embodiments, a particle described herein can diffuse through mucus or a mucosal barrier at a greater rate or diffusivity than a control particle or a corresponding particle (e.g., a corresponding particle that is unmodified and/or is not coated with a coating described herein). In some cases, a particle described herein may pass through mucus or a mucosal barrier at a rate of diffusivity that is at least about 10 times, 20 times, 30 times, 50 times, 100 times, 200 times, 500 times, 1000 times, 2000 times, 5000 times, 10000 times, or more, higher than a control particle or a corresponding particle. In some cases, a particle described herein may pass through mucus or a mucosal barrier at a rate of diffusivity that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

For the purposes of the comparisons described herein, the corresponding particle may be approximately the same size, shape, and/or density as the test particle but lacking the coating that makes the test particle mobile in mucus. In some cases, the measurement is based on a time scale of about 1 second, or about 0.5 second, or about 2 seconds, or about 5 seconds, or about 10 seconds. Those of ordinary skill in the art will be aware of methods for determining the geometric mean square displacement and rate of diffusivity.

In addition, a particle described herein may pass through mucus or a mucosal barrier with a geometric mean squared displacement that is at least about 10 times, 20 times, 30 times, 50 times, 100 times, 200 times, 500 times, 1000 times, 2000 times, 5000 times, 10000 times, or more, higher than a corresponding particle or control particle. In some cases, a particle described herein may pass through mucus or a mucosal barrier with a geometric mean squared displacement that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

In some embodiments, a particle described herein diffuses through a mucosal barrier at a rate approaching the rate or diffusivity at which said particles can diffuse through water. In some cases, a particle described herein may pass through a mucosal barrier at a rate or diffusivity that is less than or equal to about 1/100, less than or equal to about 1/200, less than or equal to about 1/300, less than or equal to about 1/400, less than or equal to about 1/500, less than or equal to about 1/600, less than or equal to about 1/700, less than or equal to about 1/800, less than or equal to about 1/900, less than or equal to about 1/1000, less than or equal to about 1/2000, less than or equal to about 1/5000, less than or equal to about 1/10,000 the diffusivity that the particle diffuse through water under identical conditions. In some cases, a particle described herein may pass through a mucosal barrier at a rate or diffusivity that is greater than about 1/10,000, greater than about 1/5000, greater than about 1/2000, greater than about 1/1000, greater than about 1/900, greater than about 1/800, greater than about 1/700, greater than about 1/600, greater than about 1/500, greater than about 1/400, greater than about 1/300, greater than about 1/200, greater than about 1/100 the diffusivity that the particle diffuse through water under identical conditions. Combinations of the above-referenced ranges are also possible (e.g., greater than about 1/5000 and less than 1/500 the diffusivity that the particle diffuse through water under identical conditions). Other ranges are also possible. The measurement may be based on a time scale of about 1 second, or about 0.5 second, or about 2 seconds, or about 5 seconds, or about 10 seconds.

In a particular embodiment, a particle described herein may diffuse through human cervicovaginal mucus at a diffusivity that is less than about 1/500 the diffusivity that the particle diffuses through water. In some cases, the measurement is based on a time scale of about 1 second, or about 0.5 second, or about 2 seconds, or about 5 seconds, or about 10 seconds.

In certain embodiments, the present invention provides particles that travel through mucus, such as human cervicovaginal mucus, at certain absolute diffusivities. For example, the particles of described herein may travel at diffusivities of at least about $1 \times 10^{-4}$ μm/s, $2 \times 10^{-4}$ μm/s, $5 \times 10^{-4}$ μm/s, $1 \times 10^{-3}$ μm/s, $2 \times 10^{-3}$ μm/s, $5 \times 10^{-3}$ μm/s, $1 \times 10^{-2}$ μm/s, $2\times10^{-2}$ µm/s, $4\times10^{-2}$ µm/s, $5\times10^{-2}$ µm/s, $6\times10^{-2}$ µm/s, $8\times10^{-1}$ µm/s, $1\times10^{-1}$ µm/s, $2\times10^{-1}$ µm/s, $5\times10^{-1}$ µm/s, 1 µm/s, or 2 µm/s. In some cases, the particles may travel at diffusivities of less than or equal to about 2 µm/s, less than or equal to about 1 µm/s, less than or equal to about $5\times10^{-1}$ µm/s, less than or equal to about $2\times10^{-1}$ µm/s, less than or equal to about $1\times10^{-1}$ µm/s, less than or equal to about $8\times10^{-2}$ µm/s, less than or equal to about $6\times10^{-2}$ µm/s, less than or equal to about $5\times10^{-2}$ µm/s, less than or equal to about $4\times10^{-2}$ µm/s, less than or equal to about $2\times10^{-2}$ µm/s, less than or equal to about $1\times10^{-2}$ µm/s, less than or equal to about $5\times10^{-3}$ µm/s, less than or equal to about $2\times10^{-3}$ µm/s, less than or equal to about $1\times10^{-3}$ µm/s, less than or equal to about $5\times10^{-4}$ µm/s, less than or equal to about $2\times10^{-4}$ µm/s, or less than or equal to about $1\times10^{-4}$ µm/s. Combinations of the above-referenced ranges are also possible (e.g., greater than about $2\times10^{-4}$ µm/s and less than or equal to about $1\times10^{-1}$ µm/s). Other ranges are also possible. In some cases, the measurement is based on a time scale of about 1 second, or about 0.5 second, or about 2 seconds, or about 5 seconds, or about 10 seconds.

It should be appreciated that while many of the mobilities (e.g., relative velocities, diffusivities) described here may be measured in human cervicovaginal mucus, they may be measured in other types of mucus as well.

In certain embodiments, a particle described herein comprises surface-altering moieties at a given density. The surface-altering moieties may be the portions of a surface-altering agent that are, for example, exposed to the solvent containing the particle. As an example, the hydrolyzed units/blocks of PVA may be surface-altering moieties of the surface-altering agent PVA. In some cases, the surface-altering moieties and/or surface-altering agents are present at a density of at least about 0.001 units or molecules per $nm^2$, at least about 0.002, at least about 0.005, at least about 0.01, at least about 0.02, at least about 0.05, at least about 0.1, at least about 0.2, at least about 0.5, at least about 1, at least about 2, at least about 5, at least about 10, at least about 20, at least about 50, at least about 100 units or molecules per $nm^2$, or more units or molecules per $nm^2$. In some cases, the surface-altering moieties and/or surface-altering agents are present at a density of less than or equal to about 100 units or molecules per $nm^2$, less than or equal to about 50, less than or equal to about 20, less than or equal to about 10, less than or equal to about 5, less than or equal to about 2, less than or equal to about 1, less than or equal to about 0.5, less than or equal to about 0.2, less than or equal to about 0.1, less than or equal to about 0.05, less than or equal to about 0.02, or less than or equal to about 0.01 units or molecules per $nm^2$. Combinations of the above-referenced ranges are possible (e.g., a density of at least about 0.01 and less than or equal to about 1 units or molecules per $nm^2$). Other ranges are also possible.

Those of ordinary skill in the art will be aware of methods to estimate the average density of surface-altering moieties (see, for example, S. J. Budijono et al., Colloids and Surfaces A: Physicochem. Eng. Aspects 360 (2010) 105-110 and Joshi, et al., *Anal. Chim. Acta* 104 (1979) 153-160, each of which is incorporated herein by reference). For example, as described herein, the average density of surface-altering moieties can be determined using HPLC quantitation and DLS analysis. A suspension of particles for which surface density determination is of interest is first sized using DLS: a small volume is diluted to an appropriate concentration (~100 µg/mL, for example), and the z-average diameter is taken as a representative measurement of particle size. The remaining suspension is then divided into two aliquots. Using HPLC, the first aliquot is assayed for the total concentration of core material and for the total concentration of surface-altering moiety. Again using HPLC the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

In certain embodiments, the particles described herein comprise surface-altering moieties and/or agents that affect the zeta-potential of the particle. The zeta potential of the coated particle may be, for example, at least about −100 mV, at least about −75 mV, at least about −50 mV, at least about −40 mV, at least about −30 mV, at least about −20 mV, at least about −10 mV, at least about −5 mV, at least about 5 mV, at least about 10 mV, at least about 20 mV, at least about 30 mV, at least about 40 mV, at least about 50 mV, at least about 75 mV, or at least about 100 mV. Combinations of the above-referenced ranges are possible (e.g., a zeta-potential of at least about −50 mV and less than or equal to about 50 mV). Other ranges are also possible.

The coated particles described herein may have any suitable shape and/or size. In some embodiments, a coated particle has a shape substantially similar to the shape of the core. In some cases, a coated particle described herein may be a nanoparticle, i.e., the particle has a characteristic dimension of less than about 1 micrometer, where the characteristic dimension of the particle is the diameter of a perfect sphere having the same volume as the particle. In other embodiments, larger sizes are possible (e.g., about 1-10 microns). A plurality of particles, in some embodiments, may also be characterized by an average size (e.g., an average largest cross-sectional dimension, or an average smallest cross-sectional dimension for the plurality of particles). A plurality of particles may have an average size of, for example, less than or equal to about 10 µm, less than or equal to about 5 µm, less than or equal to about 1 µm, less than or equal to about 800 nm, less than or equal to about 700 nm, less than or equal to about 500 nm, less than or equal to 400 nm, less than or equal to about 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, a plurality of particles may have an average size of, for example, at least about 5 nm, at least about 20 nm, at least about 50 nm, at least about 100 nm, at least about 200 nm, at least about 300 nm, at least about 400 nm, at least about 500 nm, at least about 1 µm, at least or at least about 5 μm. Combinations of the above-referenced ranges are also possible (e.g., an average size of at least about 50 nm and less than about 500 nm). Other ranges are also possible. In some embodiments, the sizes of the cores formed by a process described herein have a Gaussian-type distribution.

Pharmaceutical Agents

In some embodiments, a coated particle comprises at least one pharmaceutical agent. The pharmaceutical agent may be present in the core of the particle and/or present in a coating of the particle (e.g., dispersed throughout the core and/or coating). In some cases, a pharmaceutical agent may be disposed on the surface of the particle (e.g., on an outer surface of a coating, the inner surface of a coating, on a surface of the core). The pharmaceutical agent may be contained within a particle and/or disposed in a portion of the particle using commonly known techniques (e.g., by coating, adsorption, covalent linkage, encapsulation, or other process). In some cases, the pharmaceutical agent may be present in the core of the particle prior to or during coating of the particle. In some cases, the pharmaceutical agent is present during the formation of the core of the particle, as described herein.

Non-limiting examples of pharmaceutical agents include imaging agents, diagnostic agents, therapeutic agents, agents with a detectable label, nucleic acids, nucleic acid analogs, small molecules, peptidomimetics, proteins, peptides, lipids, vaccines, viral vectors, virus, and surfactants.

In some embodiments, a pharmaceutical agent contained in a particle described herein has a therapeutic, diagnostic, or imaging effect in a mucosal tissue to be targeted. Non-limiting examples of mucosal tissues include oral (e.g., including the buccal and esophagal membranes and tonsil surface), ophthalmic, gastrointestinal (e.g., including stomach, small intestine, large intestine, colon, rectum), nasal, respiratory (e.g., including nasal, pharyngeal, tracheal and bronchial membranes), and genital (e.g., including vaginal, cervical and urethral membranes) tissues.

Any suitable number of pharmaceutical agents may be present in a particle described herein. For example, at least 1, at least 2, at least 3, at least 4, at least 5, or more, but generally less than 10, pharmaceutical agents may be present in a particle described herein.

A number of drugs that are mucoadhesive are known in the art and may be used as pharmaceutical agents in the particles described herein (see, for example, Khanvilkar K, Donovan M D, Flanagan D R, Drug transfer through mucus, Advanced Drug Delivery Reviews 48 (2001) 173-193; Bhat P G, Flanagan D R, Donovan M D. Drug diffusion through cystic fibrotic mucus: steady-state permeation, rheologic properties, and glycoprotein morphology, J Pharm Sci, 1996 June; 85(6):624-30). Additional non-limiting examples of pharmaceutical agents include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents, chemotactic agents and chemoattractants, peptides that modulate cell adhesion and/or cell mobility, cell permeabilizing agents, vaccine potentiators, inhibitors of multidrug resistance and/or efflux pumps, etc.).

Additional non-limiting examples of pharmaceutical agents include aloxiprin, auranofin, azapropazone, benorylate, diflunisal, etodolac, fenbufen, fenoprofen calcim, flurbiprofen, furosemide, ibuprofen, indomethacin, ketoprofen, loteprednol etabonate, meclofenamic acid, mefenamic acid, nabumetone, naproxen, oxyphenbutazone, phenylbutazone, piroxicam, sulindac, albendazole, bephenium hydroxynaphthoate, cambendazole, dichlorophen, ivermectin, mebendazole, oxamniquine, oxfendazole, oxantel embonate, praziquantel, pyrantel embonate, thiabendazole, amiodarone HCl, disopyramide, flecainide acetate, quinidine sulphate. Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, dicoumarol, dipyridamole, nicoumalone, phenindione, amoxapine, maprotiline HCl, mianserin HCL, nortriptyline HCl, trazodone HCL, trimipramine maleate, acetohexamide, chlorpropamide, glibenclamide, gliclazide, glipizide, tolazamide, tolbutamide, beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid, amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid, allopurinol, probenecid, sulphin-pyrazone, amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL, amodiaquine, chloroquine, chlorproguanil HCl, halofantrine HCl, mefloquine HCl, roguanil HCl, pyrimethamine, quinine sulphate, dihydroergotamine mesylate, ergotamine tartrate, methysergide maleate, pizotifen maleate, sumatriptan succinate, atropine, benzhexol HCl, biperiden, ethopropazine HCl, hyoscyamine, mepenzolate bromide, oxyphencylcimine HCl, tropicamide, aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone, benznidazole, clioquinol, decoquinate, diiodohydroxyquinoline, diloxanide furoate, dinitolmide, furzolidone, metronidazole, nimorazole, nitrofurazone, ornidazole, tinidazole, carbimazole, propylthiouracil, alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone, acebutolol, alprenolol, atenolol, labetalol, metoprolol, nadolol, oxprenolol, pindolol, propranolol, amrinone, digitoxin, digoxin, enoximone, lanatoside C, medigoxin, beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone, acetazolamide, amiloride, bendrofluazide, bumetanide, chlorothiazide, chlorthalidone, ethacrynic acid, frusemide, metolazone, spironolactone, triamterene, bromocriptine mesylate, lysuride maleate, bisacodyl, cimetidine, cisapride, diphenoxylate HCl, domperidone, famotidine, loperamide, mesalazine, nizatidine, omeprazole, ondansetron HCL, ranitidine HCl, sulphasalazine, acrivastine, astemizole, cinnarizine, cyclizine, cyproheptadie HCl, dimenhydrinate, flunarizine HCl, loratadine, meclozine HCl, oxatomide, terfenadine, bezafibrate, clofibrate, fenofibrate, gemfibrozil, probucol, amyl nitrate, glyceryl trinitrate, isosorbide dinitrate, isosorbide mononitrate, pentaerythritol tetranitrate, betacarotene, vitamin A, vitamin B 2, vitamin D, vitamin E, vitamin K, codeine, dextropropyoxyphene, diamorphine, dihydrocodeine, meptazinol, methadone, morphine, nalbuphine, pentazocine, clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone, amphetamine, dexamphetamine, dexfenfluramine, fenfluramine, and mazindol.

Uses and Pharmaceutical Compositions

The particles described herein may be employed in any suitable application. In some cases, the particles are part of pharmaceutical compositions (e.g., as described herein), for example, those used to deliver a pharmaceutical agent (e.g., a drug, therapeutic agent, diagnostic agent, imaging agent) through or to mucus or a mucosal surface. A pharmaceutical composition may comprise at least one particle described herein and one or more pharmaceutically acceptable excipients or carriers. The composition may be used in treating, preventing, and/or diagnosing a condition in a subject, wherein the method comprises administering to a subject the pharmaceutical composition. A subject or patient to be treated by the articles and methods described herein may mean either a human or non-human animal, such as primates, mammals, and vertebrates.

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an analgesic agent even though such agent does not treat the cause of the pain).

In some embodiments, a pharmaceutical composition described herein is delivered to a mucosal surface in a subject and may pass through a mucosal barrier in the subject (e.g., mucus), and/or may exhibit prolonged retention and/or increased uniform distribution of the particles at mucosal surfaces, e.g., due to reduced mucoadhesion. Non-limiting examples of mucosal tissues include oral (e.g., including the buccal and esophagal membranes and tonsil surface), ophthalmic, gastrointestinal (e.g., including stomach, small intestine, large intestine, colon, rectum), nasal, respiratory (e.g., including nasal, pharyngeal, tracheal and bronchial membranes), genital (e.g., including vaginal, cervical and urethral membranes).

Pharmaceutical compositions described herein and for use in accordance with the articles and methods described herein may include a pharmaceutically acceptable excipient or carrier. A pharmaceutically acceptable excipient or pharmaceutically acceptable carrier may include a non-toxic, inert solid, semi-solid or liquid filler, diluent, encapsulating material or formulation auxiliary of any suitable type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on the route of administration as described below, the pharmaceutical agent being delivered, time course of delivery of the agent, etc.

Pharmaceutical compositions containing the particles described herein may be administered to a subject via any route known in the art. These include, but are not limited to, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), buccal and inhalational administration. In some embodiments, compositions described herein may be administered parenterally as injections (intravenous, intramuscular, or subcutaneous), drop infusion preparations, or suppositories. As would be appreciated by one of skill in this art, the route of administration and the effective dosage to achieve the desired biological effect may be determined by the agent being administered, the target organ, the preparation being administered, time course of administration, disease being treated, intended use, etc.

As an example, the particles may be included in a pharmaceutical composition to be formulated as a nasal spray, such that the pharmaceutical composition is delivered across a nasal mucus layer. As another example, the particles may be included in a pharmaceutical composition to be formulated as an inhaler, such that the pharmaceutical compositions is delivered across a pulmonary mucus layer. As another example, if compositions are to be administered orally, it may be formulated as tablets, capsules, granules, powders, or syrups. Similarly, the particles may be included in a pharmaceutical composition that is to be delivered via ophthalmic, gastrointestinal, nasal, respiratory, rectal, urethral and/or vaginal tissues.

For application by the ophthalmic mucous membrane route, subject compositions may be formulated as eye drops or eye ointments. These formulations may be prepared by conventional means, and, if desired, the subject compositions may be mixed with any conventional additive, such as a buffering or pH-adjusting agents, tonicity adjusting agents, viscosity modifiers, suspension stabilizers, preservatives, and other pharmaceutical excipients. In addition, in certain embodiments, subject compositions described herein may be lyophilized or subjected to another appropriate drying technique such as spray drying.

In some embodiments, particles described herein that may be administered in inhalant or aerosol formulations comprise one or more pharmaceutical agents, such as adjuvants, diagnostic agents, imaging agents, or therapeutic agents useful in inhalation therapy. The particle size of the particulate medicament should be such as to permit inhalation of substantially all of the medicament into the lungs upon administration of the aerosol formulation and may be, for example, less than about 20 microns, e.g., in the range of about 1 to about 10 microns, e.g., about 1 to about 5 microns, although other ranges are also possible. The particle size of the medicament may be reduced by conventional means, for example by milling or micronisation. Alternatively, the particulate medicament can be administered to the lungs via nebulization of a suspension. The final aerosol formulation may contain, for example, between 0.005-90% w/w, between 0.005-50%, between 0.005-10%, between about 0.005-5% w/w, or between 0.01-1.0% w/w, of medicament relative to the total weight of the formulation. Other ranges are also possible.

It is desirable, but by no means required, that the formulations described herein contain no components which may provoke the degradation of stratospheric ozone. In particular, in some embodiments, propellants are selected that do not contain or do not consist essentially of chlorofluorocarbons such as $CCl_3F$, $CCl_2F_2$, and $CF_3CCl_3$.

The aerosol may comprise propellant. The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol, and propylene glycol, preferably ethanol. In general, only small quantities of polar adjuvants (e.g., 0.05-3.0% w/w) may be required to improve the stability of the dispersion—the use of quantities in excess of 5% w/w may tend to dissolve the medicament. Formulations in accordance with the embodiments described herein may contain less than 1% w/w, e.g., about 0.1% w/w, of polar adjuvant. However, the formulations described herein may be substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example, up to 30% w/w of a volatile saturated $C_1$-$C_6$ hydrocarbon. Optionally, the aerosol formulations according to the invention may further comprise one or more surfactants. The surfactants can be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

The formulations described herein may be prepared by dispersal of the particles in the selected propellant and/or co-propellant in an appropriate container, e.g., with the aid of sonication. The particles may be suspended in co-propellant and filled into a suitable container. The valve of the container is then sealed into place and the propellant introduced by pressure filling through the valve in the conventional manner. The particles may be thus suspended or dissolved in a liquified propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the particles (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the particles. Ordinarily, an aqueous aerosol is made by formulating an aqueous solution or suspension of the particles together with conventional pharmaceutically acceptable carriers and stabilizers. The carriers and stabilizers vary with the requirements of the particular composition, but typically include non-ionic surfactants (Tweens, Pluronic®, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration can be suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles described herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles described herein, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

The particles described herein comprising a pharmaceutical agent may be administered to a subject to be delivered in an amount sufficient to deliver to a subject a therapeutically effective amount of an incorporated pharmaceutical agent as part of a diagnostic, prophylactic, or therapeutic treatment. In general, an effective amount of a pharmaceutical agent or component refers to the amount necessary to elicit the desired biological response. The desired concentration of pharmaceutical agent in the particle will depend on numerous factors, including, but not limited to, absorption, inactivation, and excretion rates of the drug as well as the delivery rate of the compound from the subject compositions, the desired biological endpoint, the agent to be delivered, the target tissue, etc. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The concentration and/or amount of any pharmaceutical agent to be administered to a subject may be readily determined by one of ordinary skill in the art. Known methods are also available to assay local tissue concentrations, diffusion rates from particles and local blood flow before and after administration of the therapeutic formulation.

The compositions and/or formulations described herein may have any suitable osmolarity. In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, or at least about 310 mOsm/L. In certain embodiments, a composition and/or formulation described herein may have an osmolarity of less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible. The osmolarity of the composition and/or formulation can be varied by changing, for example, the concentration of salts present in the solvent of the composition and/or formulation.

These and other aspects of the present invention will be further appreciated upon consideration of the following Examples, which are intended to illustrate certain particular embodiments of the invention but are not intended to limit its scope, as defined by the claims.

EXAMPLES

Example 1

The following describes a non-limiting example of a method of forming mucus-penetrating particles from prefabricated polymeric particles by physical adsorption of certain poly(vinyl alcohol) polymers (PVA). Carboxylated polystyrene nanoparticles (PSCOO) were used as the prefabricated particle/core particle with a well-established strongly mucoadhesive behavior. The PVAs acted as surface-altering agents forming coatings around the core particles. PVA of various molecular weights (MW) and hydrolysis degrees were evaluated to determine effectiveness of the coated particles in penetrating mucus.

PSCOO particles were incubated in aqueous solution in the presence of various PVA polymers to determine whether certain PVAs can physically (non-covalently) coat the core particle with a mucoinert coating that would minimize particle interactions with mucus constituents and lead to rapid particle penetration in mucus. In these experiments, the PVA acted as a coating around the core particles, and the resulting particles were tested for their mobility in mucus, although in other embodiments, PVA may be exchanged with other surface-altering agents that can increase mobility of the particles in mucus. The PVAs tested ranged in the average molecular weight from 2 kDa to 130 kDa and in the average hydrolysis degree from 75% to 99+%. The PVAs that were tested are listed in Table 1, shown above.

The particle modification process was as follows: 200 nm carboxylated-modified red fluorescent polystyrene nanoparticles (PSCOO) were purchased from Invitrogen. The PSCOO particles (0.4-0.5% wt) were incubated in an aqueous PVA solution (0.4-0.5% wt) for at least 1 hour at room temperature.

The mobility and distribution of the modified nanoparticles in human cervicovaginal mucus (CVM) were characterized using fluorescence microscopy and multiple particle tracking software. In a typical experiment, ≤0.5 µL of an incubated nanosuspension (diluted ~10× with 0.5% wt aqueous solution of a corresponding PVA) was added to 20 µl of fresh CVM along with controls. Conventional nanoparticles (200 nm blue fluorescent carboxylate-modified polystyrene microspheres from Invitrogen) were used as a negative control to confirm the barrier properties of the CVM samples. Yellow-green fluorescent polystyrene nanoparticles covalently coated with PEG 2 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (observed through a Texas Red filter set), negative control (observed through a DAPI filter set), and positive control (observed through a FITC filter set). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, ensemble-average (absolute) velocity is then converted to relative sample velocity $<V_{mean}>_{rel}$ according to the formula shown in Equation 1. Multiple particle tracking confirmed that in all tested CVM samples the negative controls were constrained, while the positive controls were mobile as demonstrated by the differences in $<V_{mean}>$ for the positive and negative controls (Table 3).

TABLE 3

Transport of nanoparticles incubated with various PVA (sample) and controls in CVM: Ensemble-average velocity $<V_{mean}>$ (µm/s) and relative sample velocity $<V_{mean}>_{rel}$

| Stabilizer/Surface-altering agent | Negative Control $<V_{mean}>$ | SD | Positive Control $<V_{mean}>$ | SD | Sample $<V_{mean}>$ | SD | Sample (relative) $<V_{mean}>_{rel}$ | SD |
|---|---|---|---|---|---|---|---|---|
| PVA2K75   | 1.39 | 0.33 | 3.3  | 0.68 | 3.44 | 0.7  | 1.07  | 0.59  |
| PVA9K80   | 0.4  | 0.08 | 5.13 | 1.16 | 4.88 | 1.74 | 0.95  | 0.44  |
| PVA13K87  | 0.56 | 0.61 | 5.23 | 1.24 | 4.92 | 1.77 | 0.93  | 0.49  |
| PVA31K87  | 0.53 | 0.63 | 4.48 | 1.38 | 3.69 | 1.94 | 0.80  | 0.60  |
| PVA57K86  | 0.5  | 0.25 | 5.74 | 1.11 | 4.76 | 0.91 | 0.81  | 0.25  |
| PVA85K87  | 0.29 | 0.28 | 4.25 | 0.97 | 4.01 | 0.71 | 0.94  | 0.31  |
| PVA105K80 | 0.98 | 0.52 | 5.44 | 0.86 | 4.93 | 0.66 | 0.89  | 0.27  |
| PVA130K87 | 1.41 | 0.56 | 3.75 | 0.82 | 3.57 | 0.6  | 0.92  | 0.53  |
| PVA95K95  | 0.51 | 0.36 | 3.19 | 0.68 | 0.45 | 0.19 | −0.02 | −0.15 |
| PVA13K98  | 0.43 | 0.17 | 3.42 | 1.65 | 0.5  | 0.76 | 0.02  | 0.26  |
| PVA31K98  | 0.41 | 0.23 | 6.03 | 1.19 | 0.26 | 0.14 | −0.03 | −0.05 |
| PVA85K99  | 0.28 | 0.1  | 4.7  | 0.82 | 0.53 | 0.77 | 0.06  | 0.18  |

Figure 2A:
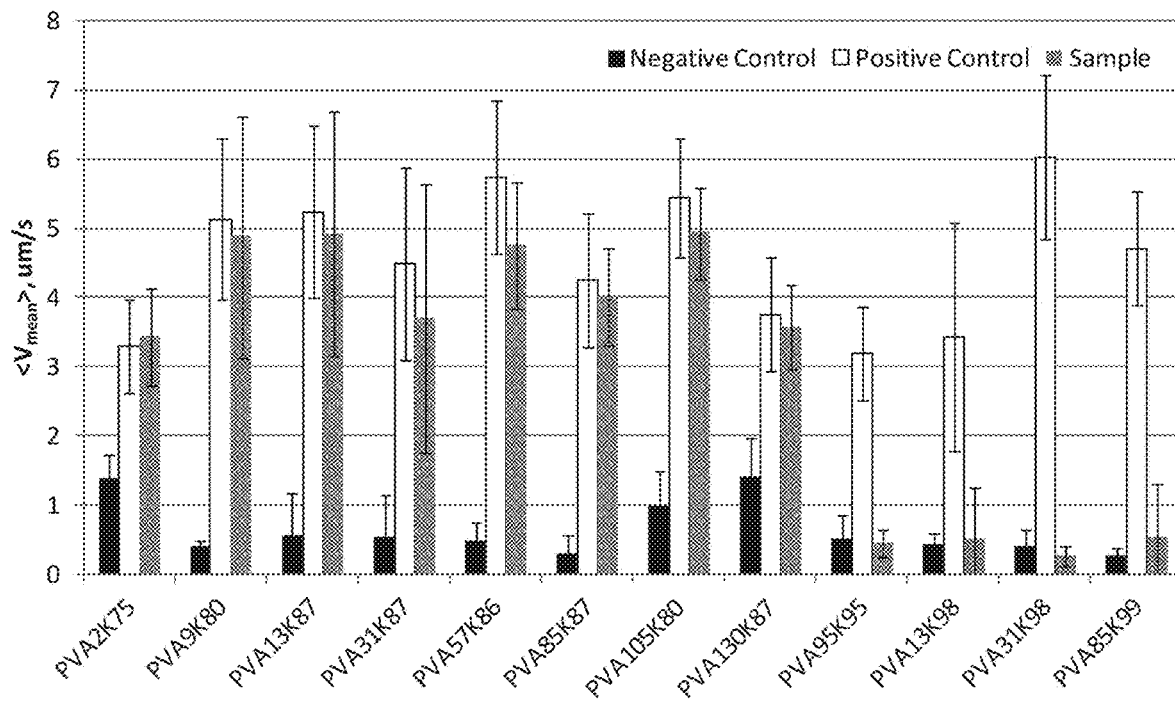
FIG. 2A is a plot showing the ensemble averaged velocity $<V_{mean}>$ in human cervicovaginal mucus (CVM) for PSCOO particles coated with various poly(vinyl alcohols) (PVAs) according to one set of embodiments.

It was discovered that nanoparticles incubated in the presence of certain (but, interestingly, not all) PVA transported through CVM at the same rate or nearly the same velocity as the positive control. Specifically, the particles stabilized with PVA2K75, PVA9K80, PVA13K87, PVA31K87, PVA57K86, PVA85K87, PVA105K80, and PVA130K87 exhibited $<V_{mean}>$ that significantly exceeded those of the negative controls and were indistinguishable, within experimental error, from those of the positive controls. The results are shown in Table 3 and FIG. 2A. For these samples, $<V_{mean}>_{rel}$ values exceeded 0.5, as shown in FIG. 2B.

Figure 2B:
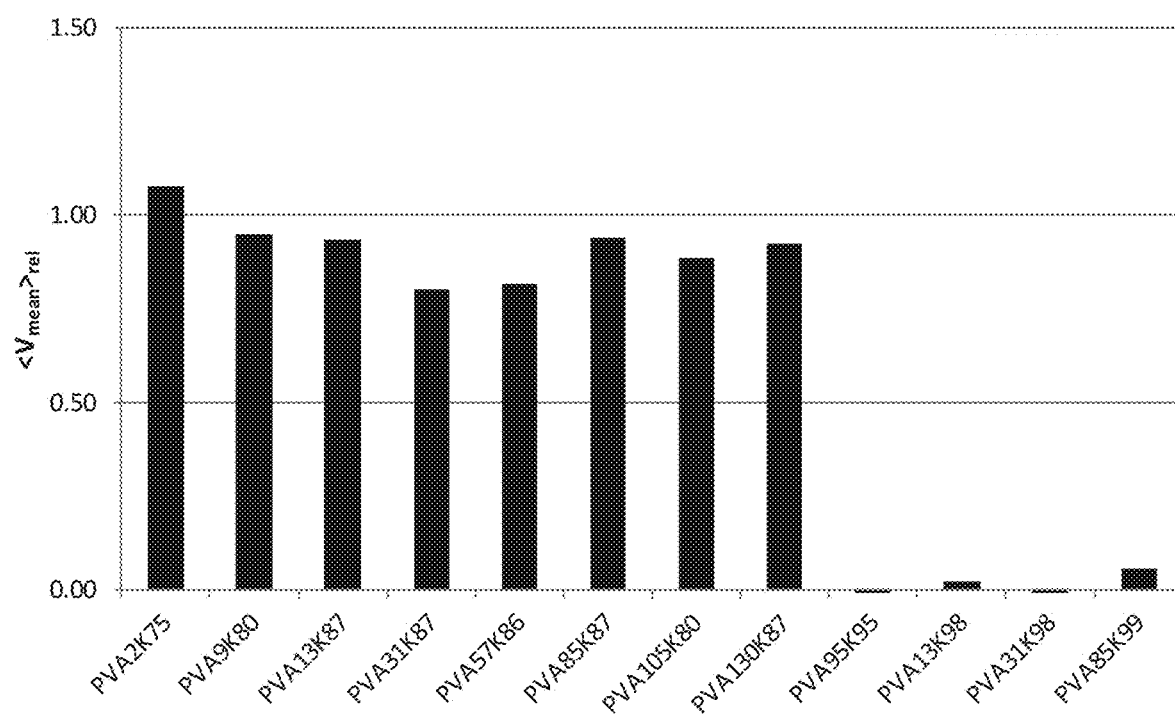
FIG. 2B is a plot showing the relative velocity $<V_{mean}>_{rel}$ in CVM for PSCOO particles coated with various PVAs according to one set of embodiments.

On the other hand, nanoparticles incubated with PVA95K95, PVA13K98, PVA31K98, and PVA85K99 were predominantly or completely immobilized as demonstrated by respective $<V_{mean}>_{rel}$ values of no greater than 0.1 (Table 3 and FIG. 2B).

Figure 3:
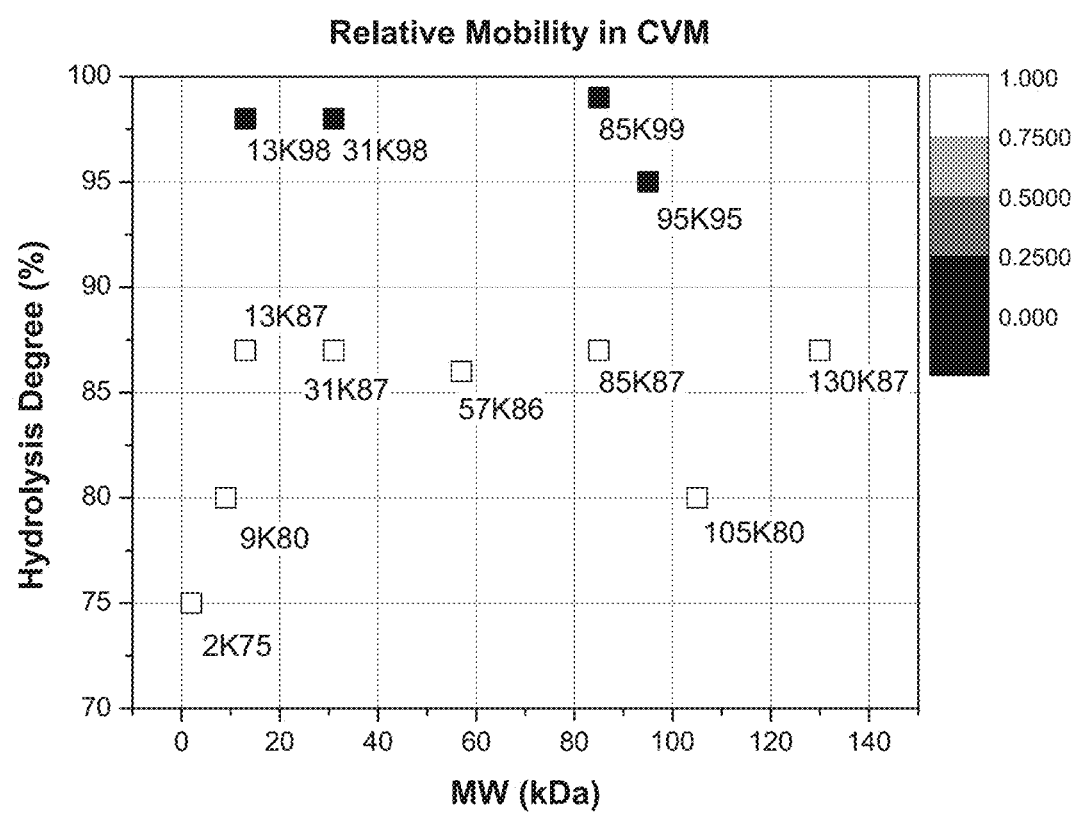
FIG. 3 is a plot showing relative velocity $<V_{mean}>_{rel}$ in CVM for PSCOO particles incubated with various PVAs mapped according to the PVA's molecular weight and degree of hydrolysis, according to one set of embodiments. Each data point represents $<V_{mean}>_{rel}$ for the particles stabilized with a specific PVA.

To identify the characteristics of the PVA that render particles mucus penetrating, $<V_{mean}>_{rel}$ of the nanoparticles prepared by incubation with the various PVAs was mapped with respect to MW and hydrolysis degree of the PVAs used (FIG. 3). It was concluded that at least those PVAs that have the hydrolysis degree of less than 95% rendered the nanocrystals mucus-penetrating. Without wishing to be bound by any theory, it is believed that the unhydrolyzed (vinyl acetate) units of PVA can provide effective hydrophobic association with the surface of the core particles if the content of these segments in the PVA is sufficient (e.g., greater than 5% in some embodiments); while the hydrophilic (vinyl alcohol) units of PVA present at the surface of the coated particles render them hydrophilic and can shield the coated particles from adhesive interactions with mucus.

To further confirm the ability of the specific PVA grades to convert mucoadhesive particles into mucus-penetrating particles by physical adsorption, PSCOO nanoparticles incubated with the various PVAs were tested using the bulk transport assay. In this method, 20 µL of CVM was collected in a capillary tube and one end is sealed with clay. The open end of the capillary tube is then submerged in 20 µL of an aqueous suspension of particles which is 0.5% w/v drug. After the desired time, typically 18 hours, the capillary tube is removed from the suspension and the outside is wiped clean. The capillary containing the mucus sample is placed in an ultracentrifuge tube. Extraction media is added to the tube and incubated for 1 hour while mixing which removes the mucus from the capillary tube and extracts the drug from the mucus. The sample is then spun to remove mucins and other non-soluble components. The amount of drug in the extracted sample can then be quantified using HPLC. The results of these experiments are in good agreement with those of the microscopy method, showing clear differentiation in transport between positive (mucus-penetrating particles) and negative controls (conventional particles). The bulk transport results for PSCOO nanoparticles incubated with the various PVAs are shown in FIG. 4. These results corroborate microscopy/particle tracking findings with PSCOO nanoparticles incubated with the various PVAs and demonstrate the incubating nanoparticles with partially hydrolyzed PVAs enhances mucus penetration.

Example 2

The following describes a non-limiting example of a method of forming mucus-penetrating particles by an emulsification process in the presence of certain poly(vinyl alcohol) polymers (PVA). Polylactide (PLA), a biodegradable pharmaceutically relevant polymer was used as a material to form the core particle via an oil-in-water emulsification process. The PVAs acted as emulsion stabilizers and surface-altering agents forming coatings around the produced core particles. PVA of various molecular weights (MW) and hydrolysis degrees were evaluated to determine effectiveness of the formed particles in penetrating mucus.

PLA solution in dichloromethane was emulsified in aqueous solution in the presence of various PVA to determine whether certain PVAs can physically (non-covalently) coat the surface of generated nanoparticles with a coating that would lead to rapid particle penetration in mucus. In these experiments, the PVA acted as an surfactant that forms a stabilizing coating around droplets of emulsified organic phase that, upon solidification, form the core particles The resulting particles were tested for their mobility in mucus, although in other embodiments, PVA may be exchanged with other surface-altering agents that can increase mobility of the particles in mucus. The PVAs tested ranged in the average molecular weight from 2 kDa to 130 kDa and in the average hydrolysis degree from 75% to 99+%. The PVAs that were tested are listed in Table 1, shown above.

The emulsification-solvent evaporation process was as follows: Approximately 0.5 mL of 20-40 mg/ml solution of PLA (Polylactide grade 100DL7A, purchased from Surmodics) in dichloromethane was emulsified in approximately 4 mL of an aqueous PVA solution (0.5-2% wt) by sonication to obtain a stable emulsion with the target number-average particle size of <500 nm. Obtained emulsions were immediately subjected to exhaustive rotary evaporation under reduced pressure at room temperature to remove the organic solvent. Obtained suspensions were filtered through 1 micron glass fiber filters to remove any agglomerates. Table 4 lists the particle size characteristics of the nanosuspensions obtained by this emulsification procedure with the various PVA. In all cases, a fluorescent organic dye Nile Red was added to the emulsified organic phase to fluorescently label the resulting particles.

TABLE 4

Particle size measured by DLS in nanosuspensions obtained by the emulsification process with various PVA.

| PVA Grade | Z-Ave D (nm) | N-Ave D (nm) |
|---|---|---|
| PVA2K75 | 186 | 156 |
| PVA10K80 | 208 | 173 |
| PVA13K98 | 245 | 205 |
| PVA31K87 | 266 | 214 |
| PVA31K98 | 245 | 228 |
| PVA85K87 | 356 | 301 |
| PVA85K99 | 446 | 277 |
| PVA95K95 | 354 | 301 |
| PVA105K80 | 361 | 300 |
| PVA130K87 | 293 | 243 |

The mobility and distribution of the produced nanoparticles in human cervicovaginal mucus (CVM) were characterized using fluorescence microscopy and multiple particle tracking software. In a typical experiment, ≤0.5 uL of a nanosuspension (diluted if necessary to the PVA concentration of ~0.5%) was added to $20_11.1$ of fresh CVM along with controls. Conventional nanoparticles (200 nm blue fluorescent carboxylate-modified polystyrene microspheres from Invitrogen) were used as a negative control to confirm the barrier properties of the CVM samples. Yellow-green fluorescent polystyrene nanoparticles covalently coated with PEG 2 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (observed through a Texas Red filter set due to the encapsulated Nile Red), negative control (observed through a DAPI filter set), and positive control (observed through a FITC filter set). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, ensemble-average (absolute) velocity is then converted to relative sample velocity $<V_{mean}>_{rel}$ according to the formula shown in Equation 1. Multiple particle tracking confirmed that in all tested CVM samples the negative controls were constrained, while the positive controls were mobile as demonstrated by the differences in $<V_{mean}>$ for the positive and negative controls (Table 5).

TABLE 5

Transport of PLA nanoparticles obtained by the emulsification process with various PVAs (sample) and controls in CVM: Ensemble-average velocity $<V_{mean}>$ (um/s) and relative sample velocity $<V_{mean}>_{rel}$

| Stabilizer/Surface-altering agent | Negative Control | | Positive Control | | Sample | | Sample (relative) | |
|---|---|---|---|---|---|---|---|---|
| | $<V_{mean}>$ | SD | $<V_{mean}>$ | SD | $<V_{mean}>$ | SD | $<V_{mean}>_{rel}$ | SD |
| PVA2K75 | 0.95 | 0.64 | 5.5 | 0.92 | 5.51 | 1.2 | 1.00 | 0.39 |
| PVA9K80 | 0.72 | 0.47 | 5.61 | 0.79 | 4.6 | 1.5 | 0.79 | 0.35 |
| PVA31K87 | 0.63 | 0.60 | 4.94 | 1.50 | 3.36 | 1.84 | 0.63 | 0.51 |
| PVA85K87 | 0.57 | 0.4 | 4.49 | 1.21 | 2.9 | 1.56 | 0.59 | 0.45 |
| PVA105K80 | 0.69 | 0.56 | 4.85 | 1.54 | 3.55 | 1.26 | 0.69 | 0.43 |
| PVA130K87 | 0.95 | 0.54 | 4.98 | 1.25 | 3.46 | 1.23 | 0.62 | 0.39 |
| PVA95K95 | 1.39 | 1.28 | 5.72 | 1.57 | 1.63 | 1.5 | 0.06 | 0.46 |
| PVA13K98 | 1.02 | 0.49 | 5.09 | 0.99 | 2.61 | 1.54 | 0.39 | 0.41 |
| PVA31K98 | 1.09 | 0.6 | 5.09 | 0.9 | 2.6 | 1.13 | 0.38 | 0.34 |
| PVA85K99 | 0.47 | 0.33 | 5.04 | 2.2 | 0.81 | 0.77 | 0.07 | 0.19 |

It was discovered that nanoparticles prepared in the presence of certain (but, interestingly, not all) PVA transported through CVM at the same rate or nearly the same velocity as the positive control. Specifically, the particles stabilized with PVA2K75, PVA9K80, PVA13K87, PVA31K87, PVA85K87, PVA105K80, and PVA130K87 exhibited $<V_{mean}>$ that significantly exceeded those of the negative controls and were indistinguishable, within experimental error, from those of the positive controls, as shown in Table 5 and FIG. 5A. For these samples, $<V_{mean}>_{rel}$ values exceeded 0.5, as shown in FIG. 5B.

On the other hand, pyrene nanoparticles obtained with PVA95K95, PVA13K98, PVA31K98, and PVA85K99 were predominantly or completely immobilized as demonstrated by respective $<V_{mean}>_{rel}$ values of no greater than 0.4 (Table 5 and FIG. 5B). To identify the characteristics of the PVA that render particles mucus penetrating, $<V_{mean}>_{rel}$ of the nanoparticles prepared with the various PVAs was mapped with respect to MW and hydrolysis degree of the PVAs used (FIG. 6). It was concluded that at least those PVAs that have the hydrolysis degree of less than 95% rendered the nanocrystals mucus-penetrating. Without wishing to be bound by any theory, it is believed that the unhydrolyzed (vinyl acetate) units of PVA can provide effective hydrophobic association with the surface of the core particles if the content of these segments in the PVA is sufficient (e.g., greater than 5% in some embodiments); while the hydrophilic (vinyl alcohol) units of PVA present at the surface of the coated particles render them hydrophilic and can shield the coated particles from adhesive interactions with mucus.

Example 3

The following describes a non-limiting example of a method of forming mucus-penetrating non-polymeric solid particles by nanomilling in the presence of certain poly (vinyl alcohol) polymers (PVA). Pyrene, a model hydrophobic compound, was used as the core particle processed by a nanomilling. The PVA acted as nanomilling aids facilitating particle size reduction of the core particles and surface-altering agents forming coatings around the core particles. PVA of various molecular weights (MW) and hydrolysis degrees were evaluated to determine effectiveness of the nanomilled particles in penetrating mucus.

Pyrene was nanomilled in aqueous dispersions in the presence of various PVA to determine whether PVAs of certain MW and hydrolysis degree can: 1) aid particle size reduction to several hundreds of nanometers and 2) physically (non-covalently) coat the surface of generated nanoparticles with a mucoinert coating that would minimize particle interactions with mucus constituents and prevent mucus adhesion. In these experiments, the PVA acted as a coating around the core particles, and the resulting particles were tested for their mobility in mucus. The PVAs tested ranged in the average molecular weight from 2 kDa to 130 kDa and in the average hydrolysis degree from 75% to 99+%. The PVAs that were tested are listed in Table 1, shown above. A variety of other polymers, oligomers, and small molecules listed in Table 6, including pharmaceutically relevant excipients such as polyvinylpyrrolidones (Kollidon), hydroxypropyl methylcellulose (Methocel), Tween, Span, etc., were tested in a similar manner.

TABLE 6

Other surface-altering agents tested with pyrene as a model compound.

| Chemical Family | Grades |
|---|---|
| Polyvinylpyrrolidone (PVP) | Kollidon 17 |
| | Kollidon 25 |
| | Kollindon 30 |
| PVA-poly(ethylene glycol) graft-copolymer | Kollicoat IR |
| Hydroxypropyl methylcellulose (HPMC) | Methocel E50 |
| | Methocel K100 |
| Non-ionic polyoxyethylene surfactants | Solutol HS 15 |
| | Span 20 |
| | Span 80 |
| | Triton X100 |
| | Tween 20 |
| | Tween 80 |
| | Tyloxapol |
| Non-ionic small molecule surfactants | Octyl glucoside |
| Ionic small molecule surfactants | Cetytrimethylammonium bromide (CTAB) |
| | Sodium dodecyl sulfate (SDS) |

An aqueous dispersion containing pyrene and one of the stabilizers/surface-altering agents listed above was stirred with milling media until particle size was reduced below 500 nm (as measured by dynamic light scattering). Table 7 lists particle size characteristics of pyrene particles obtained by nanomilling in the presence of the various stabilizers/surface-altering agents. When Span 20, Span 80, or Octyl glucoside were used as stabilizers/surface-altering agents, stable nanosuspensions could not be obtained. Therefore, these stabilizers/surface-altering agents were excluded from further investigation due to their inability to effectively aid particle size reduction.

TABLE 7

Particle size measured by DLS in nanosuspensions obtained by nanomilling of pyrene with various stabilizers/surface-altering agents.

| Stabilizer/surface-altering agent | Z-Ave D (nm) | N-Ave D (nm) |
|---|---|---|
| PVA2K75 | 340 | 301 |
| PVA9K80 | 380 | 337 |
| PVA13K87 | 375 | 326 |
| PVA13K98 | 396 | 314 |
| PVA31K87 | 430 | 373 |
| PVA31K98 | 344 | 220 |
| PVA85K87 | 543 | 434 |
| PVA85K99 | 381 | 236 |
| PVA95K95 | 534 | 392 |
| PVA130K87 | 496 | 450 |
| Kollidon 17 | 237 | 163 |
| Kollidon 25 | 307 | 210 |
| Kollindon 30 | 255 | 185 |
| Kollicoat IR | 364 | 192 |
| Methocel E50 | 244 | 160 |
| Methocel K100 | 375 | 216 |
| Tween 20 | 567 | 381 |
| Tween 80 | 553 | 322 |
| Solutol HS | 576 | 378 |
| Triton X100 | 410 | 305 |
| Tyloxapol | 334 | 234 |
| Cremophor RH40 | 404 | 373 |
| Span 20 | not measurable* | |
| Span 80 | not measurable* | |
| Octyl glucoside | not measurable* | |
| SDS | 603 | 377 |
| CTAB | 432 | 354 |

*milling with Span 20, Span 80, Octyl glucoside failed to effectively reduce pyrene particle size and produce stable nanosuspensions.

The mobility and distribution of the produced pyrene nanoparticles in human cervicovaginal mucus (CVM) were characterized using fluorescence microscopy and multiple particle tracking software. In a typical experiment, ≤0.5 uL of a nanosuspension (diluted if necessary to the surfactant concentration of ~1%) was added to $20_11.1$ of fresh CVM along with controls. Conventional nanoparticles (200 nm yellow-green fluorescent carboxylate-modified polystyrene microspheres from Invitrogen) were used as a negative control to confirm the barrier properties of the CVM samples. Red fluorescent polystyrene nanoparticles covalently coated with PEG 5 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (pyrene), negative control, and positive control (natural blue fluorescence of pyrene allowed observing of pyrene nanoparticles separately from the controls). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, ensemble-average (absolute) velocity is then converted to relative sample velocity $<V_{mean}>_{rel}$ according to the formula shown in Equation 1.

Prior to quantifying mobility of pyrene particles, their spatial distribution in the mucus sample was assessed visually. It was found that pyrene/Methocel nanosuspensions did not achieve uniform distribution in CVM and strongly aggregated into domains much larger than the mucus mesh size (data not shown). Such aggregation is indicative of mucoadhesive behavior and effectively prevents mucus penetration. Therefore, further quantitative analysis of particle mobility was deemed unnecessary. Similarly to the positive control, all other tested pyrene/surface-altering agent systems achieved a fairly uniform distribution in CVM. Multiple particle tracking confirmed that in all tested CVM samples the negative controls were constrained, while the positive controls were mobile as demonstrated by the differences in $<V_{mean}>$ for the positive and negative controls (Table 8).

TABLE 8

Transport of pyrene nanoparticles (sample) obtained with various stabilizers/surface-altering agents and controls in CVM: Ensemble-average velocity $<V_{mean}>$ (um/s) and relative sample velocity $<V_{mean}>_{rel}$

| Stabilizer/Surface-altering agent | Negative Control | | Positive Control | | Sample | | Sample (relative) | |
|---|---|---|---|---|---|---|---|---|
| | $<V_{mean}>$ | SD | $<V_{mean}>$ | SD | $<V_{mean}>$ | SD | $<V_{mean}>_{rel}$ | SD |
| PVA2K75 | 0.4 | 0.24 | 5.73 | 0.73 | 4.73 | 1.08 | 0.81 | 0.24 |
| PVA9K80 | 0.36 | 0.20 | 6.00 | 0.70 | 6.19 | 1.13 | 1.03 | 0.24 |
| PVA13K87 | 1.01 | 1.21 | 5.09 | 0.98 | 4.54 | 1.03 | 0.87 | 0.51 |
| PVA31K87 | 1.28 | 1.14 | 4.88 | 0.6 | 4.57 | 1.123 | 0.91 | 0.55 |
| PVA85K87 | 1.05 | 0.9 | 4.1 | 0.57 | 3.3 | 0.98 | 0.74 | 0.51 |
| PVA130K87 | 0.51 | 0.82 | 5.29 | 0.73 | 4.12 | 1.49 | 0.76 | 0.40 |
| PVA95K95 | 0.4 | 0.27 | 4.53 | 1.03 | 0.67 | 0.6 | 0.07 | 0.16 |
| PVA13K98 | 0.61 | 0.42 | 2.13 | 0.99 | 1.29 | 0.57 | 0.45 | 0.56 |
| PVA31K98 | 0.68 | 0.87 | 5.77 | 1.24 | 2.69 | 2.02 | 0.39 | 0.45 |
| PVA85K99 | 0.43 | 0.23 | 5.42 | 0.97 | 2.23 | 1.60 | 0.36 | 0.33 |
| Kollicoat IR | 0.62 | 0.62 | 5.39 | 0.55 | 0.92 | 0.81 | 0.06 | 0.22 |
| Kollidon 17 | 1.69 | 1.8 | 5.43 | 0.98 | 0.82 | 0.59 | −0.23 | −0.52 |
| Kollidon 25 | 0.41 | 0.34 | 5.04 | 0.64 | 1.29 | 1.09 | 0.19 | 0.25 |
| Kollindon 30 | 0.4 | 0.2 | 4.28 | 0.57 | 0.35 | 0.11 | −0.01 | 0.06 |
| Methocel E50* | | | | | | | | |
| Methocel K100* | | | | | | | | |

TABLE 8-continued

Transport of pyrene nanoparticles (sample) obtained with various stabilizers/surface-altering agents and controls in CVM: Ensemble-average velocity $<V_{mean}>$ (um/s) and relative sample velocity $<V_{mean}>_{rel}$

| Stabilizer/Surface- | Negative Control | | Positive Control | | Sample | | Sample (relative) | |
|---|---|---|---|---|---|---|---|---|
| altering agent | $<V_{mean}>$ | SD | $<V_{mean}>$ | SD | $<V_{mean}>$ | SD | $<V_{mean}>_{rel}$ | SD |
| Tween 20 | 0.77 | 0.93 | 5.35 | 1.76 | 1.58 | 2.02 | 0.18 | 0.49 |
| Tween 80 | 0.46 | 0.34 | 3.35 | 1.89 | 0.94 | 0.5 | 0.17 | 0.24 |
| Solutol HS | 0.42 | 0.13 | 3.49 | 0.5 | 0.8 | 0.6 | 0.12 | 0.20 |
| Triton X100 | 0.26 | 0.13 | 4.06 | 1.11 | 0.61 | 0.19 | 0.09 | 0.07 |
| Tyloxapol | 0.5 | 0.5 | 3.94 | 0.58 | 0.42 | 0.23 | −0.02 | −0.16 |
| Cremophor RH40 | 0.48 | 0.21 | 3.2 | 0.97 | 0.49 | 0.24 | 0.00 | 0.12 |
| SDS | 0.3 | 0.12 | 5.99 | 0.84 | 0.34 | 0.15 | 0.01 | 0.03 |
| CTAB | 0.39 | 0.09 | 4.75 | 1.79 | 0.32 | 0.31 | −0.02 | −0.07 |

*Aggregated in CVM, hence not mucus-penetrating (velocity in CVM not measured)

It was discovered that nanoparticles obtained in the presence of certain (but, interestingly, not all) PVA transported through CVM at the same rate or nearly the same velocity as the positive control. Specifically, pyrene nanoparticles stabilized with PVA2K75, PVA9K80, PVA13K87, PVA31K87, PVA85K87, and PVA130K87 exhibited $<V_{mean}>$ that significantly exceeded those of the negative controls and were indistinguishable, within experimental error, from those of the positive controls, as shown in Table 8 and FIG. 7A. For these samples, $<V_{mean}>_{rel}$ values exceeded 0.5, as shown in FIG. 7B.

On the other hand, pyrene nanoparticles obtained with the other stabilizers/surface-altering agents, including PVA95K95, PVA13K98, PVA31K98, and PVA85K99, were predominantly or completely immobilized as demonstrated by respective $<V_{mean}>_{rel}$ values of no greater than 0.5 and, with most stabilizers/surface-altering agents, no greater than 0.4 (Table 8 and FIG. 7B). Additionally, FIGS. 8A-8F are histograms showing distribution of $V_{mean}$ within an ensemble of particles. These histograms illustrate muco-diffusive behavior of samples stabilized with PVA2K75 and PVA9K80 (similar histograms were obtained for samples stabilized with PVA13K87, PVA31K87, PVA85K87, and PVA130K87, but are not shown here) as opposed to muco-adhesive behavior of samples stabilized with PVA31K98, PVA85K99, Kollidon 25, and Kollicoat IR (chosen as representative muco-adhesive samples).

To identify the characteristics of the PVA that render pyrene nanocrystals mucus penetrating, $<V_{mean}>_{rel}$ of the pyrene nanocrystals stabilized with various PVAs was mapped with respect to MW and hydrolysis degree of the PVAs used (FIG. 9). It was concluded that at least those PVAs that have the hydrolysis degree of less than 95% rendered the nanocrystals mucus-penetrating. Without wishing to be bound by any theory, it is believed that the unhydrolyzed (vinyl acetate) segments of PVA can provide effective hydrophobic association with the surface of the core particles if the content of these segments in the PVA is sufficient (e.g., greater than 5% in some embodiments); while the hydrophilic (vinyl alcohol) segments of PVA present at the surface of the coated particles render them hydrophilic and can shield the coated particles from adhesive interactions with mucus.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
   delivering across a mucosal barrier a composition comprising
   (a) a plurality of mucus-penetrating coated particles, wherein each of the coated particles comprises:
      (i) a core particle comprising a pharmaceutical agent or a salt thereof, wherein the pharmaceutical agent constitutes at least about 80 wt % of the core particle; and
      (ii) a mucus penetration-enhancing coating comprising a surface-altering agent surrounding the core particle, wherein the surface-altering agent comprises a poly(vinyl alcohol) (PVA) polymer having pendant hydroxyl groups on the backbone of the PVA polymer, the PVA polymer having a molecular weight of at least about 1 kDa and less than or equal to about 1000 kDa, wherein the hydrolysis level of the PVA polymer is at least about 30% and less than about 95%, and
   (b) one or more pharmaceutically acceptable excipients or carriers;
   wherein the coated particles have an increased mobility in human mucus relative to uncoated particles;
   wherein the coated particles have an average size of less than 1 µm.

2. The method of claim 1, wherein the surface-altering agent is non-covalently adsorbed to the core particles.

3. The method of claim 1, wherein the polymer has a molecular weight of at least about 2 kDa.

4. The method of claim 3, wherein the polymer has a molecular weight of less than or equal to about 200 kDa.

5. The method of claim 1, wherein the hydrolysis level is at least about 40%.

6. The method of claim 1, wherein the hydrolysis level is less than about 90%.

7. The method of claim 1, wherein each of the core particles comprises a solid crystalline pharmaceutical agent or a salt thereof.

8. The method of claim 1, wherein each of the core particles comprises a solid amorphous pharmaceutical agent or a salt thereof.

9. The method of claim 1, wherein each of the core particles comprises a salt of the pharmaceutical agent.

10. The method of claim 1, wherein each of the core particles comprises a pharmaceutical agent or a salt thereof that is encapsulated in a polymer, a lipid, a protein, or a combination thereof.

11. The method of claim 1, wherein the pharmaceutical agent is at least one of a therapeutic agent or a diagnostic agent.

12. The method of claim 1, wherein the pharmaceutical agent is at least one of a small molecule, a peptide, a peptidomimetic, a protein, a nucleic acid, or a lipid.

13. The method of claim 1, wherein the pharmaceutical agent or a salt thereof has an aqueous solubility of less than or equal to about 1 mg/mL at 25° C.

14. The method of claim 1, wherein the pharmaceutical agent constitutes at least about 80 wt % of the core particle.

15. The method of claim 1, wherein the core particle has an average size of at least 20 nm and less than 500 nm.

16. The method of claim 1, wherein the coated particles have an average size of at least 20 nm and less than 1 µm.

17. The method of claim 1, wherein the coated particles have a relative velocity of greater than 0.5 in mucus.

18. The method of claim 17, wherein the mucus is human cervicovaginal mucus.

19. The method of claim 17, wherein the coated particles have a relative velocity of greater than 0.8 in mucus.

20. The method of claim 1, wherein the liquid carrier is aqueous.

21. The method of claim 1 wherein the mucosal barrier is in an oral tissue, ophthalmic tissue, gastrointestinal tissue, nasal tissue, respiratory tissue, or a genital tissue.

22. A method of forming coated particles, comprising:
   coating a plurality of core particles with a surface-altering agent to form coated particles,
   wherein the surface-altering agent comprises a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed,
   wherein each of the core particles comprises a pharmaceutical agent or a salt thereof, and
   wherein the coated particles have a relative velocity of greater than 0.5 in mucus.

* * * * *